US010273482B2

(12) United States Patent
Labow et al.

(10) Patent No.: US 10,273,482 B2
(45) Date of Patent: Apr. 30, 2019

(54) DSRNA FOR TREATING VIRAL INFECTION

(71) Applicant: Arrowhead Pharmaceuticals, Inc., Pasedena, CA (US)

(72) Inventors: Mark Aron Labow, Cambridge, MA (US); Larry Alexander Gaither, Cambridge, MA (US); Jason Borawski, Cambridge, MA (US)

(73) Assignee: Arrowhead Pharmaceuticals, Inc., Pasedena, CA (US)

( * ) Notice: Subject to any disclaimer, the term of this patent is extended or adjusted under 35 U.S.C. 154(b) by 0 days.

(21) Appl. No.: 15/471,221

(22) Filed: Mar. 28, 2017

(65) Prior Publication Data

US 2017/0204417 A1    Jul. 20, 2017

Related U.S. Application Data

(62) Division of application No. 14/812,187, filed on Jul. 29, 2015, now abandoned, which is a division of application No. 14/069,642, filed on Nov. 1, 2013, now Pat. No. 9,133,462, which is a division of application No. 13/359,129, filed on Jan. 26, 2012, now Pat. No. 8,603,995, which is a division of application No. 12/667,631, filed as application No. PCT/EP2008/058706 on Jul. 4, 2008, now abandoned.

(60) Provisional application No. 60/948,100, filed on Jul. 5, 2007.

(51) Int. Cl.
  *C12N 15/113*   (2010.01)
  *A61K 31/713*   (2006.01)

(52) U.S. Cl.
  CPC ........ *C12N 15/1137* (2013.01); *A61K 31/713* (2013.01); *C12N 2310/14* (2013.01); *C12N 2310/314* (2013.01); *C12N 2310/315* (2013.01); *C12N 2310/321* (2013.01); *C12N 2310/322* (2013.01); *C12N 2310/3233* (2013.01); *C12N 2310/3515* (2013.01); *C12N 2310/531* (2013.01); *Y02A 50/385* (2018.01)

(58) Field of Classification Search
  None
  See application file for complete search history.

(56) References Cited

U.S. PATENT DOCUMENTS

| | | |
|---|---|---|
| 3,687,808 A | 8/1972 | Merigan et al. |
| 4,469,863 A | 9/1984 | Ts'o et al. |
| 4,476,301 A | 10/1984 | Imbach et al. |
| 4,868,116 A | 9/1989 | Morgan et al. |
| 4,980,286 A | 12/1990 | Morgan et al. |
| 5,023,243 A | 6/1991 | Tullis |
| 5,034,506 A | 7/1991 | Summerton et al. |
| 5,138,045 A | 8/1992 | Cook et al. |
| 5,139,941 A | 8/1992 | Muzycka et al. |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,212,295 A | 5/1993 | Cook |
| 5,214,132 A | 5/1993 | Weis et al. |
| 5,216,141 A | 6/1993 | Benner |
| 5,218,105 A | 6/1993 | Cook et al. |
| 5,223,168 A | 6/1993 | Holt |
| 5,235,033 A | 8/1993 | Summerton et al. |
| 5,252,479 A | 10/1993 | Srivastava |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |

(Continued)

FOREIGN PATENT DOCUMENTS

| | | |
|---|---|---|
| WO | 1989002468 A1 | 3/1989 |
| WO | 1989005345 A1 | 6/1989 |

(Continued)

OTHER PUBLICATIONS

Anderson W F (1998), Nature 392: 25-30.

(Continued)

*Primary Examiner* — Tracy Vivlemore
(74) *Attorney, Agent, or Firm* — Robert M. Teigen; Paul VanderVelde

(57) ABSTRACT

The invention relates to double-stranded ribonucleic acids (dsRNAs) targeting gene expression of phosphatidylinositol 4-kinase (PI4K), in particular human phosphatidylinositol 4-kinase, catalytic, beta polypeptide (PIK4CB) or human phosphatidylinositol 4-kinase, catalytic, alpha polypeptide (PIK4CA), and their use for treating infection by positive stranded RNA viruses such as hepatitis C virus (HCV). Each dsRNA comprises an antisense strand having a nucleotide sequence which is less that 30 nucleotides in length, generally 19-25 nucleotides in length, and which is substantially complementary to at least a part of the PIK4CB or PIK4CA target mRNA. A plurality of such dsRNA may be employed to provide therapeutic benefit. The invention also relates to a pharmaceutical composition comprising the dsRNA together with a pharmaceutically acceptable carrier, and including a delivery modality such as fully encapsulated liposomes or lipid complexes. The invention further includes methods for treating diseases caused by positive stranded RNA virus infection using the pharmaceutical compositions; and methods for inhibiting the propagation of positive stranded RNA viruses in and between cells.

11 Claims, 10 Drawing Sheets

Specification includes a Sequence Listing.

(56) References Cited

U.S. PATENT DOCUMENTS

| | | |
|---|---|---|
| 5,278,302 A | 1/1994 | Caruthers et al. |
| 5,286,717 A | 2/1994 | Cohen et al. |
| 5,321,131 A | 6/1994 | Agrawal et al. |
| 5,328,470 A | 7/1994 | Nabel et al. |
| 5,378,825 A | 1/1995 | Cook et al. |
| 5,386,023 A | 1/1995 | Sanghvi et al. |
| 5,399,676 A | 3/1995 | Froehler |
| 5,405,938 A | 4/1995 | Summerton et al. |
| 5,405,939 A | 4/1995 | Suhadolnik et al. |
| 5,434,257 A | 7/1995 | Matteucci et al. |
| 5,453,496 A | 9/1995 | Caruthers et al. |
| 5,455,233 A | 10/1995 | Spielvogel et al. |
| 5,457,191 A | 10/1995 | Cook et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,489,677 A | 2/1996 | Sanghvi et al. |
| 5,506,351 A | 4/1996 | Mcgee |
| 5,519,126 A | 5/1996 | Hecht |
| 5,521,302 A | 5/1996 | Cook |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,554,746 A | 9/1996 | Ravikumar et al. |
| 5,561,225 A | 10/1996 | Maddry et al. |
| 5,563,253 A | 10/1996 | Agrawal et al. |
| 5,571,799 A | 11/1996 | Tkachuk et al. |
| 5,571,902 A | 11/1996 | Ravikumar et al. |
| 5,578,718 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,596,086 A | 1/1997 | Matteucci et al. |
| 5,599,797 A | 2/1997 | Cook et al. |
| 5,602,240 A | 2/1997 | DeMesmaeker et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,633,360 A | 5/1997 | Bischofberger et al. |
| 5,663,312 A | 9/1997 | Chaturvedula |
| 5,677,437 A | 10/1997 | Teng et al. |
| 5,677,439 A | 10/1997 | Weis et al. |
| 5,697,248 A | 12/1997 | Brown |
| 6,054,299 A | 4/2000 | Conrad |
| 6,262,241 B1 | 7/2001 | Cook et al. |
| 6,271,359 B1 | 8/2001 | Norris et al. |
| 6,670,486 B1 | 12/2003 | Bakonyl et al. |
| 7,348,314 B2 | 3/2008 | Limmer et al. |
| 2004/0001811 A1 | 1/2004 | Kreutzer et al. |
| 2004/0002153 A1* | 1/2004 | Monia ............... A61K 48/00 435/375 |
| 2006/0211057 A1* | 9/2006 | Azar ................ C12Q 1/485 435/7.23 |
| 2007/0207974 A1 | 9/2007 | Khvorova et al. |
| 2007/0212717 A1* | 9/2007 | Kukolj ............. G01N 33/5767 435/5 |
| 2008/0097092 A1 | 4/2008 | Khvorova et al. |

FOREIGN PATENT DOCUMENTS

| | | |
|---|---|---|
| WO | 1989007136 A2 | 8/1989 |
| WO | 1992007573 A1 | 5/1992 |
| WO | 1993007883 A1 | 4/1993 |
| WO | 1993024641 A2 | 12/1993 |
| WO | 1994013788 A1 | 6/1994 |
| WO | 1996040964 A2 | 12/1996 |
| WO | 1999032619 A1 | 7/1999 |
| WO | 1999053050 A1 | 10/1999 |
| WO | 1999061631 A1 | 12/1999 |
| WO | 2000022113 A1 | 4/2000 |
| WO | 2000022114 A1 | 4/2000 |
| WO | 20030016572 A1 | 2/2003 |
| WO | 20030070750 A2 | 8/2003 |
| WO | 20030070918 A2 | 8/2003 |
| WO | 20030082255 A2 | 10/2003 |
| WO | 20040065601 A2 | 8/2004 |
| WO | 2005028650 A2 | 3/2005 |
| WO | 20050021749 A1 | 3/2005 |
| WO | 2005119262 A2 | 12/2005 |
| WO | 20060074346 A2 | 7/2006 |
| WO | 2007001928 A2 | 1/2007 |

OTHER PUBLICATIONS

Armentano et al., 1990, Proc. Natl. Acad. Sci. USA 87:6141-6145.
Berkner, et al., BioTechniques (1988) 6:616.
Borawski J, Lindeman A, Buxton F, Labow M, Gaither LA. Optimization procedure for small interfering RNA transfection in a 384-well format. J Biomol Screen. Jun. 2007;12(4):546-59. Epub Apr. 13, 2007.
Braasch, D.A. and D.R. Corey, Chem. Biol. (2001), 8:1-7.
Bucchini et al., 1986, Proc. Natl. Acad. Sci. USA 83:2511-2515.
Chen et al. (1994) Proc. Natl. Acad. Sci. USA 91:3054-3057.
Chowdhury et al., 1991, Science 254:1802-1805.
Cone et al., 1984, Proc. Natl. Acad. Sci. USA 81:6349-6353.
Crooke et al., J. Pharmacol. Exp. Ther., 1996, 277:923-937.
Dai et al., 1992, Proc. Natl.Acad. Sci. USA 89:10892-10895.
Danos and Mulligan, Proc. Natl. Acad. Sci. USA (1998) 85:6460-6464.
Docherty et al., 1994, FASEB J. 8:20-24.
Ferry et al., 1991, Proc. Natl. Acad. Sci. USA 88:8377-8381.
Fisher K J et al. (1996), J. Virol, 70: 520-532.
Gassmann, et al., Proc. Natl. Acad. Sci. USA (1995) 92:1292-1296.
Godi et al.; ARF mediates recruitment of PtdIns-4-OH kinase-beta and stimulates synthesis of PtdIns(4,5)P2 on the Golgi complex. Nat Cell Biol. Sep. 1999;1(5):280-7.
Hsu et al., 1992, J. Infectious Disease, 166:769-775.
Huber et al., 1991, Proc. Natl. Acad. Sci. USA 88:8039-8043.
Wagner, Nat. Med. (1995) 1:1116-8.
Kabanov et al., FEBS Lett., 1990, 259:327-330.
Kay et al., 1992, Human Gene Therapy 3:641-647.
Letsinger et al., Proc. Natl. Acad. Sci. USA, 1989, 86:6553-6556.
Lohmann, V., et. al. (1999) Science. 285:110-113.
Manoharan et al., Ann. N.Y. Acad. Sci., 1992, 660:306-309.
Manoharan et al., Bioorg. Med. Chem. Let., 1993, 3:2765-2770.
Manoharan et al., Bioorg. Med. Chem. Lett., 1994, 4:1053-1060.
Manoharan et al., Tetrahedron Lett., 1995, 36:3651-3654.
Manoharan et al., Nucleosides & Nucleotides, 1995, 14:969-973.
Manoharan Antisense & Nucleic Acid Drug Development 2002, 12, 103-128.
Mishra et al., Biochim. Biophys. Acta, 1995, 1264:229-237.
Moffat J. et al., A Lentiviral RNAi Library for Human and Mouse Genes Applied to an Arrayed Viral High-Content Screen. Cell, 124, 1283-1298 (2006).
Morrissey et al. Nat Biotechnol. Aug. 2005;23(8):1002-7. Epub Jul. 24, 2005.
Oberhauser et al., Nucl. Acids Res., 1992, 20:533-538.
Rabinowitz J E et al. (2002), J Virol 76:791-801.
Ridsdale et al.; Cholesterol is required for efficient endoplasmic reticulum-to-Golgi transport of secretory membrane proteins. Mol Biol Cell. Apr. 2006;17(4):1593-605.
Rosenfeld et al. 1991, Science 252:431-434.
Rosenfeld et al. (1992), Cell 68:143-155.
Rubinson D A et al., Nat. Genet. 33:401-406; (2003).
Saison-Behmoras et al., EMBO J., 1991, 10:1111-1118.
Samulski R et al. (1987), J. Virol. 61: 3096-3101.
Samulski R et al. (1989), J. Virol. 63: 3822-3828.
Shea et al., Nucl. Acids Res., 1990, 18:3777-3783.
Stewart, S.A., et al., Lentivirus-delivered stable gene silencing by RNAi in primary cells., RNA, 9, 493-501 (2003).
Svinarchuk et al., Biochimie, 1993, 75:49-54.
Templeton et al. (Nature Biotechnology, 15: 647-652 (1997).

(56) References Cited

OTHER PUBLICATIONS

Thomson BJ, Finch RG. Hepatitis C virus infection. Clin Microbiol Infect. Feb. 2005;11(2):86-94.
Toth et al.; Phosphatidylinositol 4-kinase IIIbeta regulates the transport of ceramide between the endoplasmic reticulum and Golgi. J Biol Chem. Nov. 24, 2006;281(47):36369-77.
Van Beusechem et al., 1992, Proc. Nad. Acad. Sci. USA 89:7640-19.
Wheeler, J.J. et al. 1999. Gene Ther. 6, 271-281.
Elbashir, et al., EMBO Journal, 20:6877-6888 (2001).
Balla, et al.; "A Plasma Membrane Pool of Phosphatidylinositol 4-Phosphate is Generated by Phosphyatidylinositol 4-Kinase Type-III Alpha: Studies with the PH Domains of the Oxysterol Binding Protein and FAPP1"; Molecular Biology of the Cell; 16(3):1282-1295 (2005).
Ding, et al.; "8 Rational design of siRNAs with the Sfold Software"; In RNA Interference Technology, ed. Appasani [Cambridge University Press, Cambridge UK]; Chapter 8, pp. 129-138 (2005).
NM_002651; Organism: Homo sapiens; "Homo sapiens phosphatidylinositol 4-kinase, catalytic, beta (PI4KB), transcript variant 1, mRNA"; PRI: Aug. 14, 2011.
Soutschek, et al.; "Therapeutic silencing of an endogenous gene by systemic administration of modified siRNAs"; Nature; 432:173-178 (2004).
Wang, et al.; "Phosphatidylinositol 4 Phosphate Regulates Targeting of Clathrin Adaptor AP-1 Complexes to the Golgi"; Cell; 114(3):299-310 (2003).
Elbashir,et al., Nature, 411:494-498 (2001).
Kraynack, et al., RNA, 12:163-176 (2006).
Written Opinion of the International Searching Authority for corresponding Application PCT/EP2008/058706 dated Jan. 5, 2010.
First Office Action for corresponding Chinese Application 2013100983361.
First Office Action for corresponding Chinese Application 200880023497.1 dated Oct. 17, 2011.
Second Office Action for corresponding Chinese Application 200880023497.1 dated Jul. 18, 2012.
Office Action for corresponding Japanese Application 2010514005 dated Mar. 5, 2013.
First Examination Report for corresponding India Application 503/DELNP/2010 dated Jul. 22, 2014.
First Examination Report for corresponding Australia Application 2008270209 dated May 19, 2011.
Examiner's Requisition for corresponding Canadian Application 2692503 dated Jun. 10, 2011.
Journal of Virology, Oct. 2009, vol. 83, No. 19, pp. 10058-10074.
Szivak, et al., "NM_002650.1", GenBank, 1-9, Nov. 17, 2006.
Zufferey R, et al., Self-inactivating lentivirus vector for safe and efficient in vivo gene delivery., J Virol., 72, 9873-80(1998).
Williams, D.J. et al.; Biochem. (1996) 35:14665-14670.
Wilson et al., 1988, Proc. Natl. Acad. Sci. USA 85:3014-3018.
Xia H et al. (2002), Nat. Biotech. 20: 1006-1010.
Yang, D., et al., Curr. Biol. (2000) 10:1191-1200.
Zufferey R, et al., Multiply attenuated lentiviral vector achieves efficient gene delivery in vivo., Nat. Biotechnol. 15, 871-85 (1997).
GenBank Accession No. U76561 submitted Oct. 28, 1996.
GenBank Accession No. NM_000732 (2015).
GenBank Accession No. NM_006139 (2014).

\* cited by examiner

A.
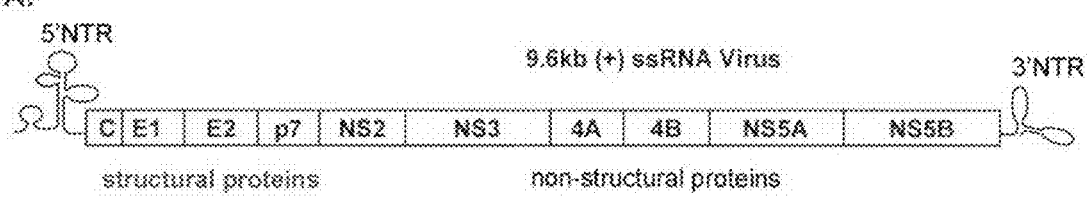
B.
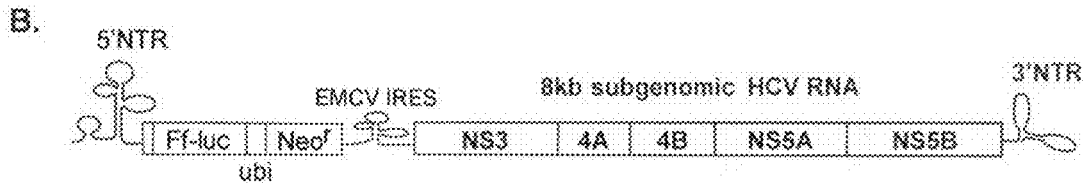
C.
Figure 1

Figure 6
D.
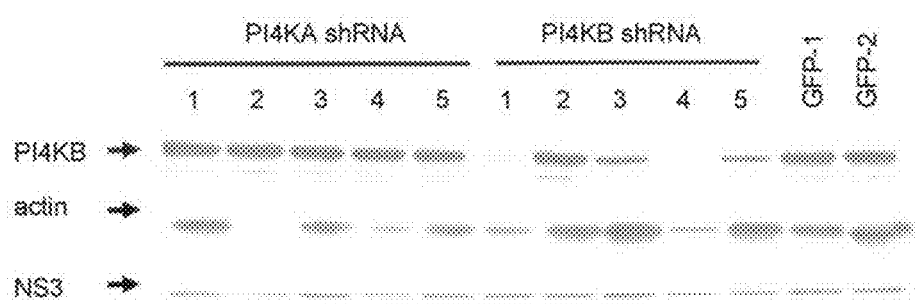
E.
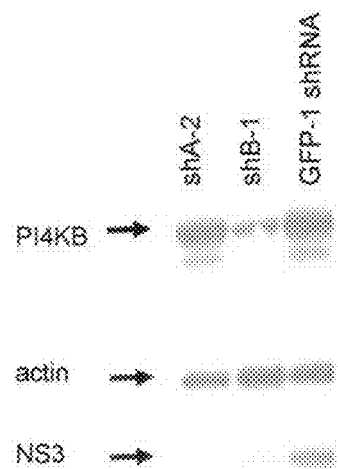

Figure 8
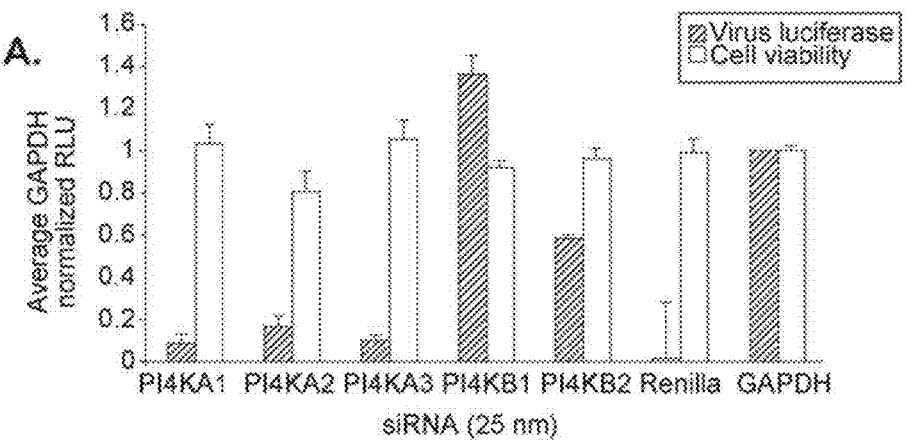
A.
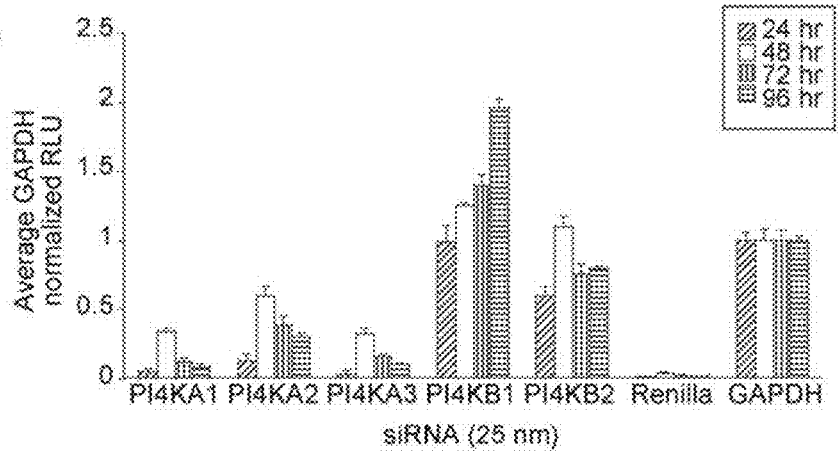
B.

SEQUENCE LISTING

```
<160> NUMBER OF SEQ ID NOS: 430

<210> SEQ ID NO 1
<211> LENGTH: 21
<212> TYPE: DNA
<213> ORGANISM: homo sapiens

<400> SEQUENCE: 1
ggacgugggu gaugccauuu u                                          21

<210> SEQ ID NO 2
<211> LENGTH: 21
<212> TYPE: DNA
<213> ORGANISM: homo sapiens

<400> SEQUENCE: 2
gggaugaccu ucggcaagau u                                          21

<210> SEQ ID NO 3
<211> LENGTH: 21
<212> TYPE: DNA
<213> ORGANISM: homo sapiens

<400> SEQUENCE: 3
gagauccguu gccuagaugu u                                          21
```

<210> SEQ ID NO 4
<211> LENGTH: 21
<212> TYPE: DNA
<213> ORGANISM: homo sapiens

<400> SEQUENCE: 4
gcaccgagag uauugauaau u                                              21

<210> SEQ ID NO 5
<211> LENGTH: 21
<212> TYPE: DNA
<213> ORGANISM: homo sapiens

<400> SEQUENCE: 5
uuaucaauac ucucggugct g                                              21

<210> SEQ ID NO 6
<211> LENGTH: 21
<212> TYPE: DNA
<213> ORGANISM: homo sapiens

<400> SEQUENCE: 6
uuguacucca ggcuccuugg a                                              21

<210> SEQ ID NO 7
<211> LENGTH: 21
<212> TYPE: DNA
<213> ORGANISM: homo sapiens

<400> SEQUENCE: 7
uuggacacug aggcauccgt t                                              21

<210> SEQ ID NO 8
<211> LENGTH: 21
<212> TYPE: DNA
<213> ORGANISM: homo sapiens

<400> SEQUENCE: 8
uagucaacca aguguaauct g                                              21

<210> SEQ ID NO 9
<211> LENGTH: 21
<212> TYPE: DNA
<213> ORGANISM: homo sapiens

<400> SEQUENCE: 9
uugggcacag ugcugaagct g                                              21

<210> SEQ ID NO 10
<211> LENGTH: 21
<212> TYPE: DNA
<213> ORGANISM: homo sapiens

<400> SEQUENCE: 10
auggguaaua ccacauucgg g                                              21

<210> SEQ ID NO 11
<211> LENGTH: 21
<212> TYPE: DNA
<213> ORGANISM: homo sapiens

<400> SEQUENCE: 11
aaucaugcca cuaucagccg a                                         21

<210> SEQ ID NO 12
<211> LENGTH: 21
<212> TYPE: DNA
<213> ORGANISM: homo sapiens

<400> SEQUENCE: 12
ucucguuuga aggcugucgg g                                         21

<210> SEQ ID NO 13
<211> LENGTH: 21
<212> TYPE: DNA
<213> ORGANISM: homo sapiens

<400> SEQUENCE: 13
uaccacauga uccuucgugt t                                         21

<210> SEQ ID NO 14
<211> LENGTH: 21
<212> TYPE: DNA
<213> ORGANISM: homo sapiens

<400> SEQUENCE: 14
uaaugcucug gcggcaacgg t                                         21

<210> SEQ ID NO 15
<211> LENGTH: 21
<212> TYPE: DNA
<213> ORGANISM: homo sapiens

<400> SEQUENCE: 15
aucuuguaug gcuugaucca a                                         21

<210> SEQ ID NO 16
<211> LENGTH: 21
<212> TYPE: DNA
<213> ORGANISM: homo sapiens

<400> SEQUENCE: 16
aucacaucca caaacucugt g                                         21

<210> SEQ ID NO 17
<211> LENGTH: 21
<212> TYPE: DNA
<213> ORGANISM: homo sapiens

<400> SEQUENCE: 17
uucuccacuu uaggguugct g                                         21

<210> SEQ ID NO 18
<211> LENGTH: 21
<212> TYPE: DNA
<213> ORGANISM: homo sapiens

<400> SEQUENCE: 18
ugucacauga ugccguuggt g                                         21

<210> SEQ ID NO 19
<211> LENGTH: 21
<212> TYPE: DNA
<213> ORGANISM: homo sapiens

<400> SEQUENCE: 19

| | |
|---|---|
| ugauagaccg cauacugcca t | 21 |

<210> SEQ ID NO 20
<211> LENGTH: 21
<212> TYPE: DNA
<213> ORGANISM: homo sapiens

<400> SEQUENCE: 20

| | |
|---|---|
| uuccgagcgg caaucagccc t | 21 |

<210> SEQ ID NO 21
<211> LENGTH: 21
<212> TYPE: DNA
<213> ORGANISM: homo sapiens

<400> SEQUENCE: 21

| | |
|---|---|
| uuucgaaugg ugcuggagcc a | 21 |

<210> SEQ ID NO 22
<211> LENGTH: 21
<212> TYPE: DNA
<213> ORGANISM: homo sapiens

<400> SEQUENCE: 22

| | |
|---|---|
| uguacauguu aagcaacugg g | 21 |

<210> SEQ ID NO 23
<211> LENGTH: 21
<212> TYPE: DNA
<213> ORGANISM: homo sapiens

<400> SEQUENCE: 23

| | |
|---|---|
| ucuacggacc ucguacuccg a | 21 |

<210> SEQ ID NO 24
<211> LENGTH: 21
<212> TYPE: DNA
<213> ORGANISM: homo sapiens

<400> SEQUENCE: 24

| | |
|---|---|
| uuccauuucc cuugggugga t | 21 |

<210> SEQ ID NO 25
<211> LENGTH: 21
<212> TYPE: DNA
<213> ORGANISM: homo sapiens

<400> SEQUENCE: 25

| | |
|---|---|
| uucucagaca agggcccuct a | 21 |

<210> SEQ ID NO 26
<211> LENGTH: 21
<212> TYPE: DNA
<213> ORGANISM: homo sapiens

<400> SEQUENCE: 26

| | |
|---|---|
| uugccgaucg ccaucaggga c | 21 |

<210> SEQ ID NO 27
<211> LENGTH: 21
<212> TYPE: DNA
<213> ORGANISM: homo sapiens

```
<400> SEQUENCE: 27
uggaucaucu aggcaacgga t                                              21

<210> SEQ ID NO 28
<211> LENGTH: 21
<212> TYPE: DNA
<213> ORGANISM: homo sapiens

<400> SEQUENCE: 28
uucccaaaug gacugcagut g                                              21

<210> SEQ ID NO 29
<211> LENGTH: 21
<212> TYPE: DNA
<213> ORGANISM: homo sapiens

<400> SEQUENCE: 29
uccacuacug uaucucccat g                                              21

<210> SEQ ID NO 30
<211> LENGTH: 21
<212> TYPE: DNA
<213> ORGANISM: homo sapiens

<400> SEQUENCE: 30
uaggaaguaa ucgagcaagg a                                              21

<210> SEQ ID NO 31
<211> LENGTH: 21
<212> TYPE: DNA
<213> ORGANISM: homo sapiens

<400> SEQUENCE: 31
aagaaucuca uucaauuucc a                                              21

<210> SEQ ID NO 32
<211> LENGTH: 21
<212> TYPE: DNA
<213> ORGANISM: homo sapiens

<400> SEQUENCE: 32
uagcuugguc ccacgggagt g                                              21

<210> SEQ ID NO 33
<211> LENGTH: 21
<212> TYPE: DNA
<213> ORGANISM: homo sapiens

<400> SEQUENCE: 33
uugaacaugu cgccauccag g                                              21

<210> SEQ ID NO 34
<211> LENGTH: 21
<212> TYPE: DNA
<213> ORGANISM: homo sapiens

<400> SEQUENCE: 34
ucaaguccua aguaccgaga a                                              21

<210> SEQ ID NO 35
<211> LENGTH: 21
<212> TYPE: DNA
<213> ORGANISM: homo sapiens
```

```
<400> SEQUENCE: 35
augacugaca ggagccgcca a                                              21

<210> SEQ ID NO 36
<211> LENGTH: 21
<212> TYPE: DNA
<213> ORGANISM: homo sapiens

<400> SEQUENCE: 36
uguucauccc ucuuagugge t                                              21

<210> SEQ ID NO 37
<211> LENGTH: 21
<212> TYPE: DNA
<213> ORGANISM: homo sapiens

<400> SEQUENCE: 37
uuggaguuga ggacaacagc c                                              21

<210> SEQ ID NO 38
<211> LENGTH: 21
<212> TYPE: DNA
<213> ORGANISM: homo sapiens

<400> SEQUENCE: 38
aauaagagga uggccugugg a                                              21

<210> SEQ ID NO 39
<211> LENGTH: 21
<212> TYPE: DNA
<213> ORGANISM: homo sapiens

<400> SEQUENCE: 39
ugauccgccg uacuuucucc t                                              21

<210> SEQ ID NO 40
<211> LENGTH: 21
<212> TYPE: DNA
<213> ORGANISM: homo sapiens

<400> SEQUENCE: 40
aauuccacau ggcuaggcca g                                              21

<210> SEQ ID NO 41
<211> LENGTH: 21
<212> TYPE: DNA
<213> ORGANISM: homo sapiens

<400> SEQUENCE: 41
aucugacuua gagcgcuggt g                                              21

<210> SEQ ID NO 42
<211> LENGTH: 21
<212> TYPE: DNA
<213> ORGANISM: homo sapiens

<400> SEQUENCE: 42
cucaguggug uaacugccgt g                                              21

<210> SEQ ID NO 43
<211> LENGTH: 21
<212> TYPE: DNA
```

<213> ORGANISM: homo sapiens

<400> SEQUENCE: 43
ucagcuuaaa ggcugacguc t                                              21

<210> SEQ ID NO 44
<211> LENGTH: 21
<212> TYPE: DNA
<213> ORGANISM: homo sapiens

<400> SEQUENCE: 44
aagccgucau agaguuuggt g                                              21

<210> SEQ ID NO 45
<211> LENGTH: 21
<212> TYPE: DNA
<213> ORGANISM: homo sapiens

<400> SEQUENCE: 45
uccgugauga cacuuagcag g                                              21

<210> SEQ ID NO 46
<211> LENGTH: 21
<212> TYPE: DNA
<213> ORGANISM: homo sapiens

<400> SEQUENCE: 46
ucgccuaugu cauccaccga c                                              21

<210> SEQ ID NO 47
<211> LENGTH: 21
<212> TYPE: DNA
<213> ORGANISM: homo sapiens

<400> SEQUENCE: 47
uggaaggccc gcccuucuca g                                              21

<210> SEQ ID NO 48
<211> LENGTH: 21
<212> TYPE: DNA
<213> ORGANISM: homo sapiens

<400> SEQUENCE: 48
aacugggaga uguugucaca g                                              21

<210> SEQ ID NO 49
<211> LENGTH: 21
<212> TYPE: DNA
<213> ORGANISM: homo sapiens

<400> SEQUENCE: 49
uagagacugc cacgccucca t                                              21

<210> SEQ ID NO 50
<211> LENGTH: 21
<212> TYPE: DNA
<213> ORGANISM: homo sapiens

<400> SEQUENCE: 50
uugaccacug guucaaucat g                                              21

<210> SEQ ID NO 51
<211> LENGTH: 21

<212> TYPE: DNA
<213> ORGANISM: homo sapiens

<400> SEQUENCE: 51
uuaggguugc uggcuguucg t            21

<210> SEQ ID NO 52
<211> LENGTH: 21
<212> TYPE: DNA
<213> ORGANISM: homo sapiens

<400> SEQUENCE: 52 ucuggguca gcuuaaaggc t            21

<210> SEQ ID NO 53
<211> LENGTH: 21
<212> TYPE: DNA
<213> ORGANISM: homo sapiens

<400> SEQUENCE: 53
auuaucaaua cucucggugc t            21

<210> SEQ ID NO 54
<211> LENGTH: 21
<212> TYPE: DNA
<213> ORGANISM: homo sapiens

<400> SEQUENCE: 54
uuggugaggu acuggaagcc g            21

<210> SEQ ID NO 55
<211> LENGTH: 21
<212> TYPE: DNA
<213> ORGANISM: homo sapiens

<400> SEQUENCE: 55
uguauggcuu gauccaaagg g            21

<210> SEQ ID NO 56
<211> LENGTH: 21
<212> TYPE: DNA
<213> ORGANISM: homo sapiens

<400> SEQUENCE: 56
uuggaguuau acagguauga a            21

<210> SEQ ID NO 57
<211> LENGTH: 21
<212> TYPE: DNA
<213> ORGANISM: homo sapiens

<400> SEQUENCE: 57
ucgagcuucc aagaaucuca t            21

<210> SEQ ID NO 58
<211> LENGTH: 21
<212> TYPE: DNA
<213> ORGANISM: homo sapiens

<400> SEQUENCE: 58
aaaguuaaug cucuggcggc a            21

<210> SEQ ID NO 59

```
<211> LENGTH: 21
<212> TYPE: DNA
<213> ORGANISM: homo sapiens

<400> SEQUENCE: 59
uaucagccga aaucacaaga a                                              21

<210> SEQ ID NO 60
<211> LENGTH: 21
<212> TYPE: DNA
<213> ORGANISM: homo sapiens

<400> SEQUENCE: 60
uugucauagu ugggcacagt g                                              21

<210> SEQ ID NO 61
<211> LENGTH: 21
<212> TYPE: DNA
<213> ORGANISM: homo sapiens

<400> SEQUENCE: 61
uccguagcuu ggucccacgg g                                              21

<210> SEQ ID NO 62
<211> LENGTH: 21
<212> TYPE: DNA
<213> ORGANISM: homo sapiens

<400> SEQUENCE: 62
ugagguuucg aauggugcug g                                              21

<210> SEQ ID NO 63
<211> LENGTH: 21
<212> TYPE: DNA
<213> ORGANISM: homo sapiens

<400> SEQUENCE: 63
uuguauggcu ugauccaaag g                                              21

<210> SEQ ID NO 64
<211> LENGTH: 21
<212> TYPE: DNA
<213> ORGANISM: homo sapiens

<400> SEQUENCE: 64
uaaguaccga gaaccuacuc t                                              21

<210> SEQ ID NO 65
<211> LENGTH: 21
<212> TYPE: DNA
<213> ORGANISM: homo sapiens

<400> SEQUENCE: 65
uuuccgagcg gcaaucagcc c                                              21

<210> SEQ ID NO 66
<211> LENGTH: 21
<212> TYPE: DNA
<213> ORGANISM: homo sapiens

<400> SEQUENCE: 66
ugagguacug gaagccguca t                                              21
```

```
<210> SEQ ID NO 67
<211> LENGTH: 21
<212> TYPE: DNA
<213> ORGANISM: homo sapiens

<400> SEQUENCE: 67
ucucagacaa gggcccucua g                                              21

<210> SEQ ID NO 68
<211> LENGTH: 21
<212> TYPE: DNA
<213> ORGANISM: homo sapiens

<400> SEQUENCE: 68
uguaggcuug uacuccaggc t                                              21

<210> SEQ ID NO 69
<211> LENGTH: 21
<212> TYPE: DNA
<213> ORGANISM: homo sapiens

<400> SEQUENCE: 69
uuaaugcucu ggcggcaacg g                                              21

<210> SEQ ID NO 70
<211> LENGTH: 21
<212> TYPE: DNA
<213> ORGANISM: homo sapiens

<400> SEQUENCE: 70
gaauuaucaa uacucucggt g                                              21

<210> SEQ ID NO 71
<211> LENGTH: 21
<212> TYPE: DNA
<213> ORGANISM: homo sapiens

<400> SEQUENCE: 71
uuccacaugg cuaggccagt a                                              21

<210> SEQ ID NO 72
<211> LENGTH: 21
<212> TYPE: DNA
<213> ORGANISM: homo sapiens

<400> SEQUENCE: 72
ugaggcaucc guucauacct c                                              21

<210> SEQ ID NO 73
<211> LENGTH: 21
<212> TYPE: DNA
<213> ORGANISM: homo sapiens

<400> SEQUENCE: 73
uugcuggcug uucguuucag g                                              21

<210> SEQ ID NO 74
<211> LENGTH: 21
<212> TYPE: DNA
<213> ORGANISM: homo sapiens

<400> SEQUENCE: 74
aacaugucgc cauccaggcc g                                              21
```

```
<210> SEQ ID NO 75
<211> LENGTH: 21
<212> TYPE: DNA
<213> ORGANISM: homo sapiens

<400> SEQUENCE: 75
ugcuccggag uagucaacca a                                              21

<210> SEQ ID NO 76
<211> LENGTH: 21
<212> TYPE: DNA
<213> ORGANISM: homo sapiens

<400> SEQUENCE: 76
acugguucaa ucaugccact a                                              21

<210> SEQ ID NO 77
<211> LENGTH: 21
<212> TYPE: DNA
<213> ORGANISM: homo sapiens

<400> SEQUENCE: 77
uagaccgcau acugccaucc a                                              21

<210> SEQ ID NO 78
<211> LENGTH: 21
<212> TYPE: DNA
<213> ORGANISM: homo sapiens

<400> SEQUENCE: 78
uggaguugag gacaacagcc t                                              21

<210> SEQ ID NO 79
<211> LENGTH: 21
<212> TYPE: DNA
<213> ORGANISM: homo sapiens

<400> SEQUENCE: 79
uaguugggca cagugcugaa g                                              21

<210> SEQ ID NO 80
<211> LENGTH: 21
<212> TYPE: DNA
<213> ORGANISM: homo sapiens

<400> SEQUENCE: 80
ucaauacucu cggugcugga g                                              21

<210> SEQ ID NO 81
<211> LENGTH: 21
<212> TYPE: DNA
<213> ORGANISM: homo sapiens

<400> SEQUENCE: 81
uacuccgaau ucgguucucg g                                              21

<210> SEQ ID NO 82
<211> LENGTH: 21
<212> TYPE: DNA
<213> ORGANISM: homo sapiens

<400> SEQUENCE: 82
uuaccacaug auccuucgug t                                              21
```

```
<210> SEQ ID NO 83
<211> LENGTH: 21
<212> TYPE: DNA
<213> ORGANISM: homo sapiens

<400> SEQUENCE: 83
uggcuaggcc aguacccuca g                                              21

<210> SEQ ID NO 84
<211> LENGTH: 21
<212> TYPE: DNA
<213> ORGANISM: homo sapiens

<400> SEQUENCE: 84
uucuacggac cucguacucc g                                              21

<210> SEQ ID NO 85
<211> LENGTH: 21
<212> TYPE: DNA
<213> ORGANISM: homo sapiens

<400> SEQUENCE: 85
ugacaggagc cgccaauugg g                                              21

<210> SEQ ID NO 86
<211> LENGTH: 21
<212> TYPE: DNA
<213> ORGANISM: homo sapiens

<400> SEQUENCE: 86
ucagacaagg gcccucuagg g                                              21

<210> SEQ ID NO 87
<211> LENGTH: 21
<212> TYPE: DNA
<213> ORGANISM: homo sapiens

<400> SEQUENCE: 87
auugaccacu gguucaauca t                                              21

<210> SEQ ID NO 88
<211> LENGTH: 21
<212> TYPE: DNA
<213> ORGANISM: homo sapiens

<400> SEQUENCE: 88
uccggaguag ucaaccaagt g                                              21

<210> SEQ ID NO 89
<211> LENGTH: 21
<212> TYPE: DNA
<213> ORGANISM: homo sapiens

<400> SEQUENCE: 89
ucauggguaa uaccacauuc g                                              21

<210> SEQ ID NO 90
<211> LENGTH: 21
<212> TYPE: DNA
<213> ORGANISM: homo sapiens

<400> SEQUENCE: 90
```
uucaaucaug ccacuaucag c                                            21

<210> SEQ ID NO 91
<211> LENGTH: 21
<212> TYPE: DNA
<213> ORGANISM: homo sapiens

<400> SEQUENCE: 91
ucuaggcaac ggaucucact g                                            21

<210> SEQ ID NO 92
<211> LENGTH: 21
<212> TYPE: DNA
<213> ORGANISM: homo sapiens

<400> SEQUENCE: 92 ugaucgggc agguggauca t                                             21

<210> SEQ ID NO 93
<211> LENGTH: 21
<212> TYPE: DNA
<213> ORGANISM: homo sapiens

<400> SEQUENCE: 93
uaucaauacu cucggugcug g                                            21

<210> SEQ ID NO 94
<211> LENGTH: 21
<212> TYPE: DNA
<213> ORGANISM: homo sapiens

<400> SEQUENCE: 94
aaugcucugg cggcaacggt g                                            21

<210> SEQ ID NO 95
<211> LENGTH: 21
<212> TYPE: DNA
<213> ORGANISM: homo sapiens

<400> SEQUENCE: 95
ucccacggga gugucguuga g                                            21

<210> SEQ ID NO 96
<211> LENGTH: 21
<212> TYPE: DNA
<213> ORGANISM: homo sapiens

<400> SEQUENCE: 96
uuucucagac aagggcccuc t                                            21

<210> SEQ ID NO 97
<211> LENGTH: 21
<212> TYPE: DNA
<213> ORGANISM: homo sapiens

<400> SEQUENCE: 97
aucuucuggg ucucguuuga a                                            21

<210> SEQ ID NO 98
<211> LENGTH: 21
<212> TYPE: DNA
<213> ORGANISM: homo sapiens

<400> SEQUENCE: 98

-continued ucguacuccg aauucgguuc t                                             21

<210> SEQ ID NO 99
<211> LENGTH: 21
<212> TYPE: DNA
<213> ORGANISM: homo sapiens

<400> SEQUENCE: 99
uuuaggguug cuggcuguuc g                                             21

<210> SEQ ID NO 100
<211> LENGTH: 21
<212> TYPE: DNA
<213> ORGANISM: homo sapiens

<400> SEQUENCE: 100
cuccuguagg aaguaaucga g                                             21

<210> SEQ ID NO 101
<211> LENGTH: 21
<212> TYPE: DNA
<213> ORGANISM: homo sapiens

<400> SEQUENCE: 101
uggugaggua cuggaagccg t                                             21

<210> SEQ ID NO 102
<211> LENGTH: 21
<212> TYPE: DNA
<213> ORGANISM: homo sapiens

<400> SEQUENCE: 102
ucauccaccg accaggccuc a                                             21

<210> SEQ ID NO 103
<211> LENGTH: 21
<212> TYPE: DNA
<213> ORGANISM: homo sapiens

<400> SEQUENCE: 103
acuccgaauu cgguucucgg g                                             21

<210> SEQ ID NO 104
<211> LENGTH: 21
<212> TYPE: DNA
<213> ORGANISM: homo sapiens

<400> SEQUENCE: 104
ucagguaggg agccuugucc t                                             21

<210> SEQ ID NO 105
<211> LENGTH: 23
<212> TYPE: DNA
<213> ORGANISM: homo sapiens

<400> SEQUENCE: 105
aaaauggcau cacccacguc ctt                                           23

<210> SEQ ID NO 106
<211> LENGTH: 23
<212> TYPE: DNA
<213> ORGANISM: homo sapiens

```
<400> SEQUENCE: 106
aaucuugccg aaggucaucc ctt                                        23

<210> SEQ ID NO 107
<211> LENGTH: 23
<212> TYPE: DNA
<213> ORGANISM: homo sapiens

<400> SEQUENCE: 107
aacaucuagg caacggaucu ctt                                        23

<210> SEQ ID NO 108
<211> LENGTH: 23
<212> TYPE: DNA
<213> ORGANISM: homo sapiens

<400> SEQUENCE: 108
aauuaucaau acucucggug ctt                                        23

<210> SEQ ID NO 109
<211> LENGTH: 21
<212> TYPE: DNA
<213> ORGANISM: homo sapiens

<400> SEQUENCE: 109
gcaccgagag uauugauaat t                                          21

<210> SEQ ID NO 110
<211> LENGTH: 21
<212> TYPE: DNA
<213> ORGANISM: homo sapiens

<400> SEQUENCE: 110
caaggagccu ggaguacaat t                                          21

<210> SEQ ID NO 111
<211> LENGTH: 21
<212> TYPE: DNA
<213> ORGANISM: homo sapiens

<400> SEQUENCE: 111
cggaugccuc aguguccaat t                                          21

<210> SEQ ID NO 112
<211> LENGTH: 21
<212> TYPE: DNA
<213> ORGANISM: homo sapiens

<400> SEQUENCE: 112
gauuacacuu gguugacuat t                                          21

<210> SEQ ID NO 113
<211> LENGTH: 21
<212> TYPE: DNA
<213> ORGANISM: homo sapiens

<400> SEQUENCE: 113
gcuucagcac ugugcccaat t                                          21

<210> SEQ ID NO 114
<211> LENGTH: 21
<212> TYPE: DNA
<213> ORGANISM: homo sapiens
```

```
<400> SEQUENCE: 114
cgaauguggu auuacccaut t                                              21

<210> SEQ ID NO 115
<211> LENGTH: 21
<212> TYPE: DNA
<213> ORGANISM: homo sapiens

<400> SEQUENCE: 115
ggcugauagu ggcaugauut t                                              21

<210> SEQ ID NO 116
<211> LENGTH: 21
<212> TYPE: DNA
<213> ORGANISM: homo sapiens

<400> SEQUENCE: 116
cgacagccuu caaacgagat t                                              21

<210> SEQ ID NO 117
<211> LENGTH: 21
<212> TYPE: DNA
<213> ORGANISM: homo sapiens

<400> SEQUENCE: 117
cacgaaggau caugugguat t                                              21

<210> SEQ ID NO 118
<211> LENGTH: 21
<212> TYPE: DNA
<213> ORGANISM: homo sapiens

<400> SEQUENCE: 118
cguugccgcc agagcauuat t                                              21

<210> SEQ ID NO 119
<211> LENGTH: 21
<212> TYPE: DNA
<213> ORGANISM: homo sapiens

<400> SEQUENCE: 119
ggaucaagcc auacaagaut t                                              21

<210> SEQ ID NO 120
<211> LENGTH: 21
<212> TYPE: DNA
<213> ORGANISM: homo sapiens

<400> SEQUENCE: 120
cagaguuugu ggaugugaut t                                              21

<210> SEQ ID NO 121
<211> LENGTH: 21
<212> TYPE: DNA
<213> ORGANISM: homo sapiens

<400> SEQUENCE: 121
gcaacccuaa aguggagaat t                                              21

<210> SEQ ID NO 122
<211> LENGTH: 21
<212> TYPE: DNA
```

```
<213> ORGANISM: homo sapiens

<400> SEQUENCE: 122
ccaacggcau caugugacat t                                              21

<210> SEQ ID NO 123
<211> LENGTH: 21
<212> TYPE: DNA
<213> ORGANISM: homo sapiens

<400> SEQUENCE: 123
ggcaguaugc ggucuaucat t                                              21

<210> SEQ ID NO 124
<211> LENGTH: 21
<212> TYPE: DNA
<213> ORGANISM: homo sapiens

<400> SEQUENCE: 124
ggcugauugc cgcucggaat t                                              21

<210> SEQ ID NO 125
<211> LENGTH: 21
<212> TYPE: DNA
<213> ORGANISM: homo sapiens

<400> SEQUENCE: 125
gcuccagcac cauucgaaat t                                              21

<210> SEQ ID NO 126
<211> LENGTH: 21
<212> TYPE: DNA
<213> ORGANISM: homo sapiens

<400> SEQUENCE: 126
caguugcuua acauguacat t                                              21

<210> SEQ ID NO 127
<211> LENGTH: 21
<212> TYPE: DNA
<213> ORGANISM: homo sapiens

<400> SEQUENCE: 127
ggaguacgag guccguagat t                                              21

<210> SEQ ID NO 128
<211> LENGTH: 21
<212> TYPE: DNA
<213> ORGANISM: homo sapiens

<400> SEQUENCE: 128
ccacccaagg gaaauggaat t                                              21

<210> SEQ ID NO 129
<211> LENGTH: 21
<212> TYPE: DNA
<213> ORGANISM: homo sapiens

<400> SEQUENCE: 129
gagggcccuu gucugagaat t                                              21

<210> SEQ ID NO 130
<211> LENGTH: 21
```

<212> TYPE: DNA
<213> ORGANISM: homo sapiens

<400> SEQUENCE: 130
cccugauggc gaucggcaat t                                        21

<210> SEQ ID NO 131
<211> LENGTH: 21
<212> TYPE: DNA
<213> ORGANISM: homo sapiens

<400> SEQUENCE: 131
ccguugccua gaugauccat t                                        21

<210> SEQ ID NO 132
<211> LENGTH: 21
<212> TYPE: DNA
<213> ORGANISM: homo sapiens

<400> SEQUENCE: 132
acugcagucc auuugggaat t                                        21

<210> SEQ ID NO 133
<211> LENGTH: 21
<212> TYPE: DNA
<213> ORGANISM: homo sapiens

<400> SEQUENCE: 133
ugggagauac aguaguggat t                                        21

<210> SEQ ID NO 134
<211> LENGTH: 21
<212> TYPE: DNA
<213> ORGANISM: homo sapiens

<400> SEQUENCE: 134
cuugcucgau uacuuccuat t                                        21

<210> SEQ ID NO 135
<211> LENGTH: 21
<212> TYPE: DNA
<213> ORGANISM: homo sapiens

<400> SEQUENCE: 135
gaaauugaau gagauucuut t                                        21

<210> SEQ ID NO 136
<211> LENGTH: 21
<212> TYPE: DNA
<213> ORGANISM: homo sapiens

<400> SEQUENCE: 136
cucccguggg accaagcuat t                                        21

<210> SEQ ID NO 137
<211> LENGTH: 21
<212> TYPE: DNA
<213> ORGANISM: homo sapiens

<400> SEQUENCE: 137
uggauggcga cauguucaat t                                        21

<210> SEQ ID NO 138

<211> LENGTH: 21
<212> TYPE: DNA
<213> ORGANISM: homo sapiens

<400> SEQUENCE: 138
cucgguacuu aggacuugat t                                              21

<210> SEQ ID NO 139
<211> LENGTH: 21
<212> TYPE: DNA
<213> ORGANISM: homo sapiens

<400> SEQUENCE: 139
ggcggcuccu gucagucaut t                                              21

<210> SEQ ID NO 140
<211> LENGTH: 21
<212> TYPE: DNA
<213> ORGANISM: homo sapiens

<400> SEQUENCE: 140
ccacuaagag ggaugaacat t                                              21

<210> SEQ ID NO 141
<211> LENGTH: 21
<212> TYPE: DNA
<213> ORGANISM: homo sapiens

<400> SEQUENCE: 141
cuguuguccu caacuccaat t                                              21

<210> SEQ ID NO 142
<211> LENGTH: 21
<212> TYPE: DNA
<213> ORGANISM: homo sapiens

<400> SEQUENCE: 142
cacaggccau ccucuuauut t                                              21

<210> SEQ ID NO 143
<211> LENGTH: 21
<212> TYPE: DNA
<213> ORGANISM: homo sapiens

<400> SEQUENCE: 143
gagaaaguac ggcggaucat t                                              21

<210> SEQ ID NO 144
<211> LENGTH: 21
<212> TYPE: DNA
<213> ORGANISM: homo sapiens

<400> SEQUENCE: 144
ggccuagcca uguggaauut t                                              21

<210> SEQ ID NO 145
<211> LENGTH: 21
<212> TYPE: DNA
<213> ORGANISM: homo sapiens

<400> SEQUENCE: 145
ccagcgcucu aagucagaut t                                              21

-continued

```
<210> SEQ ID NO 146
<211> LENGTH: 21
<212> TYPE: DNA
<213> ORGANISM: homo sapiens

<400> SEQUENCE: 146
cggcaguuac accacugagt t                                              21

<210> SEQ ID NO 147
<211> LENGTH: 21
<212> TYPE: DNA
<213> ORGANISM: homo sapiens

<400> SEQUENCE: 147
acgucagccu uuaagcugat t                                              21

<210> SEQ ID NO 148
<211> LENGTH: 21
<212> TYPE: DNA
<213> ORGANISM: homo sapiens

<400> SEQUENCE: 148
ccaaacucua ugacggcuut t                                              21

<210> SEQ ID NO 149
<211> LENGTH: 21
<212> TYPE: DNA
<213> ORGANISM: homo sapiens

<400> SEQUENCE: 149
ugcuaagugu caucacggat t                                              21

<210> SEQ ID NO 150
<211> LENGTH: 21
<212> TYPE: DNA
<213> ORGANISM: homo sapiens

<400> SEQUENCE: 150
cgguggauga cauaggcgat t                                              21

<210> SEQ ID NO 151
<211> LENGTH: 21
<212> TYPE: DNA
<213> ORGANISM: homo sapiens

<400> SEQUENCE: 151
gagaagggcg ggccuuccat t                                              21

<210> SEQ ID NO 152
<211> LENGTH: 21
<212> TYPE: DNA
<213> ORGANISM: homo sapiens

<400> SEQUENCE: 152
gugacaacau cucccaguut t                                              21

<210> SEQ ID NO 153
<211> LENGTH: 21
<212> TYPE: DNA
<213> ORGANISM: homo sapiens

<400> SEQUENCE: 153
ggaggcgugg cagucucuat t                                              21
```

```
<210> SEQ ID NO 154
<211> LENGTH: 21
<212> TYPE: DNA
<213> ORGANISM: homo sapiens

<400> SEQUENCE: 154
ugauugaacc aguggucaat t                                              21

<210> SEQ ID NO 155
<211> LENGTH: 21
<212> TYPE: DNA
<213> ORGANISM: homo sapiens

<400> SEQUENCE: 155
gaacagccag caacccuaat t                                              21

<210> SEQ ID NO 156
<211> LENGTH: 21
<212> TYPE: DNA
<213> ORGANISM: homo sapiens

<400> SEQUENCE: 156
ccuuuaagcu gaccacagat t                                              21

<210> SEQ ID NO 157
<211> LENGTH: 21
<212> TYPE: DNA
<213> ORGANISM: homo sapiens

<400> SEQUENCE: 157
caccgagagu auugauaaut t                                              21

<210> SEQ ID NO 158
<211> LENGTH: 21
<212> TYPE: DNA
<213> ORGANISM: homo sapiens

<400> SEQUENCE: 158
gcuuccagua ccucaccaat t                                              21

<210> SEQ ID NO 159
<211> LENGTH: 21
<212> TYPE: DNA
<213> ORGANISM: homo sapiens

<400> SEQUENCE: 159
cuuuggauca agccauacat t                                              21

<210> SEQ ID NO 160
<211> LENGTH: 21
<212> TYPE: DNA
<213> ORGANISM: homo sapiens

<400> SEQUENCE: 160
cauaccugua uaacuccaat t                                              21

<210> SEQ ID NO 161
<211> LENGTH: 21
<212> TYPE: DNA
<213> ORGANISM: homo sapiens

<400> SEQUENCE: 161
gagauucuug gaagcucgat t                                              21
```

```
<210> SEQ ID NO 162
<211> LENGTH: 21
<212> TYPE: DNA
<213> ORGANISM: homo sapiens

<400> SEQUENCE: 162
ccgccagagc auuaacuuut t                                              21

<210> SEQ ID NO 163
<211> LENGTH: 21
<212> TYPE: DNA
<213> ORGANISM: homo sapiens

<400> SEQUENCE: 163
cuugugauuu cggcugauat t                                              21

<210> SEQ ID NO 164
<211> LENGTH: 21
<212> TYPE: DNA
<213> ORGANISM: homo sapiens

<400> SEQUENCE: 164
cugugcccaa cuaugacaat t                                              21

<210> SEQ ID NO 165
<211> LENGTH: 21
<212> TYPE: DNA
<213> ORGANISM: homo sapiens

<400> SEQUENCE: 165
cgugggacca agcuacggat t                                              21

<210> SEQ ID NO 166
<211> LENGTH: 21
<212> TYPE: DNA
<213> ORGANISM: homo sapiens

<400> SEQUENCE: 166
agcaccauuc gaaaccucat t                                              21

<210> SEQ ID NO 167
<211> LENGTH: 21
<212> TYPE: DNA
<213> ORGANISM: homo sapiens

<400> SEQUENCE: 167
uuuggaucaa gccauacaat t                                              21

<210> SEQ ID NO 168
<211> LENGTH: 21
<212> TYPE: DNA
<213> ORGANISM: homo sapiens

<400> SEQUENCE: 168
aguagguucu cgguacuuat t                                              21

<210> SEQ ID NO 169
<211> LENGTH: 21
<212> TYPE: DNA
<213> ORGANISM: homo sapiens

<400> SEQUENCE: 169
```

```
gcugauugcc gcucggaaat t                                              21

<210> SEQ ID NO 170
<211> LENGTH: 21
<212> TYPE: DNA
<213> ORGANISM: homo sapiens

<400> SEQUENCE: 170
gacggcuucc aguaccucat t                                              21

<210> SEQ ID NO 171
<211> LENGTH: 21
<212> TYPE: DNA
<213> ORGANISM: homo sapiens

<400> SEQUENCE: 171
agagggcccu ugucugagat t                                              21

<210> SEQ ID NO 172
<211> LENGTH: 21
<212> TYPE: DNA
<213> ORGANISM: homo sapiens

<400> SEQUENCE: 172
ccuggaguac aagccuacat t                                              21

<210> SEQ ID NO 173
<211> LENGTH: 21
<212> TYPE: DNA
<213> ORGANISM: homo sapiens

<400> SEQUENCE: 173
guugccgcca gagcauuaat t                                              21

<210> SEQ ID NO 174
<211> LENGTH: 21
<212> TYPE: DNA
<213> ORGANISM: homo sapiens

<400> SEQUENCE: 174
ccgagaguau ugauaauuct t                                              21

<210> SEQ ID NO 175
<211> LENGTH: 21
<212> TYPE: DNA
<213> ORGANISM: homo sapiens

<400> SEQUENCE: 175
cuggccuagc cauguggaat t                                              21

<210> SEQ ID NO 176
<211> LENGTH: 21
<212> TYPE: DNA
<213> ORGANISM: homo sapiens

<400> SEQUENCE: 176
gguaugaacg gaugccucat t                                              21

<210> SEQ ID NO 177
<211> LENGTH: 21
<212> TYPE: DNA
<213> ORGANISM: homo sapiens

<400> SEQUENCE: 177
```
ugaaacgaac agccagcaat t    21

<210> SEQ ID NO 178
<211> LENGTH: 21
<212> TYPE: DNA
<213> ORGANISM: homo sapiens

<400> SEQUENCE: 178
gccuggaugg cgacauguut t    21

<210> SEQ ID NO 179
<211> LENGTH: 21
<212> TYPE: DNA
<213> ORGANISM: homo sapiens

<400> SEQUENCE: 179
gguugacuac uccggagcat t    21

<210> SEQ ID NO 180
<211> LENGTH: 21
<212> TYPE: DNA
<213> ORGANISM: homo sapiens

<400> SEQUENCE: 180
guggcaugau ugaaccagut t    21

<210> SEQ ID NO 181
<211> LENGTH: 21
<212> TYPE: DNA
<213> ORGANISM: homo sapiens

<400> SEQUENCE: 181
gauggcagua ugcggucuat t    21

<210> SEQ ID NO 182
<211> LENGTH: 21
<212> TYPE: DNA
<213> ORGANISM: homo sapiens

<400> SEQUENCE: 182
gcuguugucc ucaacuccat t    21

<210> SEQ ID NO 183
<211> LENGTH: 21
<212> TYPE: DNA
<213> ORGANISM: homo sapiens

<400> SEQUENCE: 183
ucagcacugu gcccaacuat t    21

<210> SEQ ID NO 184
<211> LENGTH: 21
<212> TYPE: DNA
<213> ORGANISM: homo sapiens

<400> SEQUENCE: 184
ccagcaccga gaguauugat t    21

<210> SEQ ID NO 185
<211> LENGTH: 21
<212> TYPE: DNA
<213> ORGANISM: homo sapiens

<400> SEQUENCE: 185
gagaaccgaa uucggaguat t                                                    21

<210> SEQ ID NO 186
<211> LENGTH: 21
<212> TYPE: DNA
<213> ORGANISM: homo sapiens

<400> SEQUENCE: 186
acgaaggauc augugguaat t                                                    21

<210> SEQ ID NO 187
<211> LENGTH: 21
<212> TYPE: DNA
<213> ORGANISM: homo sapiens

<400> SEQUENCE: 187
gaggguacug gccuagccat t                                                    21

<210> SEQ ID NO 188
<211> LENGTH: 21
<212> TYPE: DNA
<213> ORGANISM: homo sapiens

<400> SEQUENCE: 188
gaguacgagg uccguagaat t                                                    21

<210> SEQ ID NO 189
<211> LENGTH: 21
<212> TYPE: DNA
<213> ORGANISM: homo sapiens

<400> SEQUENCE: 189
caauuggcgg cuccugucat t                                                    21

<210> SEQ ID NO 190
<211> LENGTH: 21
<212> TYPE: DNA
<213> ORGANISM: homo sapiens

<400> SEQUENCE: 190
cuagagggcc cuugucugat t                                                    21

<210> SEQ ID NO 191
<211> LENGTH: 21
<212> TYPE: DNA
<213> ORGANISM: homo sapiens

<400> SEQUENCE: 191
gauugaacca guggucaaut t                                                    21

<210> SEQ ID NO 192
<211> LENGTH: 21
<212> TYPE: DNA
<213> ORGANISM: homo sapiens

<400> SEQUENCE: 192
cuugguugac uacuccggat t                                                    21

<210> SEQ ID NO 193
<211> LENGTH: 21
<212> TYPE: DNA
<213> ORGANISM: homo sapiens

```
<400> SEQUENCE: 193 aauguggu au uacccaugat t                                            21

<210> SEQ ID NO 194
<211> LENGTH: 21
<212> TYPE: DNA
<213> ORGANISM: homo sapiens

<400> SEQUENCE: 194 ugauagug gc augauugaat t                                            21

<210> SEQ ID NO 195
<211> LENGTH: 21
<212> TYPE: DNA
<213> ORGANISM: homo sapiens

<400> SEQUENCE: 195
gugagauccg uugccuagat t                                             21

<210> SEQ ID NO 196
<211> LENGTH: 21
<212> TYPE: DNA
<213> ORGANISM: homo sapiens

<400> SEQUENCE: 196
gauccaccug cccagaucat t                                             21

<210> SEQ ID NO 197
<211> LENGTH: 21
<212> TYPE: DNA
<213> ORGANISM: homo sapiens

<400> SEQUENCE: 197
agcaccgaga guauugauat t                                             21

<210> SEQ ID NO 198
<211> LENGTH: 21
<212> TYPE: DNA
<213> ORGANISM: homo sapiens

<400> SEQUENCE: 198
ccguugccgc cagagcauut t                                             21

<210> SEQ ID NO 199
<211> LENGTH: 21
<212> TYPE: DNA
<213> ORGANISM: homo sapiens

<400> SEQUENCE: 199
caacgacacu cccgugggat t                                             21

<210> SEQ ID NO 200
<211> LENGTH: 21
<212> TYPE: DNA
<213> ORGANISM: homo sapiens

<400> SEQUENCE: 200
agggcccuug ucugagaaat t                                             21

<210> SEQ ID NO 201
<211> LENGTH: 21
<212> TYPE: DNA
```

<213> ORGANISM: homo sapiens

<400> SEQUENCE: 201
caaacgagac ccagaagaut t                                              21

<210> SEQ ID NO 202
<211> LENGTH: 21
<212> TYPE: DNA
<213> ORGANISM: homo sapiens

<400> SEQUENCE: 202
aaccgaauuc ggaguacgat t                                              21

<210> SEQ ID NO 203
<211> LENGTH: 21
<212> TYPE: DNA
<213> ORGANISM: homo sapiens

<400> SEQUENCE: 203
aacagccagc aacccuaaat t                                              21

<210> SEQ ID NO 204
<211> LENGTH: 21
<212> TYPE: DNA
<213> ORGANISM: homo sapiens

<400> SEQUENCE: 204
cgauuacuuc cuacaggagt t                                              21

<210> SEQ ID NO 205
<211> LENGTH: 21
<212> TYPE: DNA
<213> ORGANISM: homo sapiens

<400> SEQUENCE: 205
ggcuuccagu accucaccat t                                              21

<210> SEQ ID NO 206
<211> LENGTH: 21
<212> TYPE: DNA
<213> ORGANISM: homo sapiens

<400> SEQUENCE: 206
aggccugguc gguggaugat t                                              21

<210> SEQ ID NO 207
<211> LENGTH: 21
<212> TYPE: DNA
<213> ORGANISM: homo sapiens

<400> SEQUENCE: 207
cgagaaccga auucggagut t                                              21

<210> SEQ ID NO 208
<211> LENGTH: 21
<212> TYPE: DNA
<213> ORGANISM: homo sapiens

<400> SEQUENCE: 208
gacaaggcuc ccuaccugat t                                              21

<210> SEQ ID NO 209
<211> LENGTH: 21

```
<212> TYPE: DNA
<213> ORGANISM: homo sapiens

<400> SEQUENCE: 209
gagcaucucu cccuaccuau u                                              21

<210> SEQ ID NO 210
<211> LENGTH: 21
<212> TYPE: DNA
<213> ORGANISM: homo sapiens

<400> SEQUENCE: 210
gugaagcgau guggaguuau u                                              21

<210> SEQ ID NO 211
<211> LENGTH: 21
<212> TYPE: DNA
<213> ORGANISM: homo sapiens

<400> SEQUENCE: 211
ccacaggccu cuccuacuuu u                                              21

<210> SEQ ID NO 212
<211> LENGTH: 21
<212> TYPE: DNA
<213> ORGANISM: homo sapiens

<400> SEQUENCE: 212
gcagaaauuu ggccuguuuu u                                              21

<210> SEQ ID NO 213
<211> LENGTH: 21
<212> TYPE: DNA
<213> ORGANISM: homo sapiens

<400> SEQUENCE: 213
uucuuaucug agaacauggc g                                              21

<210> SEQ ID NO 214
<211> LENGTH: 21
<212> TYPE: DNA
<213> ORGANISM: homo sapiens

<400> SEQUENCE: 214
uuuggguuga cuugcuuccg a                                              21

<210> SEQ ID NO 215
<211> LENGTH: 21
<212> TYPE: DNA
<213> ORGANISM: homo sapiens

<400> SEQUENCE: 215
uagaagagga uggcguccgg a                                              21

<210> SEQ ID NO 216
<211> LENGTH: 21
<212> TYPE: DNA
<213> ORGANISM: homo sapiens

<400> SEQUENCE: 216
uauguguuga uccagccuug g                                              21

<210> SEQ ID NO 217
```

```
<211> LENGTH: 21
<212> TYPE: DNA
<213> ORGANISM: homo sapiens

<400> SEQUENCE: 217
uugaacuugg ccagauaugg g                                              21

<210> SEQ ID NO 218
<211> LENGTH: 21
<212> TYPE: DNA
<213> ORGANISM: homo sapiens

<400> SEQUENCE: 218
augauagccg acacguuggt g                                              21

<210> SEQ ID NO 219
<211> LENGTH: 21
<212> TYPE: DNA
<213> ORGANISM: homo sapiens

<400> SEQUENCE: 219
uucaggcaca ucacuaacgg c                                              21

<210> SEQ ID NO 220
<211> LENGTH: 21
<212> TYPE: DNA
<213> ORGANISM: homo sapiens

<400> SEQUENCE: 220
uucggaugaa guuguagcgg g                                              21

<210> SEQ ID NO 221
<211> LENGTH: 21
<212> TYPE: DNA
<213> ORGANISM: homo sapiens

<400> SEQUENCE: 221
uucaaguuca cuaacuccac a                                              21

<210> SEQ ID NO 222
<211> LENGTH: 21
<212> TYPE: DNA
<213> ORGANISM: homo sapiens

<400> SEQUENCE: 222
ucauccucgg agucugagcg g                                              21

<210> SEQ ID NO 223
<211> LENGTH: 21
<212> TYPE: DNA
<213> ORGANISM: homo sapiens

<400> SEQUENCE: 223
uuucugcucc accgucaugt g                                              21

<210> SEQ ID NO 224
<211> LENGTH: 21
<212> TYPE: DNA
<213> ORGANISM: homo sapiens

<400> SEQUENCE: 224
aggaauguua gcuccucugt g                                              21
```

```
<210> SEQ ID NO 225
<211> LENGTH: 21
<212> TYPE: DNA
<213> ORGANISM: homo sapiens

<400> SEQUENCE: 225
aaguagucaa aggcagugga g                                              21

<210> SEQ ID NO 226
<211> LENGTH: 21
<212> TYPE: DNA
<213> ORGANISM: homo sapiens

<400> SEQUENCE: 226
uucacuucag acagggccga c                                              21

<210> SEQ ID NO 227
<211> LENGTH: 21
<212> TYPE: DNA
<213> ORGANISM: homo sapiens

<400> SEQUENCE: 227
uuguagucga uguccagcac a                                              21

<210> SEQ ID NO 228
<211> LENGTH: 21
<212> TYPE: DNA
<213> ORGANISM: homo sapiens

<400> SEQUENCE: 228
uucguuccca auggcuucug t                                              21

<210> SEQ ID NO 229
<211> LENGTH: 21
<212> TYPE: DNA
<213> ORGANISM: homo sapiens

<400> SEQUENCE: 229
ucggcgucga uggugugcca g                                              21

<210> SEQ ID NO 230
<211> LENGTH: 21
<212> TYPE: DNA
<213> ORGANISM: homo sapiens

<400> SEQUENCE: 230
aaagaggucc aggccgacca g                                              21

<210> SEQ ID NO 231
<211> LENGTH: 21
<212> TYPE: DNA
<213> ORGANISM: homo sapiens

<400> SEQUENCE: 231
uuagaucucc aguuggccac g                                              21

<210> SEQ ID NO 232
<211> LENGTH: 21
<212> TYPE: DNA
<213> ORGANISM: homo sapiens

<400> SEQUENCE: 232
ugugaucucc ucuaccaact g                                              21
```

```
<210> SEQ ID NO 233
<211> LENGTH: 21
<212> TYPE: DNA
<213> ORGANISM: homo sapiens

<400> SEQUENCE: 233
uuggucagag cugcaguact t                                              21

<210> SEQ ID NO 234
<211> LENGTH: 21
<212> TYPE: DNA
<213> ORGANISM: homo sapiens

<400> SEQUENCE: 234
ugaugcuuau gucuucacgc a                                              21

<210> SEQ ID NO 235
<211> LENGTH: 21
<212> TYPE: DNA
<213> ORGANISM: homo sapiens

<400> SEQUENCE: 235
auuuggaacc acaucggcat g                                              21

<210> SEQ ID NO 236
<211> LENGTH: 21
<212> TYPE: DNA
<213> ORGANISM: homo sapiens

<400> SEQUENCE: 236
ucccgggucc aaccgaacga g                                              21

<210> SEQ ID NO 237
<211> LENGTH: 21
<212> TYPE: DNA
<213> ORGANISM: homo sapiens

<400> SEQUENCE: 237
ucugcuuccu uuaucucagc a                                              21

<210> SEQ ID NO 238
<211> LENGTH: 21
<212> TYPE: DNA
<213> ORGANISM: homo sapiens

<400> SEQUENCE: 238
aagucgaucc agauguagug g                                              21

<210> SEQ ID NO 239
<211> LENGTH: 21
<212> TYPE: DNA
<213> ORGANISM: homo sapiens

<400> SEQUENCE: 239
aagaggucga ugaucugcag g                                              21

<210> SEQ ID NO 240
<211> LENGTH: 21
<212> TYPE: DNA
<213> ORGANISM: homo sapiens

<400> SEQUENCE: 240
agagccgaca guuaugucca g                                              21
```

```
<210> SEQ ID NO 241
<211> LENGTH: 21
<212> TYPE: DNA
<213> ORGANISM: homo sapiens

<400> SEQUENCE: 241
uccuugagua gggaacuuug g                                              21

<210> SEQ ID NO 242
<211> LENGTH: 21
<212> TYPE: DNA
<213> ORGANISM: homo sapiens

<400> SEQUENCE: 242
uccggccugg ucuaguucca g                                              21

<210> SEQ ID NO 243
<211> LENGTH: 21
<212> TYPE: DNA
<213> ORGANISM: homo sapiens

<400> SEQUENCE: 243
ugugaugaga cgcucgauct c                                              21

<210> SEQ ID NO 244
<211> LENGTH: 21
<212> TYPE: DNA
<213> ORGANISM: homo sapiens

<400> SEQUENCE: 244
aaguaggaga ggccuguggg t                                              21

<210> SEQ ID NO 245
<211> LENGTH: 21
<212> TYPE: DNA
<213> ORGANISM: homo sapiens

<400> SEQUENCE: 245
uccggguguc cugauuauct g                                              21

<210> SEQ ID NO 246
<211> LENGTH: 21
<212> TYPE: DNA
<213> ORGANISM: homo sapiens

<400> SEQUENCE: 246
gagauggugg acaugccgct g                                              21

<210> SEQ ID NO 247
<211> LENGTH: 21
<212> TYPE: DNA
<213> ORGANISM: homo sapiens

<400> SEQUENCE: 247
ugccugccag gagaucuuct g                                              21

<210> SEQ ID NO 248
<211> LENGTH: 21
<212> TYPE: DNA
<213> ORGANISM: homo sapiens

<400> SEQUENCE: 248
```

-continued

```
cuucucgcga agcacauugc g                                        21

<210> SEQ ID NO 249
<211> LENGTH: 21
<212> TYPE: DNA
<213> ORGANISM: homo sapiens

<400> SEQUENCE: 249
ugcacggcua gguagggaga g                                        21

<210> SEQ ID NO 250
<211> LENGTH: 21
<212> TYPE: DNA
<213> ORGANISM: homo sapiens

<400> SEQUENCE: 250
ucucccgcau gaacuacagg t                                        21

<210> SEQ ID NO 251
<211> LENGTH: 21
<212> TYPE: DNA
<213> ORGANISM: homo sapiens

<400> SEQUENCE: 251
agaaaucaaa cucccgcugg t                                        21

<210> SEQ ID NO 252
<211> LENGTH: 21
<212> TYPE: DNA
<213> ORGANISM: homo sapiens

<400> SEQUENCE: 252
uuaucugaga acauggcggt c                                        21

<210> SEQ ID NO 253
<211> LENGTH: 21
<212> TYPE: DNA
<213> ORGANISM: homo sapiens

<400> SEQUENCE: 253
uuggguugac uugcuuccga g                                        21

<210> SEQ ID NO 254
<211> LENGTH: 21
<212> TYPE: DNA
<213> ORGANISM: homo sapiens

<400> SEQUENCE: 254
ucuuaucuga gaacauggcg g                                        21

<210> SEQ ID NO 255
<211> LENGTH: 21
<212> TYPE: DNA
<213> ORGANISM: homo sapiens

<400> SEQUENCE: 255
ucugagaaca uggcggucca a                                        21

<210> SEQ ID NO 256
<211> LENGTH: 21
<212> TYPE: DNA
<213> ORGANISM: homo sapiens

<400> SEQUENCE: 256
```
uugcuuccga ggcagccagg g         21

<210> SEQ ID NO 257
<211> LENGTH: 21
<212> TYPE: DNA
<213> ORGANISM: homo sapiens

<400> SEQUENCE: 257
ucaaguucac uaacuccaca t         21

<210> SEQ ID NO 258
<211> LENGTH: 21
<212> TYPE: DNA
<213> ORGANISM: homo sapiens

<400> SEQUENCE: 258
aucuccacuu ggucagagct g         21

<210> SEQ ID NO 259
<211> LENGTH: 21
<212> TYPE: DNA
<213> ORGANISM: homo sapiens

<400> SEQUENCE: 259
aacgagacgg gucacuucgt t         21

<210> SEQ ID NO 260
<211> LENGTH: 21
<212> TYPE: DNA
<213> ORGANISM: homo sapiens

<400> SEQUENCE: 260
uguguugauc cagccuuggg t         21

<210> SEQ ID NO 261
<211> LENGTH: 21
<212> TYPE: DNA
<213> ORGANISM: homo sapiens

<400> SEQUENCE: 261
uucugcucca ccgucaugug c         21

<210> SEQ ID NO 262
<211> LENGTH: 21
<212> TYPE: DNA
<213> ORGANISM: homo sapiens

<400> SEQUENCE: 262
uggagcaucg gcgucgaugg t         21

<210> SEQ ID NO 263
<211> LENGTH: 21
<212> TYPE: DNA
<213> ORGANISM: homo sapiens

<400> SEQUENCE: 263
ucgaugucca gcacaauggc c         21

<210> SEQ ID NO 264
<211> LENGTH: 21
<212> TYPE: DNA
<213> ORGANISM: homo sapiens

```
<400> SEQUENCE: 264
ucguucccaa uggcuucugt g                                              21

<210> SEQ ID NO 265
<211> LENGTH: 21
<212> TYPE: DNA
<213> ORGANISM: homo sapiens

<400> SEQUENCE: 265
uaacuccaca ucgcuucacc t                                              21

<210> SEQ ID NO 266
<211> LENGTH: 21
<212> TYPE: DNA
<213> ORGANISM: homo sapiens

<400> SEQUENCE: 266 ugaucccuc uaccaacuga t                                               21

<210> SEQ ID NO 267
<211> LENGTH: 21
<212> TYPE: DNA
<213> ORGANISM: homo sapiens

<400> SEQUENCE: 267
uuggcgaucu caaaccgcug c                                              21

<210> SEQ ID NO 268
<211> LENGTH: 21
<212> TYPE: DNA
<213> ORGANISM: homo sapiens

<400> SEQUENCE: 268 auguuugau ccagccuugg g                                               21

<210> SEQ ID NO 269
<211> LENGTH: 21
<212> TYPE: DNA
<213> ORGANISM: homo sapiens

<400> SEQUENCE: 269
cugauguacu uagaucucca g                                              21

<210> SEQ ID NO 270
<211> LENGTH: 21
<212> TYPE: DNA
<213> ORGANISM: homo sapiens

<400> SEQUENCE: 270
uggaguagau cuucucgcga a                                              21

<210> SEQ ID NO 271
<211> LENGTH: 21
<212> TYPE: DNA
<213> ORGANISM: homo sapiens

<400> SEQUENCE: 271
ucaggcacau cacuaacggc t                                              21

<210> SEQ ID NO 272
<211> LENGTH: 21
<212> TYPE: DNA
<213> ORGANISM: homo sapiens
```

<400> SEQUENCE: 272
uaggcggcca ugcuucggat g                                              21

<210> SEQ ID NO 273
<211> LENGTH: 21
<212> TYPE: DNA
<213> ORGANISM: homo sapiens

<400> SEQUENCE: 273
gaugcuuaug ucuucacgca g                                              21

<210> SEQ ID NO 274
<211> LENGTH: 21
<212> TYPE: DNA
<213> ORGANISM: homo sapiens

<400> SEQUENCE: 274
ucuccaguug gccacgcugt t                                              21

<210> SEQ ID NO 275
<211> LENGTH: 21
<212> TYPE: DNA
<213> ORGANISM: homo sapiens

<400> SEQUENCE: 275
ugaaguugua gcgggccugc t                                              21

<210> SEQ ID NO 276
<211> LENGTH: 21
<212> TYPE: DNA
<213> ORGANISM: homo sapiens

<400> SEQUENCE: 276
ugagcucugg agcaucggcg t                                              21

<210> SEQ ID NO 277
<211> LENGTH: 21
<212> TYPE: DNA
<213> ORGANISM: homo sapiens

<400> SEQUENCE: 277
aaggaauguu agcuccucug t                                              21

<210> SEQ ID NO 278
<211> LENGTH: 21
<212> TYPE: DNA
<213> ORGANISM: homo sapiens

<400> SEQUENCE: 278
uguucuuaaa ccuggcaggc a                                              21

<210> SEQ ID NO 279
<211> LENGTH: 21
<212> TYPE: DNA
<213> ORGANISM: homo sapiens

<400> SEQUENCE: 279
auguccagca caauggccuc a                                              21

<210> SEQ ID NO 280
<211> LENGTH: 21
<212> TYPE: DNA

```
<213> ORGANISM: homo sapiens

<400> SEQUENCE: 280
uacagaagga auguuagcuc c                                              21

<210> SEQ ID NO 281
<211> LENGTH: 21
<212> TYPE: DNA
<213> ORGANISM: homo sapiens

<400> SEQUENCE: 281
aagaucucca cuuggucaga g                                              21

<210> SEQ ID NO 282
<211> LENGTH: 21
<212> TYPE: DNA
<213> ORGANISM: homo sapiens

<400> SEQUENCE: 282
ucacuucguu cccaauggct t                                              21

<210> SEQ ID NO 283
<211> LENGTH: 21
<212> TYPE: DNA
<213> ORGANISM: homo sapiens

<400> SEQUENCE: 283
ugagacgcuc gaucucagug g                                              21

<210> SEQ ID NO 284
<211> LENGTH: 21
<212> TYPE: DNA
<213> ORGANISM: homo sapiens

<400> SEQUENCE: 284
uggcgaucuc aaaccgcugc a                                              21

<210> SEQ ID NO 285
<211> LENGTH: 21
<212> TYPE: DNA
<213> ORGANISM: homo sapiens

<400> SEQUENCE: 285
ugccagguga ccaggaacut g                                              21

<210> SEQ ID NO 286
<211> LENGTH: 21
<212> TYPE: DNA
<213> ORGANISM: homo sapiens

<400> SEQUENCE: 286
uacuuagauc uccaguuggc c                                              21

<210> SEQ ID NO 287
<211> LENGTH: 21
<212> TYPE: DNA
<213> ORGANISM: homo sapiens

<400> SEQUENCE: 287
cuuaucugag aacauggcgg t                                              21

<210> SEQ ID NO 288
<211> LENGTH: 21
```

<210> SEQ ID NO 288
<211> LENGTH: 21
<212> TYPE: DNA
<213> ORGANISM: homo sapiens

<400> SEQUENCE: 288
uccacaucgc uucaccuuga a                                              21

<210> SEQ ID NO 289
<211> LENGTH: 21
<212> TYPE: DNA
<213> ORGANISM: homo sapiens

<400> SEQUENCE: 289
ucggaugaag uuguagcggg c                                              21

<210> SEQ ID NO 290
<211> LENGTH: 21
<212> TYPE: DNA
<213> ORGANISM: homo sapiens

<400> SEQUENCE: 290
aguggaguag aucuucucgc g                                              21

<210> SEQ ID NO 291
<211> LENGTH: 21
<212> TYPE: DNA
<213> ORGANISM: homo sapiens

<400> SEQUENCE: 291
cuucguuccc aauggcuuct g                                              21

<210> SEQ ID NO 292
<211> LENGTH: 21
<212> TYPE: DNA
<213> ORGANISM: homo sapiens

<400> SEQUENCE: 292
aagaggaugg cguccggagg g                                              21

<210> SEQ ID NO 293
<211> LENGTH: 21
<212> TYPE: DNA
<213> ORGANISM: homo sapiens

<400> SEQUENCE: 293
guggaguaga ucuucucgcg a                                              21

<210> SEQ ID NO 294
<211> LENGTH: 21
<212> TYPE: DNA
<213> ORGANISM: homo sapiens

<400> SEQUENCE: 294
agacggguca cuucguuccc a                                              21

<210> SEQ ID NO 295
<211> LENGTH: 21
<212> TYPE: DNA
<213> ORGANISM: homo sapiens

<400> SEQUENCE: 295
aggaagucga uccagaugua g                                              21

<210> SEQ ID NO 296

<210> SEQ ID NO 296
<211> LENGTH: 21
<212> TYPE: DNA
<213> ORGANISM: homo sapiens

<400> SEQUENCE: 296
uuuggaacca caucggcaug c                                              21

<210> SEQ ID NO 297
<211> LENGTH: 21
<212> TYPE: DNA
<213> ORGANISM: homo sapiens

<400> SEQUENCE: 297
ugaugagacg cucgaucuca g                                              21

<210> SEQ ID NO 298
<211> LENGTH: 21
<212> TYPE: DNA
<213> ORGANISM: homo sapiens

<400> SEQUENCE: 298
cuguaggcgg ccaugcuucg g                                              21

<210> SEQ ID NO 299
<211> LENGTH: 21
<212> TYPE: DNA
<213> ORGANISM: homo sapiens

<400> SEQUENCE: 299
ucucaaaccg cugcaccagg a                                              21

<210> SEQ ID NO 300
<211> LENGTH: 21
<212> TYPE: DNA
<213> ORGANISM: homo sapiens

<400> SEQUENCE: 300
aaggagccug ugaucuccuc t                                              21

<210> SEQ ID NO 301
<211> LENGTH: 21
<212> TYPE: DNA
<213> ORGANISM: homo sapiens

<400> SEQUENCE: 301
agcugaagua gucaaaggca g                                              21

<210> SEQ ID NO 302
<211> LENGTH: 21
<212> TYPE: DNA
<213> ORGANISM: homo sapiens

<400> SEQUENCE: 302
augagacgcu cgaucucagt g                                              21

<210> SEQ ID NO 303
<211> LENGTH: 21
<212> TYPE: DNA
<213> ORGANISM: homo sapiens

<400> SEQUENCE: 303
uucccaaugg cuucugugut c                                              21

-continued

```
<210> SEQ ID NO 304
<211> LENGTH: 21
<212> TYPE: DNA
<213> ORGANISM: homo sapiens

<400> SEQUENCE: 304
uguccagcac aauggccuca g                                              21

<210> SEQ ID NO 305
<211> LENGTH: 21
<212> TYPE: DNA
<213> ORGANISM: homo sapiens

<400> SEQUENCE: 305
uggguugacu ugcuuccgag g                                              21

<210> SEQ ID NO 306
<211> LENGTH: 21
<212> TYPE: DNA
<213> ORGANISM: homo sapiens

<400> SEQUENCE: 306
acuaacucca caucgcuuca c                                              21

<210> SEQ ID NO 307
<211> LENGTH: 21
<212> TYPE: DNA
<213> ORGANISM: homo sapiens

<400> SEQUENCE: 307
uggucagagc ugcaguacut g                                              21

<210> SEQ ID NO 308
<211> LENGTH: 21
<212> TYPE: DNA
<213> ORGANISM: homo sapiens

<400> SEQUENCE: 308
ccugauuucu uggagauggt g                                              21

<210> SEQ ID NO 309
<211> LENGTH: 21
<212> TYPE: DNA
<213> ORGANISM: homo sapiens

<400> SEQUENCE: 309
uagucgaugu ccagcacaat g                                              21

<210> SEQ ID NO 310
<211> LENGTH: 21
<212> TYPE: DNA
<213> ORGANISM: homo sapiens

<400> SEQUENCE: 310
aaguuguagc gggccugcug g                                              21

<210> SEQ ID NO 311
<211> LENGTH: 21
<212> TYPE: DNA
<213> ORGANISM: homo sapiens

<400> SEQUENCE: 311
ugcacucauc cucggaguct g                                              21
```

```
<210> SEQ ID NO 312
<211> LENGTH: 21
<212> TYPE: DNA
<213> ORGANISM: homo sapiens

<400> SEQUENCE: 312
aucucccgca ugaacuacag g                                              21

<210> SEQ ID NO 313
<211> LENGTH: 23
<212> TYPE: DNA
<213> ORGANISM: homo sapiens

<400> SEQUENCE: 313
aauagguagg gagagaugcu ctt                                            23

<210> SEQ ID NO 314
<211> LENGTH: 23
<212> TYPE: DNA
<213> ORGANISM: homo sapiens

<400> SEQUENCE: 314
aauaacucca caucgcuuca ctt                                            23

<210> SEQ ID NO 315
<211> LENGTH: 23
<212> TYPE: DNA
<213> ORGANISM: homo sapiens

<400> SEQUENCE: 315
aaaaguagga gaggccugug gtt                                            23

<210> SEQ ID NO 316
<211> LENGTH: 22
<212> TYPE: DNA
<213> ORGANISM: homo sapiens

<400> SEQUENCE: 316
aaaacaggcc aaauuucugc tt                                             22

<210> SEQ ID NO 317
<211> LENGTH: 21
<212> TYPE: DNA
<213> ORGANISM: homo sapiens

<400> SEQUENCE: 317
ccauguucuc agauaagaat t                                              21

<210> SEQ ID NO 318
<211> LENGTH: 21
<212> TYPE: DNA
<213> ORGANISM: homo sapiens

<400> SEQUENCE: 318
ggaagcaagu caacccaaat t                                              21

<210> SEQ ID NO 319
<211> LENGTH: 21
<212> TYPE: DNA
<213> ORGANISM: homo sapiens

<400> SEQUENCE: 319
cggacgccau ccucuucuat t                                              21
```

```
<210> SEQ ID NO 320
<211> LENGTH: 21
<212> TYPE: DNA
<213> ORGANISM: homo sapiens

<400> SEQUENCE: 320
aaggcuggau caacacauat t                                              21

<210> SEQ ID NO 321
<211> LENGTH: 21
<212> TYPE: DNA
<213> ORGANISM: homo sapiens

<400> SEQUENCE: 321
cauaucuggc caaguucaat t                                              21

<210> SEQ ID NO 322
<211> LENGTH: 21
<212> TYPE: DNA
<213> ORGANISM: homo sapiens

<400> SEQUENCE: 322
ccaacguguc ggcuaucaut t                                              21

<210> SEQ ID NO 323
<211> LENGTH: 21
<212> TYPE: DNA
<213> ORGANISM: homo sapiens

<400> SEQUENCE: 323
cguuagugau gugccugaat t                                              21

<210> SEQ ID NO 324
<211> LENGTH: 21
<212> TYPE: DNA
<213> ORGANISM: homo sapiens

<400> SEQUENCE: 324
cgcuacaacu ucauccgaat t                                              21

<210> SEQ ID NO 325
<211> LENGTH: 21
<212> TYPE: DNA
<213> ORGANISM: homo sapiens

<400> SEQUENCE: 325
uggaguuagu gaacuugaat t                                              21

<210> SEQ ID NO 326
<211> LENGTH: 21
<212> TYPE: DNA
<213> ORGANISM: homo sapiens

<400> SEQUENCE: 326
gcucagacuc cgaggaugat t                                              21

<210> SEQ ID NO 327
<211> LENGTH: 21
<212> TYPE: DNA
<213> ORGANISM: homo sapiens

<400> SEQUENCE: 327
```
caugacggug gagcagaaat t          21

<210> SEQ ID NO 328
<211> LENGTH: 21
<212> TYPE: DNA
<213> ORGANISM: homo sapiens

<400> SEQUENCE: 328
cagaggagcu aacauuccut t          21

<210> SEQ ID NO 329
<211> LENGTH: 21
<212> TYPE: DNA
<213> ORGANISM: homo sapiens

<400> SEQUENCE: 329
ccacugccuu ugacuacuut t          21

<210> SEQ ID NO 330
<211> LENGTH: 21
<212> TYPE: DNA
<213> ORGANISM: homo sapiens

<400> SEQUENCE: 330
cggcccuguc ugaagugaat t          21

<210> SEQ ID NO 331
<211> LENGTH: 21
<212> TYPE: DNA
<213> ORGANISM: homo sapiens

<400> SEQUENCE: 331
ugcuggacau cgacuacaat t          21

<210> SEQ ID NO 332
<211> LENGTH: 21
<212> TYPE: DNA
<213> ORGANISM: homo sapiens

<400> SEQUENCE: 332
agaagccauu gggaacgaat t          21

<210> SEQ ID NO 333
<211> LENGTH: 21
<212> TYPE: DNA
<213> ORGANISM: homo sapiens

<400> SEQUENCE: 333
ggcacaccau cgacgccgat t          21

<210> SEQ ID NO 334
<211> LENGTH: 21
<212> TYPE: DNA
<213> ORGANISM: homo sapiens

<400> SEQUENCE: 334
ggucggccug gaccucuuut t          21

<210> SEQ ID NO 335
<211> LENGTH: 21
<212> TYPE: DNA
<213> ORGANISM: homo sapiens

<400> SEQUENCE: 335

```
uggccaacug gagaucuaat t                                                    21

<210> SEQ ID NO 336
<211> LENGTH: 21
<212> TYPE: DNA
<213> ORGANISM: homo sapiens

<400> SEQUENCE: 336
guugguagag gagaucacat t                                                    21

<210> SEQ ID NO 337
<211> LENGTH: 21
<212> TYPE: DNA
<213> ORGANISM: homo sapiens

<400> SEQUENCE: 337
guacugcagc ucugaccaat t                                                    21

<210> SEQ ID NO 338
<211> LENGTH: 21
<212> TYPE: DNA
<213> ORGANISM: homo sapiens

<400> SEQUENCE: 338
cgugaagaca uaagcaucat t                                                    21

<210> SEQ ID NO 339
<211> LENGTH: 21
<212> TYPE: DNA
<213> ORGANISM: homo sapiens

<400> SEQUENCE: 339
ugccgaugug guuccaaaut t                                                    21

<210> SEQ ID NO 340
<211> LENGTH: 21
<212> TYPE: DNA
<213> ORGANISM: homo sapiens

<400> SEQUENCE: 340
cguucgguug gacccgggat t                                                    21

<210> SEQ ID NO 341
<211> LENGTH: 21
<212> TYPE: DNA
<213> ORGANISM: homo sapiens

<400> SEQUENCE: 341
cugagauaaa ggaagcagat t                                                    21

<210> SEQ ID NO 342
<211> LENGTH: 21
<212> TYPE: DNA
<213> ORGANISM: homo sapiens

<400> SEQUENCE: 342
acuacaucug gaucgacuut t                                                    21

<210> SEQ ID NO 343
<211> LENGTH: 21
<212> TYPE: DNA
<213> ORGANISM: homo sapiens
```

```
<400> SEQUENCE: 343
ugcagaucau cgaccucuut t                                            21

<210> SEQ ID NO 344
<211> LENGTH: 21
<212> TYPE: DNA
<213> ORGANISM: homo sapiens

<400> SEQUENCE: 344
ggacauaacu gucggcucut t                                            21

<210> SEQ ID NO 345
<211> LENGTH: 21
<212> TYPE: DNA
<213> ORGANISM: homo sapiens

<400> SEQUENCE: 345
aaaguucccu acucaaggat t                                            21

<210> SEQ ID NO 346
<211> LENGTH: 21
<212> TYPE: DNA
<213> ORGANISM: homo sapiens

<400> SEQUENCE: 346
ggaacuagac caggccggat t                                            21

<210> SEQ ID NO 347
<211> LENGTH: 21
<212> TYPE: DNA
<213> ORGANISM: homo sapiens

<400> SEQUENCE: 347
gaucgagcgu cucaucacat t                                            21

<210> SEQ ID NO 348
<211> LENGTH: 21
<212> TYPE: DNA
<213> ORGANISM: homo sapiens

<400> SEQUENCE: 348
ccacaggccu cuccuacuut t                                            21

<210> SEQ ID NO 349
<211> LENGTH: 21
<212> TYPE: DNA
<213> ORGANISM: homo sapiens

<400> SEQUENCE: 349
gauaaucagg acacccggat t                                            21

<210> SEQ ID NO 350
<211> LENGTH: 21
<212> TYPE: DNA
<213> ORGANISM: homo sapiens

<400> SEQUENCE: 350
gcggcauguc caccaucuct t                                            21

<210> SEQ ID NO 351
<211> LENGTH: 21
<212> TYPE: DNA
<213> ORGANISM: homo sapiens
```

```
<400> SEQUENCE: 351
gaagaucucc uggcaggcat t                                              21

<210> SEQ ID NO 352
<211> LENGTH: 21
<212> TYPE: DNA
<213> ORGANISM: homo sapiens

<400> SEQUENCE: 352
caaugugcuu cgcgagaagt t                                              21

<210> SEQ ID NO 353
<211> LENGTH: 21
<212> TYPE: DNA
<213> ORGANISM: homo sapiens

<400> SEQUENCE: 353
cucccuaccu agccgugcat t                                              21

<210> SEQ ID NO 354
<211> LENGTH: 21
<212> TYPE: DNA
<213> ORGANISM: homo sapiens

<400> SEQUENCE: 354
cuguaguuca ugcgggagat t                                              21

<210> SEQ ID NO 355
<211> LENGTH: 21
<212> TYPE: DNA
<213> ORGANISM: homo sapiens

<400> SEQUENCE: 355
cagcgggagu uugauuucut t                                              21

<210> SEQ ID NO 356
<211> LENGTH: 21
<212> TYPE: DNA
<213> ORGANISM: homo sapiens

<400> SEQUENCE: 356
ccgccauguu cucagauaat t                                              21

<210> SEQ ID NO 357
<211> LENGTH: 21
<212> TYPE: DNA
<213> ORGANISM: homo sapiens

<400> SEQUENCE: 357
cggaagcaag ucaacccaat t                                              21

<210> SEQ ID NO 358
<211> LENGTH: 21
<212> TYPE: DNA
<213> ORGANISM: homo sapiens

<400> SEQUENCE: 358
gccauguucu cagauaagat t                                              21

<210> SEQ ID NO 359
<211> LENGTH: 21
<212> TYPE: DNA
```

```
<213> ORGANISM: homo sapiens

<400> SEQUENCE: 359
ggaccgccau guucucagat t                                              21

<210> SEQ ID NO 360
<211> LENGTH: 21
<212> TYPE: DNA
<213> ORGANISM: homo sapiens

<400> SEQUENCE: 360
cuggcugccu cggaagcaat t                                              21

<210> SEQ ID NO 361
<211> LENGTH: 21
<212> TYPE: DNA
<213> ORGANISM: homo sapiens

<400> SEQUENCE: 361
guggaguuag ugaacuugat t                                              21

<210> SEQ ID NO 362
<211> LENGTH: 21
<212> TYPE: DNA
<213> ORGANISM: homo sapiens

<400> SEQUENCE: 362
gcucugacca aguggagaut t                                              21

<210> SEQ ID NO 363
<211> LENGTH: 21
<212> TYPE: DNA
<213> ORGANISM: homo sapiens

<400> SEQUENCE: 363
cgaagugacc cgucucguut t                                              21

<210> SEQ ID NO 364
<211> LENGTH: 21
<212> TYPE: DNA
<213> ORGANISM: homo sapiens

<400> SEQUENCE: 364
ccaaggcugg aucaacacat t                                              21

<210> SEQ ID NO 365
<211> LENGTH: 21
<212> TYPE: DNA
<213> ORGANISM: homo sapiens

<400> SEQUENCE: 365
acaugacggu ggagcagaat t                                              21

<210> SEQ ID NO 366
<211> LENGTH: 21
<212> TYPE: DNA
<213> ORGANISM: homo sapiens

<400> SEQUENCE: 366
caucgacgcc gaugcuccat t                                              21

<210> SEQ ID NO 367
<211> LENGTH: 21
```

<212> TYPE: DNA
<213> ORGANISM: homo sapiens

<400> SEQUENCE: 367
ccauugugcu ggacaucgat t                                    21

<210> SEQ ID NO 368
<211> LENGTH: 21
<212> TYPE: DNA
<213> ORGANISM: homo sapiens

<400> SEQUENCE: 368
cagaagccau ugggaacgat t                                    21

<210> SEQ ID NO 369
<211> LENGTH: 21
<212> TYPE: DNA
<213> ORGANISM: homo sapiens

<400> SEQUENCE: 369
gugaagcgau guggaguuat t                                    21

<210> SEQ ID NO 370
<211> LENGTH: 21
<212> TYPE: DNA
<213> ORGANISM: homo sapiens

<400> SEQUENCE: 370
caguugguag aggagaucat t                                    21

<210> SEQ ID NO 371
<211> LENGTH: 21
<212> TYPE: DNA
<213> ORGANISM: homo sapiens

<400> SEQUENCE: 371
agcgguuuga gaucgccaat t                                    21

<210> SEQ ID NO 372
<211> LENGTH: 21
<212> TYPE: DNA
<213> ORGANISM: homo sapiens

<400> SEQUENCE: 372
caaggcugga ucaacacaut t                                    21

<210> SEQ ID NO 373
<211> LENGTH: 21
<212> TYPE: DNA
<213> ORGANISM: homo sapiens

<400> SEQUENCE: 373
ggagaucuaa guacaucagt t                                    21

<210> SEQ ID NO 374
<211> LENGTH: 21
<212> TYPE: DNA
<213> ORGANISM: homo sapiens

<400> SEQUENCE: 374
cgcgagaaga ucuacuccat t                                    21

<210> SEQ ID NO 375

-continued

```
<211> LENGTH: 21
<212> TYPE: DNA
<213> ORGANISM: homo sapiens

<400> SEQUENCE: 375
ccguuaguga ugugccugat t                                              21

<210> SEQ ID NO 376
<211> LENGTH: 21
<212> TYPE: DNA
<213> ORGANISM: homo sapiens

<400> SEQUENCE: 376
uccgaagcau ggccgccuat t                                              21

<210> SEQ ID NO 377
<211> LENGTH: 21
<212> TYPE: DNA
<213> ORGANISM: homo sapiens

<400> SEQUENCE: 377
gcgugaagac auaagcauct t                                              21

<210> SEQ ID NO 378
<211> LENGTH: 21
<212> TYPE: DNA
<213> ORGANISM: homo sapiens

<400> SEQUENCE: 378
cagcguggcc aacuggagat t                                              21

<210> SEQ ID NO 379
<211> LENGTH: 21
<212> TYPE: DNA
<213> ORGANISM: homo sapiens

<400> SEQUENCE: 379
caggcccgcu acaacuucat t                                              21

<210> SEQ ID NO 380
<211> LENGTH: 21
<212> TYPE: DNA
<213> ORGANISM: homo sapiens

<400> SEQUENCE: 380
gccgaugcuc cagagcucat t                                              21

<210> SEQ ID NO 381
<211> LENGTH: 21
<212> TYPE: DNA
<213> ORGANISM: homo sapiens

<400> SEQUENCE: 381
agaggagcua acauuccuut t                                              21

<210> SEQ ID NO 382
<211> LENGTH: 21
<212> TYPE: DNA
<213> ORGANISM: homo sapiens

<400> SEQUENCE: 382
ccugccaggu uuagaacat t                                               21
```

-continued

```
<210> SEQ ID NO 383
<211> LENGTH: 21
<212> TYPE: DNA
<213> ORGANISM: homo sapiens

<400> SEQUENCE: 383
aggccauugu gcuggacaut t                                              21

<210> SEQ ID NO 384
<211> LENGTH: 21
<212> TYPE: DNA
<213> ORGANISM: homo sapiens

<400> SEQUENCE: 384
agcuaacauu ccuucuguat t                                              21

<210> SEQ ID NO 385
<211> LENGTH: 21
<212> TYPE: DNA
<213> ORGANISM: homo sapiens

<400> SEQUENCE: 385
cugaccaagu ggagaucuut t                                              21

<210> SEQ ID NO 386
<211> LENGTH: 21
<212> TYPE: DNA
<213> ORGANISM: homo sapiens

<400> SEQUENCE: 386
gccauuggga acgaagugat t                                              21

<210> SEQ ID NO 387
<211> LENGTH: 21
<212> TYPE: DNA
<213> ORGANISM: homo sapiens

<400> SEQUENCE: 387
acugagaucg agcgucucat t                                              21

<210> SEQ ID NO 388
<211> LENGTH: 21
<212> TYPE: DNA
<213> ORGANISM: homo sapiens

<400> SEQUENCE: 388
cagcgguuug agaucgccat t                                              21

<210> SEQ ID NO 389
<211> LENGTH: 21
<212> TYPE: DNA
<213> ORGANISM: homo sapiens

<400> SEQUENCE: 389 aguccuggu caccuggcat t                                               21

<210> SEQ ID NO 390
<211> LENGTH: 21
<212> TYPE: DNA
<213> ORGANISM: homo sapiens

<400> SEQUENCE: 390
ccaacuggag aucuaaguat t                                              21
```

<210> SEQ ID NO 391
<211> LENGTH: 21
<212> TYPE: DNA
<213> ORGANISM: homo sapiens

<400> SEQUENCE: 391
cgccauguuc ucagauaagt t                                              21

<210> SEQ ID NO 392
<211> LENGTH: 21
<212> TYPE: DNA
<213> ORGANISM: homo sapiens

<400> SEQUENCE: 392
caaggugaag cgauguggat t                                              21

<210> SEQ ID NO 393
<211> LENGTH: 21
<212> TYPE: DNA
<213> ORGANISM: homo sapiens

<400> SEQUENCE: 393
ccgcuacaac uucauccgat t                                              21

<210> SEQ ID NO 394
<211> LENGTH: 21
<212> TYPE: DNA
<213> ORGANISM: homo sapiens

<400> SEQUENCE: 394
cgagaagauc uacuccacut t                                              21

<210> SEQ ID NO 395
<211> LENGTH: 21
<212> TYPE: DNA
<213> ORGANISM: homo sapiens

<400> SEQUENCE: 395
gaagccauug ggaacgaagt t                                              21

<210> SEQ ID NO 396
<211> LENGTH: 21
<212> TYPE: DNA
<213> ORGANISM: homo sapiens

<400> SEQUENCE: 396
cuccggacgc cauccucuut t                                              21

<210> SEQ ID NO 397
<211> LENGTH: 21
<212> TYPE: DNA
<213> ORGANISM: homo sapiens

<400> SEQUENCE: 397
gcgagaagau cuacuccact t                                              21

<210> SEQ ID NO 398
<211> LENGTH: 21
<212> TYPE: DNA
<213> ORGANISM: homo sapiens

<400> SEQUENCE: 398
ggaacgaagu gacccgucut t                                              21

<210> SEQ ID NO 399
<211> LENGTH: 21
<212> TYPE: DNA
<213> ORGANISM: homo sapiens

<400> SEQUENCE: 399
acaucuggau cgacuuccut t                                              21

<210> SEQ ID NO 400
<211> LENGTH: 21
<212> TYPE: DNA
<213> ORGANISM: homo sapiens

<400> SEQUENCE: 400
augccgaugu gguuccaaat t                                              21

<210> SEQ ID NO 401
<211> LENGTH: 21
<212> TYPE: DNA
<213> ORGANISM: homo sapiens

<400> SEQUENCE: 401
gagaucgagc gucucaucat t                                              21

<210> SEQ ID NO 402
<211> LENGTH: 21
<212> TYPE: DNA
<213> ORGANISM: homo sapiens

<400> SEQUENCE: 402
gaagcauggc cgccuacagt t                                              21

<210> SEQ ID NO 403
<211> LENGTH: 21
<212> TYPE: DNA
<213> ORGANISM: homo sapiens

<400> SEQUENCE: 403
cuggugcagc gguuugagat t                                              21

<210> SEQ ID NO 404
<211> LENGTH: 21
<212> TYPE: DNA
<213> ORGANISM: homo sapiens

<400> SEQUENCE: 404
aggagaucac aggcuccuut t                                              21

<210> SEQ ID NO 405
<211> LENGTH: 21
<212> TYPE: DNA
<213> ORGANISM: homo sapiens

<400> SEQUENCE: 405
gccuuugacu acuucagcut t                                              21

<210> SEQ ID NO 406
<211> LENGTH: 21
<212> TYPE: DNA
<213> ORGANISM: homo sapiens

<400> SEQUENCE: 406

```
cugagaucga gcgucucaut t                                              21

<210> SEQ ID NO 407
<211> LENGTH: 21
<212> TYPE: DNA
<213> ORGANISM: homo sapiens

<400> SEQUENCE: 407
acacagaagc cauugggaat t                                              21

<210> SEQ ID NO 408
<211> LENGTH: 21
<212> TYPE: DNA
<213> ORGANISM: homo sapiens

<400> SEQUENCE: 408
gaggccauug ugcuggacat t                                              21

<210> SEQ ID NO 409
<211> LENGTH: 21
<212> TYPE: DNA
<213> ORGANISM: homo sapiens

<400> SEQUENCE: 409
ucggaagcaa gucaacccat t                                              21

<210> SEQ ID NO 410
<211> LENGTH: 21
<212> TYPE: DNA
<213> ORGANISM: homo sapiens

<400> SEQUENCE: 410
gaagcgaugu ggaguuagut t                                              21

<210> SEQ ID NO 411
<211> LENGTH: 21
<212> TYPE: DNA
<213> ORGANISM: homo sapiens

<400> SEQUENCE: 411
aguacugcag cucugaccat t                                              21

<210> SEQ ID NO 412
<211> LENGTH: 21
<212> TYPE: DNA
<213> ORGANISM: homo sapiens

<400> SEQUENCE: 412
ccaucuccaa gaaaucaggt t                                              21

<210> SEQ ID NO 413
<211> LENGTH: 21
<212> TYPE: DNA
<213> ORGANISM: homo sapiens

<400> SEQUENCE: 413
uugugcugga caucgacuat t                                              21

<210> SEQ ID NO 414
<211> LENGTH: 21
<212> TYPE: DNA
<213> ORGANISM: homo sapiens

<400> SEQUENCE: 414
```
agcaggcccg cuacaacuut t                                           21

<210> SEQ ID NO 415
<211> LENGTH: 21
<212> TYPE: DNA
<213> ORGANISM: homo sapiens

<400> SEQUENCE: 415
gacuccgagg augagugcat t                                           21

<210> SEQ ID NO 416
<211> LENGTH: 21
<212> TYPE: DNA
<213> ORGANISM: homo sapiens

<400> SEQUENCE: 416
uguaguucau gcgggagaut t                                           21

<210> SEQ ID NO 417
<211> LENGTH: 20
<212> TYPE: DNA
<213> ORGANISM: homo sapiens

<400> SEQUENCE: 417
gccctgtctg aagtgaaggt                                             20

<210> SEQ ID NO 418
<211> LENGTH: 20
<212> TYPE: DNA
<213> ORGANISM: homo sapiens

<400> SEQUENCE: 418
cttttgcagc actctgcatc                                             20

<210> SEQ ID NO 419
<211> LENGTH: 20
<212> TYPE: DNA
<213> ORGANISM: homo sapiens

<400> SEQUENCE: 419
atggacaagg tggtgcagat                                             20

<210> SEQ ID NO 420
<211> LENGTH: 20
<212> TYPE: DNA
<213> ORGANISM: homo sapiens

<400> SEQUENCE: 420
cctcagtcat gctcatgtgg                                             20

<210> SEQ ID NO 421
<211> LENGTH: 57
<212> TYPE: DNA
<213> ORGANISM: homo sapiens

<400> SEQUENCE: 421
ccgggctgca caaatactac atgaactcga gttcatgtag tatttgtgca gcttttt    57

<210> SEQ ID NO 422
<211> LENGTH: 57
<212> TYPE: DNA
<213> ORGANISM: homo sapiens

```
<400> SEQUENCE: 422
ccgggcgtct catcacatgg tacaactcga gttgtaccat gtgatgagac gctttt        57

<210> SEQ ID NO 423
<211> LENGTH: 57
<212> TYPE: DNA
<213> ORGANISM: homo sapiens

<400> SEQUENCE: 423
ccgggccagg tttaagaaca cagaactcga gttctgtgtt cttaaacctg gctttt        57

<210> SEQ ID NO 424
<211> LENGTH: 57
<212> TYPE: DNA
<213> ORGANISM: homo sapiens

<400> SEQUENCE: 424
ccggccagtt catctggaac atgaactcga gttcatgttc cagatgaact ggttttt       57

<210> SEQ ID NO 425
<211> LENGTH: 57
<212> TYPE: DNA
<213> ORGANISM: homo sapiens

<400> SEQUENCE: 425
ccggcaagct cttgaagcac aggttctcga gaacctgtgc ttcaagagct tgttttt       57

<210> SEQ ID NO 426
<211> LENGTH: 57
<212> TYPE: DNA
<213> ORGANISM: homo sapiens

<400> SEQUENCE: 426
ccggccagtt gcttaacatg tacatctcga gatgtacatg ttaagcaact ggttttt       57

<210> SEQ ID NO 427
<211> LENGTH: 57
<212> TYPE: DNA
<213> ORGANISM: homo sapiens

<400> SEQUENCE: 427
ccggccgaga gtattgataa ttcatctcga gatgaattat caatactctc ggttttt       57

<210> SEQ ID NO 428
<211> LENGTH: 57
<212> TYPE: DNA
<213> ORGANISM: homo sapiens

<400> SEQUENCE: 428
ccggccatac aagattcttg tgattctcga gaatcacaag aatcttgtat ggttttt       57

<210> SEQ ID NO 429
<211> LENGTH: 57
<212> TYPE: DNA
<213> ORGANISM: homo sapiens

<400> SEQUENCE: 429
ccggcgacat gttcaactac tataactcga gttatagtag ttgaacatgt cgttttt       57
```

```
<210> SEQ ID NO 430
<211> LENGTH: 57
<212> TYPE: DNA
<213> ORGANISM: homo sapiens

<400> SEQUENCE: 430
ccggtctcgg tacttaggac ttgatctcga gatcaagtcc taagtaccga gattttt    57
```

DSRNA FOR TREATING VIRAL INFECTION

This application is a divisional of U.S. patent application Ser. No. 14/812,187, filed Jul. 29, 2015, which is a divisional application of U.S. patent application Ser. No. 14/069,642, filed Nov. 1, 2013 (now U.S. Pat. No. 9,133,462), which is a divisional application of U.S. patent application Ser. No. 13/359,129, filed 26 Jan. 2012 (now U.S. Pat. No. 8,603, 995), which is a divisional application of U.S. patent application Ser. No. 12/667,631, having a 35 USC § 371 date of 4 Jan. 2010, which claims priority to PCT Application Serial No. PCT/EP2008/058706, filed 4 Jul. 2008, and U.S. Provisional Application Ser. No. 60/948,100, filed 5 Jul. 2007, the contents of each of which are incorporated herein by reference in their entirety.

SEQUENCE LISTING

This application contains a Sequence Listing which has been submitted electronically in ASCII format. The ASCII copy, created on Mar. 28, 2017, is named "N052154-US5_SequenceListing.txt" and is 63 KB in size.

FIELD OF THE INVENTION

This invention relates to double-stranded ribonucleic acid (dsRNA) targeting human phosphatidylinositol 4-kinase, in particular human phosphatidylinositol 4-kinase catalytic, beta polypeptide (PIK4CB; NM 002651) and/or human phosphatidylinositol 4-kinase alpha polypeptide (PIK4CA; NM 002650) and its use (via RNA interference) to treat pathological processes mediated by infection from positive stranded RNA viruses such as hepatitis C virus (HCV).

BACKGROUND OF THE INVENTION

RNA-dependent RNA polymerase positive strand RNA viruses make up a large superfamily of viruses from many distinct subfamilies. These viruses span both the plant and animal kingdoms causing pathologies ranging from mild phenotypes to severe debilitating disease. The composition of the positive strand RNA virus polymerase supergroup is as follows. I. Picorna- (HAV, polio, Coxsackie), noda-, como-, nepo-, poty-, bymo-, sobemoviruses, and luteoviruses (yellows, yellow drawf, and leafroll virus). II. Carmo-, tombus-, dianthoviruses, pestiviruses, toga-, echo-, Dengue, hepatitis C virus, flaviviruses. III. Tobamo-, tobra-, hordei-, tricorna-, alpha, rubi-, furoviruses, hepatitis E virus, potex-, carla-, tymoviruses, and apple chlorotic leaf spot virus. The genomes of positive-strand RNA viruses encode RNA-dependent RNA polymerases which is the only viral protein containing motifs conserved across this class of viruses. This conservation is significant since this class of viruses contains significant phylogenetic variability, one would predict there are many ways in which the viruses infect cells and maintain stable replication. Besides the many differences, all the viruses in this class depend on a single fundamental step of RNA dependent positive strand RNA transcription. Since this step is essential for the viral life cycle this virus uses many host proteins to start and maintain RNA dependent RNA polymerase activity. Without the interaction of host factors the viruses would be unable to survive. Therefore a possible therapeutic intervention for inhibiting viral infection would be blocking the virus host interaction. If host factors essential for the virus but not essential for the host can be manipulated, then the ability to block viral infection could be achieved. Targeting host proteins has already been proven to be an efficacious approach to disrupt viral infection and replication for HIV, HCV, small pox, etc.

The significance of positive strand RNA viruses is the impact on human health and viability. Several positive strand RNA viruses infect humans and in many cases lead to debilitating disease and/or morbidity. Several viruses with a particular burden on human health is the Dengue virus (hemoragic fever), HCV (chronic liver disease, liver failure, fibrosis, and cancer), and HEV (fulminant hepatic failure). The liver and blood diseases caused by these viruses causes millions of deaths world wide and costs the heath care industry billions of dollars in liver related illness. The significance of finding therapies for curbing viral infection is great and would improve human health around the world.

As such there exists an unmet need for effective treatment of infections caused by HCV and other positive strand RNA viruses (listed above).

This specification also relates to double-stranded RNA molecules (dsRNA). dsRNA have been shown to block gene expression in a highly conserved regulatory mechanism known as RNA interference (RNAi). WO 99/32619 (Fire et al.) discloses the use of a dsRNA of at least 25 nucleotides in length to inhibit the expression of genes in *C. elegans*. dsRNA has also been shown to degrade target RNA in other organisms, including plants (see, e.g., WO 99/53050, Waterhouse et al.; and WO 99/61631, Heifetz et al.), *Drosophila* (see, e.g., Yang, D., et al., *Curr. Biol.* (2000) 10:1191-1200), and mammals (see WO 00/44895, Limmer; and DE 101 00 586.5, Kreutzer et al.). This natural mechanism has now become the focus for the development of a new class of pharmaceutical agents for treating disorders that are caused by the aberrant or unwanted regulation of a gene.

PCT Publications WO 2003016572, WO 2003070750 and WO 2005028650 disclose previous efforts to develop nucleic acid based RNAi medicaments for the treatment of disease caused by HCV infection. PCT Publication WO2006074346 discloses previous efforts to treat RSV infection using RNAi medicaments.

Despite significant advances in the field of RNAi and advances in the treatment of pathological processes mediated by viral infection, there remains a need for agents that can inhibit the progression of viral infection and that can treat diseases associated with viral infection. The instant invention discloses compounds, compositions and methods that meet this need, and provide other benefits as well.

SUMMARY OF THE INVENTION

The invention provides compositions and methods for treating infection by positive stranded RNA viruses (such as HCV, HPV, Dengue and polio), by reducing the level or activity of the human host factor phosphatidylinositol 4-kinase, catalytic, beta polypeptide (PIK4CB; NM_002651), and/or phosphatidylinositol 4-kinase, catalytic, alpha polypeptide (PIK4CA; NM_002650) in cells where such viruses would replicate, such as the liver.

It is disclosed herein that proliferation of positive stranded RNA viruses can be inhibited by using double-stranded ribonucleic acid (dsRNA) to silence expression of the human host cell gene PIK4CB, and/or PIK4CA required for their proliferation.

The invention provides multiple embodiments, including in particular:

A double-stranded ribonucleic acid (dsRNA) for inhibiting the expression of phosphatidylinositol 4-kinase (PI4K) level or activity in a cell, wherein said dsRNA comprises at least two sequences that are complementary to each other and wherein a sense strand comprises a first sequence and an antisense strand comprises a second sequence comprising a region of complementarity which is substantially complementary to at least a part of a mRNA encoding PI4K, and wherein said region of complementarity is less than 30 nucleotides in length and wherein said dsRNA, upon contact with a cell expressing said PI4K gene, inhibits expression of said PIK4 gene. Such dsRNA may have chemical modifications, and may be conjugated to other moieties. In addition, such dsRNA may be provided in a pharmaceutical composition.

An embodied method is a method for inhibiting the expression of the phosphatidylinositol 4-kinase, catalytic, beta polypeptide (PIK4CB) gene or the phosphatidylinositol 4-kinase, catalytic, beta polypeptide (PIK4CA) gene in a cell, the method comprising:

(a) introducing into the cell a double-stranded ribonucleic acid (dsRNA), wherein the dsRNA comprises at least two sequences that are complementary to each other and wherein a sense strand comprises a first sequence and an antisense strand comprises a second sequence comprising a region of complementarity which is substantially complementary to at least a part of a mRNA encoding PIK4CB or PIK4CA, and wherein said region of complementarity is less than 30 nucleotides in length; and (b) maintaining the cell produced in step (a) for a time sufficient to obtain degradation of the mRNA transcript of the PIK4CB gene (or PIK4CA, as selected), thereby inhibiting expression or activity of PIK4CB (or PIK4CA, as selected) in the cell.

Alternatively, the invention embodies a method of treating a pathological processes mediated by positive stranded RNA virus infection comprising administering to a patient in need of such treatment, a dsRNA of the invention. The positive stranded RNA virus may be selected from among hepatitis C virus (HCV), human papilloma virus (HPV), and Dengue virus.

Alternative embodiments include a vector for inhibiting the expression of PIK4CB or PIK4CA in a cell; and cells comprising such vectors.

An alternative embodiment includes a method of treating an HCV infection comprising administering to a patient in need of such treatment a therapeutically effective amount of a pharmaceutical composition comprising a dsRNA of the invention.

BRIEF DESCRIPTION OF THE FIGURES

FIG. 1. Structure of the HCV constructs. A. The complete HCV genome. B. The subgenomic HCV replicon, used for the Clone A (subgenomic replicon) cells. The structural proteins are replaced with a neomycin resistance gene and a firefly luciferase reporter downstream of the 5' UTR. C. The reporter construct with the HCV proteins removed, used for the Clone Ar (cells lacking the subgenomic replicon) cells.

FIG. 8. Inhibition of HCV replication (live virus). Dose dependence of HCV replication upon treatment by the indicated siRNA. Cells are treated after HCV infection with indicated siRNA against either PIK4CA or PIK4CB. A) Effect on viral replication 24 hours after treatment with indicated siRNA (25 nM). Dark bars—viral luciferase (activity); Light bars—cell viability. Results are normalized to HCV replication upon GAPDH siRNA treatment. *Renilla* siRNA is positive control. B) Time dependence of HCV replication after treatment with indicated siRNA. Dark (first) bar—24 h; light (second) bar—48 h; white (third) bar—72 h; grey (fourth) bar—96 h.

DETAILED DESCRIPTION OF THE INVENTION

Figure 2:
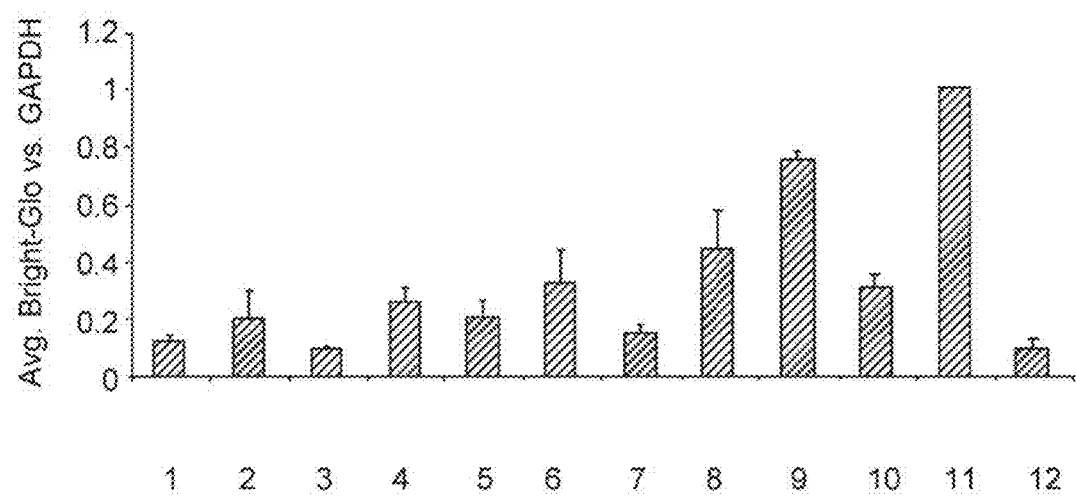
FIG. 2. Phenotype validation of siRNA hits. Hits from the large scale kinome siRNA screen re-analyzed. A. Results of testing dsRNA as individual duplexes PIK4CA1-PIK4CA4 (column 1-4) as a PIK4CA Smart Pool (col. 5), as individual duplexes PIK4CB1-PIK4CB4 (col. 6-9) or as a PIK4CB Smart Pool (Col. 10). Results are measured relative to GAPDH (control; column 11), Assay performed using 25 nM of dsRNA per well using Clone A cells; Bright-Glo activity measured at 72 hours post transfection. dsRNA targeting GAPDH (column 11) was used as the negative control and dsRNA targeting pGL2 (column 12) was the positive control.

The invention provides a solution to the problem of treating diseases associated with infection by positive stranded RNA viruses (such as HCV, HPV, Dengue and polio), by reducing the level of the human host factor phosphatidylinositol 4-kinase, catalytic, beta polypeptide (PIK4CB; NM_002651), and/or phosphatidylinositol 4-kinase, catalytic, alpha polypeptide (PIK4CA; NM_002650) in cells where such viruses would replicate. It is disclosed herein that proliferation of positive stranded RNA viruses can be inhibited by using double-stranded ribonucleic acid (dsRNA) to silence expression of the human host cell gene PIK4CB, and/or PIK4CA required for their proliferation.

In addition, it is disclosed herein for the first time that selected chemical modifications of these dsRNA are highly preferred embodiments which provide surprisingly reduced toxicity, reduced immunogenicity, improved pharmacological behaviour and other benefits.

The invention provides double-stranded ribonucleic acid (dsRNA), as well as compositions, pharmaceutical compositions and methods for inhibiting the propagation of positive stranded RNA viruses in a cell or mammal using the dsRNA. The invention also provides compositions and methods for treating pathological conditions and diseases in a mammal caused by infection from positive strand RNA viruses using dsRNA.

The dsRNA of the invention comprises an RNA strand (the antisense strand) having a region which is less than 30 nucleotides in length, generally 19-24 nucleotides in length, and is substantially complementary to at least part of the gene product (pre-mRNA or mature mRNA) transcript of human phosphatidylinositol 4-kinase, catalytic, beta subunit polypeptide (PIK4CB; NM_002651, and/or human phosphatidylinositol 4-kinase, catalytic, alpha polypeptide PIK4CA; NM_002650). The use of these dsRNAs enables the targeted degradation or inactivation of mRNAs of genes that are implicated in replication and or maintenance of positive stranded RNA infection in mammals. Using cell-based and animal assays, the present inventors have demonstrated that very low dosages of these dsRNA can specifically and efficiently mediate RNAi, resulting in significant inhibition of replication and infection. Thus, the methods and compositions of the invention comprising these dsRNAs are useful for treating pathological processes mediated by positive strand RNA virus infection.

Human phosphatidylinositol 4-kinase, catalytic, beta subunit polypeptide (PIK4CB; NM_002651; also sometimes called PI4KB; PI4B; pi4K92; PI4Kbeta; PI4K-BETA; PI4KIIIbeta), and human phosphatidylinositol 4-kinase, catalytic, alpha polypeptide (PIK4CA; NM_002650; also sometimes called PI4KA; PIK4A; pi4K230; FLJ16556; and PI4K-ALPHA) are phosphatidylinositol 4-kinases. Phosphatidylinositol 4-kinase is known alternatively as PI4K, PI 4-kinase or PIK4 in the literature. This specification uses such terms interchangeably unless context indicates a specific selection. There are four PI4K enzymes in mammalian cells which fall into two classes. The first is the type III PI4Ks, including PIK4CA and PIK4CB, conserved from yeast to man. The yeast orthologues Stt4p and Pik1p respectively are both essential genes with non-overlapping function. The type II PI4Ks, PI4KIIα and PI4K11β, distinct from the class III enzymes, also have a yeast homologue, LSB6, which is a nonessential gene. PIK4CB is the best characterized mammalian gene which is localized to the Golgi, functions in a complex with the small GTPase ADP-ribosylation factor (ARF), and is thought to regulate Golgi to plasma membrane secretion. The class II α and β enzymes have also been shown to be involved in Golgi/trans-Golgi trafficking. The class III α isoform seems to play a role at the plasma membrane and ER but not the Golgi.

In addition to the subcellular localization of the PI4Ks is the unique functions of the enzymes at the respective compartment. PIK4CB is involved in production of PtdIns4P and PtdIns4,5P2 pools, the regulated transport of ceramide from the ER to the Golgi, which leads to spingomyelin synthesis, and is involved in the structural integrity of the Golgi by maintaining the PI(4)P-rich domains that allow the docking of AP-1 machinery. Disruption of PIK4CB causes changes in the structure of the Golgi complex, causes secretory defects in polarized cells, and inhibits protein transport to the plasma membrane.

The class II and III PI4K α and β enzymes generate PtdIns 4-phosphate, the precursor of several regulatory phosphoinositides. These phosphoinositides control various cellular signalling and trafficking processes by recruiting regulatory proteins into organized signalling complexes. The production of PtdIns 4-phosphate [PtdIns4P] from PtdIns, the first step in the formation of PtdIns(4,5)P2 and PtdIns(3,4,5)P3. PtdIns(4,5)P2 is the main substrate of the phospholipase C (PLC) enzymes, yielding inositol 1,4,5-trisphosphate [Ins(1,4,5)P3] and diacylglycerol (DAG) involved in Ca' signaling. PtdIns(4,5)P2 also controls several types of ion channel and enzymes, such as phospholipase D (PLD), and interacts with proteins that link membranes to the actin cytoskeleton 3 and 5. PtdIns(3,4,5)P3, generated from PtdIns(4,5)P2 by the class I PtdIns 3-kinases, regulates a range of processes, such as cell metabolism and the antiapoptotic pathway via the serine/threonine kinase Akt but also controls tyrosine kinases, such as Btk and guanine exchange factors for small GTP-binding proteins. The production of these signaling phosphoinositides relies upon both the activity of their synthesizing enzymes and their precursor supply, thus PtdIns 4-kinases have a role in cellular regulation.

The positive strand RNA viruses of which are dependent on human PIK4CB or PIK4CA for replication are believed to include: I. Picorna- (HAV, polio, Coxsackie), noda-, como-, nepo-, poty-, bymo-, sobemoviruses, and luteoviruses (yellows, yellow drawf, and leafroll virus). II. Carmo-, tombus-, dianthoviruses, pestiviruses, toga-, echo-, Dengue, hepatitis C virus, flaviviruses. III. Tobamo-, tobra-, hordei-, tricorna-, alpha, rubi-, furoviruses, hepatitis E virus, potex-, carla-, tymoviruses, and apple chlorotic leaf spot virus.

The following detailed description discloses how to make and use the dsRNA and compositions containing dsRNA to inhibit the expression of positive-strand RNA viruses, as well as compositions and methods for treating diseases and disorders caused by positive-strand RNA virus infection, e.g. liver disease, liver failure, fibrosis, cancer, lung disease and its complications (described further below). The pharmaceutical compositions of the invention comprise a dsRNA having an antisense strand comprising a region of complementarity which is less than 30 nucleotides in length, generally 19-24 nucleotides in length, and is substantially complementary to at least part of an RNA transcript of PIK4CB and/or PIK4CA together with a pharmaceutically acceptable carrier. An embodiment of the invention is the employment of more than one dsRNA, optionally targeting different segments of the PIK4CB, and/or PIK4CA RNA transcript, in combination, in a pharmaceutical formulation.

Accordingly, certain aspects of the invention provide pharmaceutical compositions comprising the dsRNA of the invention together with a pharmaceutically acceptable carrier, methods of using the compositions to inhibit expression of PIK4CB, and/or PIK4CA and methods of using the pharmaceutical compositions to treat diseases caused by positive-strand RNA virus infection.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A" and "U" each generally stand for a nucleotide that contains guanine, cytosine, adenine, and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

As used herein, "target sequence" refers to a contiguous portion of the nucleotide sequence of an mRNA molecule formed during the transcription of PIK4CB, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes of the invention.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled.

The terms "complementary", "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide which is "substantially complementary to at least part of" a messenger RNA (mRNA) refers to a polynucleotide which is substantially complementary to a contiguous portion of the mRNA of interest (e.g., PIK4CB or PIK4CA). For example, a polynucleotide is complementary to at least a part of PIK4CB mRNA if the sequence is substantially complementary to a non-interrupted portion of an mRNA encoding PIK4CB. Similarly a polynucleotide is complementary to at least a part of PIK4CA mRNA if the sequence is substantially complementary to a non-interrupted portion of an mRNA encoding PIK4CA.

The term "double-stranded RNA" or "dsRNA", as used herein, refers to a complex of ribonucleic acid molecules, having a duplex structure comprising two anti-parallel and substantially complementary, as defined above, nucleic acid strands. The two strands forming the duplex structure may be different portions of one larger RNA molecule, or they may be separate RNA molecules. Where separate RNA molecules, such dsRNA are often referred to in the literature as siRNA ("short interfering RNA"). Where the two strands are part of one larger molecule, and therefore are connected by an uninterrupted chain of nucleotides between the 3'-end of one strand and the 5'end of the respective other strand forming the duplex structure, the connecting RNA chain is referred to as a "hairpin loop", "short hairpin RNA" or "shRNA". Where the two strands are connected covalently by means other than an uninterrupted chain of nucleotides between the 3'-end of one strand and the 5' end of the respective other strand forming the duplex structure, the connecting structure is referred to as a "linker". The RNA strands may have the same or a different number of nucleotides. The maximum number of base pairs is the number of nucleotides in the shortest strand of the dsRNA minus any overhangs that are present in the duplex. In addition to the duplex structure, a dsRNA may comprise one or more nucleotide overhangs. In addition, as used in this specification, "dsRNA" may include chemical modifications to ribonucleotides, internucleoside linkages, end-groups, caps, and conjugated moieties, including substantial modifications at multiple nucleotides and including all types of modifications disclosed herein or known in the art. Any such modifications, as used in an siRNA type molecule, are encompassed by "dsRNA" for the purposes of this specification and claims.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule. For clarity, chemical caps or non-nucleotide chemical moieties conjugated to the 3' end or 5' end of an siRNA are not considered in determining whether an siRNA has an overhang or is blunt ended.

The term "antisense strand" refers to the strand of a dsRNA which includes a region that is substantially complementary to a target sequence. This strand is also known as the "guide" sequence, and is used in the functioning RISC complex to guide the complex to the correct mRNA for cleavage. As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus. This use of "antisense", because it relates to an RNA compound, is different from antisense DNA compounds, which are a different though related field of nucleic acid therapeutic.

The term "sense strand," as used herein, refers to the strand of a dsRNA that includes a region that is substantially complementary to a region of the antisense strand. This strand is also known as the "anti-guide" sequence because it contains the same sequence of nucleotides as the target sequence and therefore binds specifically to the guide sequence.

"Introducing into a cell", when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell", wherein the cell is part of a living organism. In such instance, introduction into the cell will include the delivery to the organism. For example, for in vivo delivery, dsRNA can be injected into a tissue site or administered systemically. In vitro introduction into a cell includes methods known in the art such as electroporation and lipofection.

The terms "silence" and "inhibit the expression of", in as far as they refer to PIK4CB or PIK4CA, herein refer to the at least partial suppression of the expression of PIK4CB or PIK4CA in a cell treated with dsRNA targeting PIK4CB or PIK4CA, as manifested by a reduction of the amount of mRNA transcribed or available compared to normal (untreated) cells. This measurement may be determined by comparing mRNA levels in treated cells (which may be isolated from a first cell or group of cells which have been treated such that the expression of PIK4CB or PIK4CA is inhibited), as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to gene transcription, e.g. the amount of polypeptide, or the number of cells displaying a certain phenotype, e.g kinase activity specifically associated with PIK4CB or PIK4CA, or susceptibility to infection. In principle, gene silencing may be determined in any cell expressing the gene of interest, either constitutively or by genetic engineering, and by any appropriate assay. However, when a reference is needed in order to determine whether a given dsRNA inhibits the expression of the PIK4CB or PIK4CA by a certain degree and therefore is encompassed by the instant invention, the assay provided in the Examples below shall serve as such reference.

For example, in certain instances, expression of the PIK4CB or PIK4CA gene is inhibited, when it is suppressed by at least about 20%, 25%, 35%, or 50% by administration of the double-stranded RNA of the invention. In some embodiments, the PIK4CB or PIK4CA gene is suppressed by at least about 60%, 70%, or 80% by administration of the double-stranded oligonucleotide of the invention. In some embodiments, the PIK4CB or PIK4CA gene is suppressed by at least about 85%, 90%, or 95% by administration of the double-stranded oligonucleotide of the invention. The results in FIG. 2 demonstrate that each tested dsRNA targeted to PIK4CB (or PIK4CA) is effective to reduce the relative level of expression product in the HCV replicon assay from 10% to 90%. The results in FIG. 3 demonstrate that each tested dsRNA targeted to PIK4CB (or PIK4CA) is effective to reduce the level of PIK4CB (or PIK4CA) mRNA levels in a cell from 10% to 90%.

As used herein in the context of positive-strand RNA virus infection, the terms "treat", "treatment", and the like, refer to relief from or alleviation of pathological processes mediated by positive-strand RNA virus infection. Such description includes use of the therapeutic agents of the invention for prophylaxis or prevention of positive-strand RNA virus infection, and relief from symptoms or pathologies caused by positive-strand RNA virus infection. In the context of the present invention insofar as it relates to any of the other conditions recited herein below (other than pathological processes mediated by positive-strand RNA virus infection), the terms "treat", "treatment", and the like mean to relieve or alleviate at least one symptom associated with such condition, or to slow or reverse the progression of such condition.

As used herein, the phrases "therapeutically effective amount" and "prophylactically effective amount" refer to an amount that provides a therapeutic benefit in the treatment, prevention, or management of pathological processes mediated by positive-strand RNA virus infection or an overt symptom of pathological processes mediated by positive-strand RNA virus infection. The specific amount that is therapeutically effective can be readily determined by ordinary medical practitioner, and may vary depending on factors known in the art, such as, e.g. the type of pathological processes mediated by positive-strand RNA virus infection, the patient's history and age, the stage of pathological processes mediated by positive-strand RNA virus infection, and the administration of other anti-pathological agents.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of a dsRNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a vector has been introduced from which a dsRNA molecule may be expressed.

Double-Stranded Ribonucleic Acid (dsRNA)

In one embodiment, the invention provides double-stranded ribonucleic acid (dsRNA) molecules for inhibiting the expression of PIK4CB and/or PIK4CA, and thereby inhibiting positive-strand RNA virus replication or propagation, in a cell or mammal, wherein the dsRNA comprises an antisense strand comprising a region of complementarity which is complementary to at least a part of an mRNA formed in the expression of PIK4CB or PIK4CA, and wherein the region of complementarity is less than 30 nucleotides in length, generally 19-24 nucleotides in length, and wherein said dsRNA, upon contact with a cell expressing said PIK4CB or PIK4CA gene, inhibits the expression of said PIK4CB or PIK4CA gene by at least 10%, 25%, or 40%.

The dsRNA comprises two RNA strands that are sufficiently complementary to hybridize to form a duplex structure. One strand of the dsRNA (the antisense strand) comprises a region of complementarity that is substantially complementary, and generally fully complementary, to a target sequence, derived from the sequence of gene product of the PIK4CB or PIK4CA gene, the other strand (the sense strand) comprises a region which is complementary to the antisense strand, such that the two strands hybridize and form a duplex structure when combined under suitable conditions. Generally, the duplex structure is between 15 and 30, more generally between 18 and 25, yet more generally between 19 and 24, and most generally between 19 and 21 base pairs in length. Similarly, the region of complementarity to the target sequence is between 15 and 30, more generally between 18 and 25, yet more generally between 19 and 24, and most generally between 19 and 21 nucleotides in length. The dsRNA of the invention may be blunt ended (e.g. where each nucleotide on either strand has a nucleotide suitable for base-pairing on the other strand), or it may further comprise one or more single-stranded nucleotide overhang(s), commonly on the 3' end. The dsRNA can be synthesized by standard methods known in the art as further discussed below, e.g., by use of an automated DNA synthesizer, such as are commercially available from, for example, Biosearch, Applied Biosystems, Inc.

In specific embodiments, the dsRNA comprises, for targeting PIK4CB, a strand selected from the sense sequences of Table 1 and a second sequence selected from the group consisting of the antisense sequences of Table 1. Alternative agents that target elsewhere in the PIK4CB target sequence, e.g. slightly upstream or downstream from the agents identified in Table 1, can readily be determined using the sequence listed in Table 1, and the flanking mRNA or genomic sequence found at NCBI Accession No.: NM_002651.

In specific embodiments, the dsRNA comprises, for targeting PIK4CA, a strand selected from the sense sequences of Table 2 and a second sequence selected from the group consisting of the antisense sequences of Table 2. Alternative agents that target elsewhere in the PIK4CA target sequence, e.g. slightly upstream or downstream from the agents identified in Table 2, can readily be determined using the sequence listed in Table 2, and the flanking mRNA or genomic sequence found at NCBI Accession No.: NM_002650.

In further embodiments, the dsRNA comprises at least one duplex sequence selected from the duplex sequences provided in Table 1 or from Table 2. In other embodiments, the therapeutic agent may comprise two or more duplex sequences selected from Table 1 and/or from Table 2. Generally, each dsRNA comprises two oligonucleotide strands, wherein one oligonucleotide is described as the sense strand in the Table and the second oligonucleotide is described as the antisense strand in the same Table. Each Table provides a duplex name for each preferred dsRNA. Nucleotide bases are indicated using standard nucleotide notation.

TABLE 1

Duplex siRNA (dsRNA) targeting PIK4CB

| Duplex Name | Antisense Sequence (Guide Sequence) | SEQ ID No.: | Sense Sequence | SEQ ID No.: |
|---|---|---|---|---|
| PIK4CB1 | GGACGUGGGUGAUGCCAUUUUTT | 1 | AAAAUGGCAUCACCCACGUCCTT | 105 |
| PIK4CB2 | GGGAUGACCUUCGGCAAGAUUTT | 2 | AAUCUUGCCGAAGGUCAUCCCTT | 106 |
| PIK4CB3 | GAGAUCCGUUGCCUAGAUGUUTT | 3 | AACAUCUAGGCAACGGAUCUCTT | 107 |
| PIK4CB4 | GCACCGAGAGUAUUGAUAAUUTT | 4 | AAUUAUCAAUACUCUCGGUGCTT | 108 |

TABLE 1-continued

Duplex siRNA (dsRNA) targeting PIK4CB

| Duplex Name | Antisense Sequence (Guide Sequence) | SEQ ID No.: | Sense Sequence | SEQ ID No.: |
|---|---|---|---|---|
| PIK4CB5 | SMARTpool PIKC4B1-B4 | | PIK4CB1-B4 | |
| PIK4CB6 | UUAUCAAUACUCUCGGUGCTGTT | 5 | GCACCGAGAGUAUUGAUAATT | 109 |
| PIK4CB7 | UUGUACUCCAGGCUCCUUGGATT | 6 | CAAGGAGCCUGGAGUACAATT | 110 |
| PIK4CB8 | UUGGACACUGAGGCAUCCGTTTT | 7 | CGGAUGCCUCAGUGUCCAATT | 111 |
| PIK4CB9 | UAGUCAACCAAGUGUAAUCTGTT | 8 | GAUUACACUUGGUUGACUATT | 112 |
| PIK4CB10 | UUGGGCACAGUGCUGAAGCTGTT | 9 | GCUUCAGCACUGUGCCCAATT | 113 |
| PIK4CB11 | AUGGGUAAUACCACAUUCGGGTT | 10 | CGAAUGUGGUAUUACCCAUTT | 114 |
| PIK4CB12 | AAUCAUGCCACUAUCAGCCGATT | 11 | GGCUGAUAGUGGCAUGAUUTT | 115 |
| PIK4CB13 | UCUCGUUUGAAGGCUGUCGGGTT | 12 | CGACAGCCUUCAAACGAGATT | 116 |
| PIK4CB14 | UACCACAUGAUCCUUCGUGTTTT | 13 | CACGAAGGAUCAUGUGGUATT | 117 |
| PIK4CB15 | UAAUGCUCUGGCGGCAACGGTTT | 14 | CGUUGCCGCCAGAGCAUUATT | 118 |
| PIK4CB16 | AUCUUGUAUGGCUUGAUCCAATT | 15 | GGAUCAAGCCAUACAAGAUTT | 119 |
| PIK4CB17 | AUCACAUCCACAAACUCUGTGTT | 16 | CAGAGUUUGUGGAUGUGAUTT | 120 |
| PIK4CB18 | UUCUCCACUUUAGGGUUGCTGTT | 17 | GCAACCCUAAAGUGGAGAATT | 121 |
| PIK4CB19 | UGUCACAUGAUGCCGUUGGTGTT | 18 | CCAACGGCAUCAUGUGACATT | 122 |
| PIK4CB20 | UGAUAGACCGCAUACUGCCATTT | 19 | GGCAGUAUGCGGUCUAUCATT | 123 |
| PIK4CB21 | UUCCGAGCGGCAAUCAGCCCTTT | 20 | GGCUGAUUGCCGCUCGGAATT | 124 |
| PIK4CB22 | UUUCGAAUGGUGCUGGAGCCATT | 21 | GCUCCAGCACCAUUCGAAATT | 125 |
| PIK4CB23 | UGUACAUGUUAAGCAACUGGGTT | 22 | CAGUUGCUUAACAUGUACATT | 126 |
| PIK4CB24 | UCUACGGACCUCGUACUCCGATT | 23 | GGAGUACGAGGUCCGUAGATT | 127 |
| PIK4CB25 | UUCCAUUUCCCUUGGGUGGATTT | 24 | CCACCCAAGGGAAAUGGAATT | 128 |
| PIK4CB26 | UUCUCAGACAAGGGCCCUCUATT | 25 | GAGGGCCCUUGUCUGAGAATT | 129 |
| PIK4CB27 | UUGCCGAUCGCCAUCAGGGACTT | 26 | CCCUGAUGGCGAUCGGCAATT | 130 |
| PIK4CB28 | UGGAUCAUCUAGGCAACGGATTT | 27 | CCGUUGCCUAGAUGAUCCATT | 131 |
| PIK4CB29 | UUCCCAAAUGGACUGCAGUTGTT | 28 | ACUGCAGUCCAUUUGGGAATT | 132 |
| PIK4CB30 | UCCACUACUGUAUCUCCCAUGTT | 29 | UGGGAGAUACAGUAGUGGATT | 133 |
| PIK4CB31 | UAGGAAGUAAUCGAGCAAGGATT | 30 | CUUGCUCGAUUACUUCCUATT | 134 |
| PIK4CB32 | AAGAAUCUCAUUCAAUUUCCATT | 31 | GAAAUUGAAUGAGAUUCUUTT | 135 |
| PIK4CB33 | UAGCUUGGUCCCACGGGAGTGTT | 32 | CUCCCGUGGGACCAAGCUATT | 136 |
| PIK4CB34 | UUGAACAUGUCGCCAUCCAGGTT | 33 | UGGAUGGCGACAUGUUCAATT | 137 |
| PIK4CB35 | UCAAGUCCUAAGUACCGAGAATT | 34 | CUCGGUACUUAGGACUUGATT | 138 |
| PIK4CB36 | AUGACUGACAGGAGCCGCCAATT | 35 | GGCGGCUCCUGUCAGUCAUTT | 139 |
| PIK4CB37 | UGUUCAUCCCUCUUAGUGGCTTT | 36 | CCACUAAGAGGGAUGAACATT | 140 |
| PIK4CB38 | UUGGAGUUGAGGACAACAGCCIT | 37 | CUGUUGUCCUCAACUCCAATT | 141 |
| PIK4CB39 | AAUAAGAGGAUGGCCUGUGGATT | 38 | CACAGGCCAUCCUCUUAUUTT | 142 |
| PIK4CB40 | UGAUCCGCCGUACUUUCUCCTTT | 39 | GAGAAAGUACGGCGGAUCATT | 143 |
| PIK4CB41 | AAUUCCACAUGGCUAGGCCAGTT | 40 | GGCCUAGCCAUGUGGAAUUTT | 144 |

TABLE 1-continued

Duplex siRNA (dsRNA) targeting PIK4CB

| Duplex Name | Antisense Sequence (Guide Sequence) | SEQ ID No.: | Sense Sequence | SEQ ID No.: |
|---|---|---|---|---|
| PIK4CB42 | AUCUGACUUAGAGCGCUGGTGTT | 41 | CCAGCGCUCUAAGUCAGAUTT | 145 |
| PIK4CB43 | CUCAGUGGUGUAACUGCCGTGTT | 42 | CGGCAGUUACACCACUGAGTT | 146 |
| PIK4CB44 | UCAGCUUAAAGGCUGACGUCTTT | 43 | ACGUCAGCCUUUAAGCUGATT | 147 |
| PIK4CB45 | AAGCCGUCAUAGAGUUUGGTGTT | 44 | CCAAACUCUAUGACGGCUUTT | 148 |
| PIK4CB46 | UCCGUGAUGACACUUAGCAGGTT | 45 | UGCUAAGUGUCAUCACGGATT | 149 |
| PIK4CB47 | UCGCCUAUGUCAUCCACCGACTT | 46 | CGGUGGAUGACAUAGGCGATT | 150 |
| PIK4CB48 | UGGAAGGCCCGCCCUUCUCAGTT | 47 | GAGAAGGGCGGGCCUUCCATT | 151 |
| PIK4CB49 | AACUGGGAGAUGUUGUCACAGTT | 48 | GUGACAACAUCUCCCAGUUTT | 152 |
| PIK4CB50 | UAGAGACUGCCACGCCUCCATTT | 49 | GGAGGCGUGGCAGUCUCUATT | 153 |
| PIK4CB51 | UUGACCACUGGUUCAAUCATGTT | 50 | UGAUUGAACCAGUGGUCAATT | 154 |
| PIK4CB52 | UUAGGGUUGCUGGCUGUUCGTTT | 51 | GAACAGCCAGCAACCCUAATT | 155 |
| PIK4CB53 | UCUGUGGUCAGCUUAAAGGCTTT | 52 | CCUUAAGCUGACCACAGATT | 156 |
| PIK4CB54 | AUUAUCAAUACUCUCGGUGCTTT | 53 | CACCGAGAGUAUUGAUAAUTT | 157 |
| PIK4CB55 | UUGGUGAGGUACUGGAAGCCGTT | 54 | GCUUCCAGUACCUCACCAATT | 158 |
| PIK4CB56 | UGUAUGGCUUGAUCCAAAGGGTT | 55 | CUUUGGAUCAAGCCAUACATT | 159 |
| PIK4CB57 | UUGGAGUUAUACAGGUAUGAATT | 56 | CAUACCUGUAUAACUCCAATT | 160 |
| PIK4CB58 | UCGAGCUUCCAAGAAUCUCATTT | 57 | GAGAUUCUUGGAAGCUCGATT | 161 |
| PIK4CB59 | AAAGUUAAUGCUCUGGCGGCATT | 58 | CCGCCAGAGCAUUAACUUUTT | 162 |
| PIK4CB60 | UAUCAGCCGAAAUCACAAGAATT | 59 | CUUGUGAUUUCGGCUGAUATT | 163 |
| PIK4CB61 | UUGUCAUAGUUGGGCACAGTGTT | 60 | CUGUGCCCAACUAUGACAATT | 164 |
| PIK4CB62 | UCCGUAGCUUGGUCCCACGGGTT | 61 | CGUGGGACCAAGCUACGGATT | 165 |
| PIK4CB63 | UGAGGUUUCGAAUGGUGCUGGTT | 62 | AGCACCAUUCGAAACCUCATT | 166 |
| PIK4CB64 | UUGUAUGGCUUGAUCCAAAGGTT | 63 | TTUGGAUCAAGCCAUACAATT | 167 |
| PIK4CB65 | UAAGUACCGAGAACCUACUCTTT | 64 | AGUAGGUUCUCGGUACUUATT | 168 |
| PIK4CB66 | UUUCCGAGCGGCAAUCAGCCCTT | 65 | GCUGAUUGCCGCUCGGAAATT | 169 |
| PIK4CB67 | UGAGGUACUGGAAGCCGUCATTT | 66 | GACGGCUUCCAGUACCUCATT | 170 |
| PIK4CB68 | UCUCAGACAAGGGCCCUCUAGTT | 67 | AGAGGGCCCUUGUCUGAGATT | 171 |
| PIK4CB69 | UGUAGGCUUGUACUCCAGGCTTT | 68 | CCUGGAGUACAAGCCUACATT | 172 |
| PIK4CB70 | UUAAUGCUCUGGCGGCAACGGTT | 69 | GUUGCCGCCAGAGCAUUAATT | 173 |
| PIK4CB71 | GAAUUAUCAAUACUCUCGGTGTT | 70 | CCGAGAGUAUUGAUAAUUCTT | 174 |
| PIK4CB72 | UUCCACAUGGCUAGGCCAGTATT | 71 | CUGGCCUAGCCAUGUGGAATT | 175 |
| PIK4CB73 | UGAGGCAUCCGUUCAUACCTCTT | 72 | GGUAUGAACGGAUGCCUCATT | 176 |
| PIK4CB74 | UUGCUGGCUGUUCGUUUCAGGTT | 73 | UGAAACGAACAGCCAGCAATT | 177 |
| PIK4CB75 | AACAUGUCGCCAUCCAGGCCGTT | 74 | GCCUGGAUGGCGACAUGUUTT | 178 |
| PIK4CB76 | UGCUCCGGAGUAGUCAACCAATT | 75 | GGUUGACUACUCCGGAGCATT | 179 |
| PIK4CB77 | ACUGGUUCAAUCAUGCCACUATT | 76 | GUGGCAUGAUUGAACCAGUTT | 180 |
| PIK4CB78 | UAGACCGCAUACUGCCAUCCATT | 77 | GAUGGCAGUAUGCGGUCUATT | 181 |

TABLE 1-continued

Duplex siRNA (dsRNA) targeting PIK4CB

| Duplex Name | Antisense Sequence (Guide Sequence) | SEQ ID No.: | Sense Sequence | SEQ ID No.: |
|---|---|---|---|---|
| PIK4CB79 | UGGAGUUGAGGACAACAGCCTTT | 78 | GCUGUUGUCCUCAACUCCATT | 182 |
| PIK4CB80 | UAGUUGGGCACAGUGCUGAAGTT | 79 | UCAGCACUGUGCCCAACUATT | 183 |
| PIK4CB81 | UCAAUACUCUCGGUGCUGGAGTT | 80 | CCAGCACCGAGAGUAUUGATT | 184 |
| PIK4CB82 | UACUCCGAAUUCGGUUCUCGGTT | 81 | GAGAACCGAAUUCGGAGUATT | 185 |
| PIK4CB83 | UUACCACAUGAUCCUUCGUGTTT | 82 | ACGAAGGAUCAUGUGGUAATT | 186 |
| PIK4CB84 | UGGCUAGGCCAGUACCCUCAGTT | 83 | GAGGGUACUGGCCUAGCCATT | 187 |
| PIK4CB85 | UUCUACGGACCUCGUACUCCGTT | 84 | GAGUACGAGGUCCGUAGAATT | 188 |
| PIK4CB86 | UGACAGGAGCCGCCAAUUGGGTT | 85 | CAAUUGGCGGCUCCUGUCATT | 189 |
| PIK4CB87 | UCAGACAAGGGCCCUCUAGGGTT | 86 | CUAGAGGGCCCUUGUCUGATT | 190 |
| PIK4CB88 | AUUGACCACUGGUUCAAUCATTT | 87 | GAUUGAACCAGUGGUCAAUTT | 191 |
| PIK4CB89 | UCCGGAGUAGUCAACCAAGUGTT | 88 | CUUGGUUGACUACUCCGGATT | 192 |
| PIK4CB90 | UCAUGGGUAAUACCACAUUCGTT | 89 | AAUGUGGUAUUACCCAUGATT | 193 |
| PIK4CB91 | UUCAAUCAUGCCACUAUCAGCTT | 90 | UGAUAGUGGCAUGAUUGAATT | 194 |
| PIK4CB92 | UCUAGGCAACGGAUCUCACTGTT | 91 | GUGAGAUCCGUUGCCUAGATT | 195 |
| PIK4CB93 | UGAUCUGGGCAGGUGGAUCATTT | 92 | GAUCCACCUGCCCAGAUCATT | 196 |
| PIK4CB94 | UAUCAAUACUCUCGGUGCUGGIT | 93 | AGCACCGAGAGUAUUGAUATT | 197 |
| PIK4CB95 | AAUGCUCUGGCGGCAACGGIGTT | 94 | CCGUUGCCGCCAGAGCAUUTT | 198 |
| PIK4CB96 | UCCCACGGGAGUGUCGUUGAGTT | 95 | CAACGACACUCCCGUGGGATT | 199 |
| PIK4CB97 | UUUCUCAGACAAGGGCCCUCTTT | 96 | AGGGCCCUUGUCUGAGAAATT | 200 |
| PIK4CB98 | AUCUUCUGGGUCUCGUUUGAATT | 97 | CAAACGAGACCCAGAAGAUTT | 201 |
| PIK4CB99 | UCGUACUCCGAAUUCGGUUCTTT | 98 | AACCGAAUUCGGAGUACGATT | 202 |
| PIK4CB100 | UUUAGGGUUGCUGGCUGUUCGTT | 99 | AACAGCCAGCAACCCUAAATT | 203 |
| PIK4CB101 | CUCCUGUAGGAAGUAAUCGAGTT | 100 | CGATTACUUCCUACAGGAGTT | 204 |
| PIK4CB102 | UGGUGAGGUACUGGAAGCCGTTT | 101 | GGCUUCCAGUACCUCACCATT | 205 |
| PIK4CB103 | UCAUCCACCGACCAGGCCUCATT | 102 | AGGCCUGGUCGGUGGAUGATT | 206 |
| PIK4CB104 | ACUCCGAAUUCGGUUCUCGGGTT | 103 | CGAGAACCGAAUUCGGAGUTT | 207 |
| PIK4CB105 | UCAGGUAGGGAGCCUUGUCCTTT | 104 | GACAAGGCUCCCUACCUGATT | 208 |

TABLE 2

Duplex siRNA (dsRNA) targeting PIK4CA

| Duplex Name | Antisense Sequence (Guide Sequence) | SEQ ID No.: | Sense Sequence | SEQ ID No.: |
|---|---|---|---|---|
| PIK4CA1 | GAGCAUCUCUCCCUACCUAUUTT | 209 | AAUAGGUAGGGAGAGAUGCUCTT | 313 |
| PIK4CA2 | GUGAAGCGAUGUGGAGUUAUUTT | 210 | AAUAACUCCACAUCGCUUCACTT | 314 |
| PIK4CA3 | CCACAGGCCUCUCCUACUUUTUTT | 211 | AAAAGUAGGAGAGGCCUGUGGTT | 315 |
| PIK4CA4 | GCAGAAAUUUGGCCUGUUUUUTT | 212 | AAAACAGGCCAAAUUUCUGCTT | 316 |

TABLE 2-continued

Duplex siRNA (dsRNA) targeting PIK4CA

| Duplex Name | Antisense Sequence (Guide Sequence) | SEQ ID No.: | Sense Sequence | SEQ ID No.: |
|---|---|---|---|---|
| PIK4CA5 | SMARTpool, PIK4CA1-A4 | | PIK4CA1-A4 | |
| PIK4CA6 | UUCUUAUCUGAGAACAUGGCGTT | 213 | CCAUGUUCUCAGAUAAGAATT | 317 |
| PIK4CA7 | UUUGGGUUGACUUGCUUCCGATT | 214 | GGAAGCAAGUCAACCCAAATT | 318 |
| PIK4CA8 | UAGAAGAGGAUGGCGUCCGGATT | 215 | CGGACGCCAUCCUCUUCUATT | 319 |
| PIK4CA9 | UAUGUGUUGAUCCAGCCUUGGTT | 216 | AAGGCUGGAUCAACACAUATT | 320 |
| PIK4CA10 | UUGAACUUGGCCAGAUAUGGGTT | 217 | CAUAUCUGGCCAAGUUCAATT | 321 |
| PIK4CA11 | AUGAUAGCCGACACGUUGGTGTT | 218 | CCAACGUGUCGGCUAUCAUTT | 322 |
| PIK4CA12 | UUCAGGCACAUCACUAACGGCTT | 219 | CGUUAGUGAUGUGCCUGAATT | 323 |
| PIK4CA13 | UUCGGAUGAAGUUGUAGCGGGTT | 220 | CGCUACAACUUCAUCCGAATT | 324 |
| PIK4CA14 | UUCAAGUUCACUAACUCCACATT | 221 | UGGAGUUAGUGAACUUGAATT | 325 |
| PIK4CA15 | UCAUCCUCGGAGUCUGAGCGGTT | 222 | GCUCAGACUCCGAGGAUGATT | 326 |
| PIK4CA16 | UUUCUGCUCCACCGUCAUGTGTT | 223 | CAUGACGGUGGAGCAGAAATT | 327 |
| PIK4CA17 | AGGAAUGUUAGCUCCUCUGTGTT | 224 | CAGAGGAGCUAACAUUCCUTT | 328 |
| PIK4CA18 | AAGUAGUCAAAGGCAGUGGAGTT | 225 | CCACUGCCUUUGACUACUUTT | 329 |
| PIK4CA19 | UUCACUUCAGACAGGGCCGACTT | 226 | CGGCCCUGUCUGAAGUGAATT | 330 |
| PIK4CA20 | UUGUAGUCGAUGUCCAGCACATT | 227 | UGCUGGACAUCGACUACAATT | 331 |
| PIK4CA21 | UUCGUUCCCAAUGGCUUCUGTTT | 228 | AGAAGCCAUUGGGAACGAATT | 332 |
| PIK4CA22 | UCGGCGUCGAUGGUGUGCCAGTT | 229 | GGCACACCAUCGACGCCGATT | 333 |
| PIK4CA23 | AAAGAGGUCCAGGCCGACCAGTT | 230 | GGUCGGCCUGGACCUCUUUTT | 334 |
| PIK4CA24 | UUAGAUCUCCAGUUGGCCACGTT | 231 | UGGCCAACUGGAGAUCUAATT | 335 |
| PIK4CA25 | UGUGAUCUCCUCUACCAACTGTT | 232 | GUUGGUAGAGGAGAUCACATT | 336 |
| PIK4CA26 | UUGGUCAGAGCUGCAGUACTTTT | 233 | GUACUGCAGCUCUGACCAATT | 337 |
| PIK4CA27 | UGAUGCUUAUGUCUUCACGCATT | 234 | CGUGAAGACAUAAGCAUCATT | 338 |
| PIK4CA28 | AUUUGGAACCACAUCGGCATGTT | 235 | UGCCGAUGUGGUUCCAAAUTT | 339 |
| PIK4CA29 | UCCCGGGUCCAACCGAACGAGTT | 236 | CGUUCGGUUGGACCCGGGATT | 340 |
| PIK4CA30 | UCUGCUUCCUUUAUCUCAGCATT | 237 | CUGAGAUAAAGGAAGCAGATT | 341 |
| PIK4CA31 | AAGUCGAUCCAGAUGUAGUGGTT | 238 | ACUACAUCUGGAUCGACUUTT | 342 |
| PIK4CA32 | AAGAGGUCGAUGAUCUGCAGGTT | 239 | UGCAGAUCAUCGACCUCUUTT | 343 |
| PIK4CA33 | AGAGCCGACAGUUAUGUCCAGTT | 240 | GGACAUAACUGUCGGCUCUTT | 344 |
| PIK4CA34 | UCCUUGAGUAGGGAACUUUGGTT | 241 | AAAGUUCCCUACUCAAGGATT | 345 |
| PIK4CA35 | UCCGGCCUGGUCUAGUUCCAGTT | 242 | GGAACUAGACCAGGCCGGATT | 346 |
| PIK4CA36 | UGUGAUGAGACGCUCGAUCTCTT | 243 | GAUCGAGCGUCUCAUCACATT | 347 |
| PIK4CA37 | AAGUAGGAGAGGCCUGUGGGTTT | 244 | CCACAGGCCUCUCCUACUUTT | 348 |
| PIK4CA38 | UCCGGGUGUCCUGAUUAUCUGTT | 245 | GAUAAUCAGGACACCCGGATT | 349 |
| PIK4CA39 | GAGAUGGUGGACAUGCCGCUGTT | 246 | GCGGCAUGUCCACCAUCUCTT | 350 |
| PIK4CA40 | UGCCUGCCAGGAGAUCUUCUGTT | 247 | GAAGAUCUCCUGGCAGGCATT | 351 |
| PIK4CA41 | CUUCUCGCGAAGCACAUUGCGTT | 248 | CAAUGUGCUUCGCGAGAAGTT | 352 |

TABLE 2-continued

Duplex siRNA (dsRNA) targeting PIK4CA

| Duplex Name | Antisense Sequence (Guide Sequence) | SEQ ID No.: | Sense Sequence | SEQ ID No.: |
|---|---|---|---|---|
| PIK4CA42 | UGCACGGCUAGGUAGGGAGAGUU | 249 | CUCCCUACCUAGCCGUGCAUU | 353 |
| PIK4CA43 | UCUCCCGCAUGAACUACAGGUUU | 250 | CUGUAGUUCAUGCGGGAGAUU | 354 |
| PIK4CA44 | AGAAAUCAAACUCCCGCUGGUUU | 251 | CAGCGGGAGUUUGAUUUCUUU | 355 |
| PIK4CA45 | UUAUCUGAGAACAUGGCGGUCUU | 252 | CCGCCAUGUUCUCAGAUAAUU | 356 |
| PIK4CA46 | UUGGGUUGACUUGCUUCCGAGUU | 253 | CGGAAGCAAGUCAACCCAAUU | 357 |
| PIK4CA47 | UCUUAUCUGAGAACAUGGCGGUU | 254 | GCCAUGUUCUCAGAUAAGAUU | 358 |
| PIK4CA48 | UCUGAGAACAUGGCGGUCCAAUU | 255 | GGACCGCCAUGUUCUCAGAUU | 359 |
| PIK4CA49 | UUGCUUCCGAGGCAGCCAGGGUU | 256 | CUGGCUGCCUCGGAAGCAAUU | 360 |
| PIK4CA50 | UCAAGUUCACUAACUCCACAUUU | 257 | GUGGAGUUAGUGAACUUGAUU | 361 |
| PIK4CA51 | AUCUCCACUUGGUCAGAGCUGUU | 258 | GCUCUGACCAAGUGGAGAUUU | 362 |
| PIK4CA52 | AACGAGACGGGUCACUUCGUUUU | 259 | CGAAGUGACCCGUCUCGUUUU | 363 |
| PIK4CA53 | UGUGUUGAUCCAGCCUUGGGUUU | 260 | CCAAGGCUGGAUCAACACAUU | 364 |
| PIK4CA54 | UUCUGCUCCACCGUCAUGUGCUU | 261 | ACAUGACGGUGGAGCAGAAUU | 365 |
| PIK4CA55 | UGGAGCAUCGGCGUCGAUGGUUU | 262 | CAUCGACGCCGAUGCUCCAUU | 366 |
| PIK4CA56 | UCGAUGUCCAGCACAAUGGCCUU | 263 | CCAUUGUGCUGGACAUCGAUU | 367 |
| PIK4CA57 | UCGUUCCCAAUGGCUUCUGUGUU | 264 | CAGAAGCCAUUGGGAACGAUU | 368 |
| PIK4CA58 | UAACUCCACAUCGCUUCACCUUU | 265 | GUGAAGCGAUGUGGAGUUAUU | 369 |
| PIK4CA59 | UGAUCUCCUCUACCAACUGAUUU | 266 | CAGUUGGUAGAGGAGAUCAUU | 370 |
| PIK4CA60 | UUGGCGAUCUCAAACCGCUGCUU | 267 | AGCGGUUUGAGAUCGCCAAUU | 371 |
| PIK4CA61 | AUGUGUUGAUCCAGCCUUGGGIT | 268 | CAAGGCUGGAUCAACACAUUU | 372 |
| PIK4CA62 | CUGAUGUACUUAGAUCUCCAGUU | 269 | GGAGAUCUAAGUACAUCAGUU | 373 |
| PIK4CA63 | UGGAGUAGAUCUUCUCGCGAAUU | 270 | CGCGAGAAGAUCUACUCCAUU | 374 |
| PIK4CA64 | UCAGGCACAUCACUAACGGCUUU | 271 | CCGUUAGUGAUGUGCCUGAUU | 375 |
| PIK4CA65 | UAGGCGGCCAUGCUUCGGAUGUU | 272 | UCCGAAGCAUGGCCGCCUAUU | 376 |
| PIK4CA66 | GAUGCUUAUGUCUUCACGCAGUU | 273 | GCGUGAAGACAUAAGCAUCUU | 377 |
| PIK4CA67 | UCUCCAGUUGGCCACGCUGUUUU | 274 | CAGCGUGGCCAACUGGAGAUU | 378 |
| PIK4CA68 | UGAAGUUGUAGCGGGCCUGCUUU | 275 | CAGGCCCGCUACAACUUCAUU | 379 |
| PIK4CA69 | UGAGCUCUGGAGCAUCGGCGUUU | 276 | GCCGAUGCUCCAGAGCUCAUU | 380 |
| PIK4CA70 | AAGGAAUGUUAGCUCCUCUGUUU | 277 | AGAGGAGCUAACAUUCCUUUU | 381 |
| PIK4CA71 | UGUUCUUAAACCUGGCAGGCAUU | 278 | CCUGCCAGGUUUAAGAACAUU | 382 |
| PIK4CA72 | AUGUCCAGCACAAUGGCCUCAUU | 279 | AGGCCAUUGUGCUGGACAUUU | 383 |
| PIK4CA73 | UACAGAAGGAAUGUUAGCUCCUU | 280 | AGCUAACAUUCCUUCUGUAUU | 384 |
| PIK4CA74 | AAGAUCUCCACUUGGUCAGAGUU | 281 | CUGACCAAGUGGAGAUCUUUU | 385 |
| PIK4CA75 | UCACUUCGUUCCCAAUGGCUUUU | 282 | GCCAUUGGGAACGAAGUGAUU | 386 |
| PIK4CA76 | UGAGACGCUCGAUCUCAGUGGUU | 283 | ACUGAGAUCGAGCGUCUCAUU | 387 |
| PIK4CA77 | UGGCGAUCUCAAACCGCUGCAUU | 284 | CAGCGGUUUGAGAUCGCCAUU | 388 |
| PIK4CA78 | UGCCAGGUGACCAGGAACUGUUU | 285 | AGUUCCUGGUCACCUGGCAUU | 389 |

TABLE 2-continued

Duplex siRNA (dsRNA) targeting PIK4CA

| Duplex Name | Antisense Sequence (Guide Sequence) | SEQ ID No.: | Sense Sequence | SEQ ID No.: |
|---|---|---|---|---|
| PIK4CA79 | UACUUAGAUCUCCAGUUGGCCTT | 286 | CCAACUGGAGAUCUAAGUATT | 390 |
| PIK4CA80 | CUUAUCUGAGAACAUGGCGGTTT | 287 | CGCCAUGUUCUCAGAUAAGTT | 391 |
| PIK4CA81 | UCCACAUCGCUUCACCUUGAATT | 288 | CAAGGUGAAGCGAUGUGGATT | 392 |
| PIK4CA82 | UCGGAUGAAGUUGUAGCGGGCTT | 289 | CCGCUACAACUUCAUCCGATT | 393 |
| PIK4CA83 | AGUGGAGUAGAUCUUCUCGCGTT | 290 | CGAGAAGAUCUACUCCACUTT | 394 |
| PIK4CA84 | CUUCGUUCCCAAUGGCUUCTGTT | 291 | GAAGCCAUUGGGAACGAAGTT | 395 |
| PIK4CA85 | AAGAGGAUGGCGUCCGGAGGGTT | 292 | CUCCGGACGCCAUCCUCUUTT | 396 |
| PIK4CA86 | GUGGAGUAGAUCUUCUCGCGATT | 293 | GCGAGAAGAUCUACUCCACTT | 397 |
| PIK4CA87 | AGACGGGUCACUUCGUUCCCATT | 294 | GGAACGAAGUGACCCGUCUTT | 398 |
| PIK4CA88 | AGGAAGUCGAUCCAGAUGUAGTT | 295 | ACAUCUGGAUCGACUUCCUTT | 399 |
| PIK4CA89 | UUUGGAACCACAUCGGCAUGCTT | 296 | AUGCCGAUGUGGUUCCAAATT | 400 |
| PIK4CA90 | UGAUGAGACGCUCGAUCUCAGTT | 297 | GAGAUCGAGCGUCUCAUCATT | 401 |
| PIK4CA91 | CUGUAGGCGGCCAUGCUUCGGTT | 298 | GAAGCAUGGCCGCCUACAGTT | 402 |
| PIK4CA92 | UCUCAAACCGCUGCACCAGGATT | 299 | CUGGUGCAGCGGUUUGAGATT | 403 |
| PIK4CA93 | AAGGAGCCUGUGAUCUCCUCTTT | 300 | AGGAGAUCACAGGCUCCUUTT | 404 |
| PIK4CA94 | AGCUGAAGUAGUCAAAGGCAGTT | 301 | GCCUUUGACUACUUCAGCUTT | 405 |
| PIK4CA95 | AUGAGACGCUCGAUCUCAGTGTT | 302 | CUGAGAUCGAGCGUCUCAUTT | 406 |
| PIK4CA96 | UUCCCAAUGGCUUCUGUGUTCTT | 303 | ACACAGAAGCCAUUGGGAATT | 407 |
| PIK4CA97 | UGUCCAGCACAAUGGCCUCAGTT | 304 | GAGGCCAUUGUGCUGGACATT | 408 |
| PIK4CA98 | UGGGUUGACUUGCUUCCGAGGTT | 305 | UCGGAAGCAAGUCAACCCATT | 409 |
| PIK4CA99 | ACUAACUCCACAUCGCUUCACTT | 306 | GAAGCGAUGUGGAGUUAGUTT | 410 |
| PIK4CA100 | UGGUCAGAGCUGCAGUACUTGTT | 307 | AGUACUGCAGCUCUGACCATT | 411 |
| PIK4CA101 | CCUGAUUUCUUGGAGAUGGTGTT | 308 | CCAUCUCCAAGAAAUCAGGIT | 412 |
| PIK4CA102 | UAGUCGAUGUCCAGCACAATGTT | 309 | UUGUGCUGGACAUCGACUATT | 413 |
| PIK4CA103 | AAGUUGUAGCGGGCCUGCUGGTT | 310 | AGCAGGCCCGCUACAACUUTT | 414 |
| PIK4CA104 | UGCACUCAUCCUCGGAGUCTGTT | 311 | GACUCCGAGGAUGAGUGCATT | 415 |
| PIK4CA105 | AUCUCCCGCAUGAACUACAGGTT | 312 | UGUAGUUCAUGCGGGAGAUTT | 416 |

The skilled person is well aware that dsRNAs comprising a duplex structure of between 20 and 23, but specifically 21, base pairs have been recognized as particularly effective in inducing RNA interference (Elbashir et al., EMBO 2001, 20:6877-6888). However, others have found that shorter or longer dsRNAs can be effective as well. In the embodiments described above, by virtue of the nature of the oligonucleotide sequences provided in Table 1 or Table 2, the dsRNAs of the invention can comprise at least one strand of a length of minimally 21 nt. It can be reasonably expected that shorter dsRNAs comprising one of the sequences of Table 1 or Table 2 minus only a few nucleotides on one or both ends may be similarly effective as compared to the dsRNAs described above. Hence, dsRNAs comprising a partial sequence of at least 15, 16, 17, 18, 19, 20, or more contiguous nucleotides from one of the sequences of Table 1 or Table 2 and differing in their ability to inhibit the expression of the PIK4CB or PIK4CA gene in a FACS assay or other assay as described herein below by not more than 5, 10, 15, 20, 25, or 30% inhibition from a dsRNA comprising the full sequence, are contemplated by the invention. Further dsRNAs that cleave within the target sequence provided in Table 1 or Table 2 can readily be made using the reference sequence and the target sequence provided.

In addition, the RNAi agents provided in Table 1 or Table 2 identify a useful site in the PIK4CB or PIK4CA mRNA that is particularly susceptible to RNAi based cleavage. As such the present invention further includes RNAi agents that target within the sequence targeted by one of the agents of the present invention. As used herein a second RNAi agent is said to target within the sequence of a first RNAi agent if the second RNAi agent cleaves the message anywhere within the mRNA that is complementary to the antisense strand of the first RNAi agent. Such a second agent will generally consist of at least 15 contiguous nucleotides from one of the sequences provided in Table 1 or Table 2 coupled to additional nucleotide sequences taken from the region contiguous to the selected sequence in the target gene. For example, the last 15 nucleotides of SEQ ID NO: 5 combined with the next 6 nucleotides from the PIK4CB gene would produce a single strand agent of 21 nucleotides that is based on one of the sequences provided in Table 1. Based on this single strand, a complementary sense strand could be easily generated. It would cleave the target mRNA in the same sensitivity region as the original SEQ ID NO: 5 duplex. The same could be done for PIK4CA based on sequences provided in Table 2.

The dsRNA of the invention can contain one or more mismatches to the target sequence. In a preferred embodiment, the dsRNA of the invention contains no more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide dsRNA strand which is complementary to a region of the PIK4CB target gene, the dsRNA generally does not contain any mismatch within the central 13 nucleotides. The methods described within the invention can be used to determine whether a dsRNA containing a mismatch to a target sequence is effective in reducing expression of PIK4CB in a cell. Consideration of the efficacy of dsRNAs with mismatches in inhibiting expression of PIK4CB is important, especially if the particular region of complementarity in PIK4CB is known to have polymorphic sequence variation in humans. The same analysis can be made for dsRNA targeting PIK4CA.

In one embodiment, at least one end of the dsRNA has a single-stranded nucleotide overhang of 1 to 4, generally 1 or 2 nucleotides. dsRNAs having at least one nucleotide overhang have unexpectedly superior inhibitory properties than their blunt-ended counterparts. Moreover, the presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The dsRNA may also have a blunt end, generally located at the 5'-end of the antisense strand. Such dsRNAs have improved stability and inhibitory activity, thus allowing administration at low dosages, i.e., less than 5 mg/kg body weight of the recipient per day. Generally, the antisense strand of the dsRNA has a nucleotide overhang at the 3'-end. In another embodiment, one or more of the nucleotides in the overhang is replaced with a nucleoside thiophosphate.

In Table 1 and Table 2, matched pairs of RNA strands are shown having two thymidine DNA nucleotides on the 3' end. This T-T motif is illustrated because it is a commonly used motif which tends to lend stability or other desirable properties to siRNA. Thus T-T is a suitable embodiment of the invention. Nonetheless, it is well known by those skilled in the art that other arrangements of nucleotides, optionally with modified internucleoside linkages, chemical modifications or protective caps can be employed on the 3' end of an siRNA strand. Those skilled in the art know that such modifications lead to improved functionally equivalent molecules because the target sequence of the mRNA remains the same, but the changed overhanging nucleotides may favourably influence other pharmacological behaviour.

In yet another embodiment, the dsRNA is chemically modified to enhance stability or provide other therapeutic benefits. The nucleic acids of the invention may be synthesized and/or modified by methods well established in the art, such as those described in "Current protocols in nucleic acid chemistry", Beaucage, S. L. et al. (Edrs.), John Wiley & Sons, Inc., New York, N.Y., USA, which is hereby incorporated herein by reference. Chemical modifications may include, but are not limited to 2' modifications, modifications at other sites of the sugar or base of an oligonucleotide, introduction of non-natural bases into the olibonucleotide chain, covalent attachment to a ligand or chemical moiety, and replacement of internucleotide phosphate linkages with alternate linkages such as thiophosphates. More than one such modification may be employed.

Chemical linking of the two separate dsRNA strands may be achieved by any of a variety of well-known techniques, for example by introducing covalent, ionic or hydrogen bonds; hydrophobic interactions, van der Waals or stacking interactions; by means of metal-ion coordination, or through use of purine analogues. Generally, the chemical groups that can be used to modify the dsRNA include, without limitation, methylene blue; bifunctional groups, generally bis-(2-chloroethyl)amine; N-acetyl-N'-(p-glyoxylbenzoyl)cystamine; 4-thiouracil; and psoralen. In one embodiment, the linker is a hexa-ethylene glycol linker. In this case, the dsRNA are produced by solid phase synthesis and the hexa-ethylene glycol linker is incorporated according to standard methods (e.g., Williams, D. J., and K. B. Hall, *Biochem.* (1996) 35:14665-14670). In a particular embodiment, the 5'-end of the antisense strand and the 3'-end of the sense strand are chemically linked via a hexaethylene glycol linker. In another embodiment, at least one nucleotide of the dsRNA comprises a phosphorothioate or phosphorodithioate groups. The chemical bond at the ends of the dsRNA is generally formed by triple-helix bonds. Table 1 and Table 2 provide examples of dsRNA sequences that could be modified according to these techniques.

In yet another embodiment, the nucleotides at one or both of the two single strands may be modified to prevent or inhibit the degradation activities of cellular enzymes, such as, for example, without limitation, certain nucleases. Techniques for inhibiting the degradation activity of cellular enzymes against nucleic acids are known in the art including, but not limited to, 2'-amino modifications, 2'-amino sugar modifications, 2'-F sugar modifications, 2'-F modifications, 2'-alkyl sugar modifications, uncharged backbone modifications, morpholino modifications, 2'-O-methyl modifications, and phosphoramidate (see, e.g., Wagner, *Nat. Med.* (1995) 1:1116-8). Thus, at least one 2'-hydroxyl group of the nucleotides on a dsRNA is replaced by a chemical group, generally by a 2'-amino or a 2'-methyl group. Also, at least one nucleotide may be modified to form a locked nucleotide. Such locked nucleotide contains a methylene bridge that connects the 2'-oxygen of ribose with the 4'-carbon of ribose. Oligonucleotides containing the locked nucleotide are described in Koshkin, A. A., et al., Tetrahedron (1998), 54: 3607-3630) and Obika, S. et al., *Tetrahedron Lett.* (1998), 39: 5401-5404). Introduction of a locked nucleotide into an oligonucleotide improves the affinity for complementary sequences and increases the melting temperature by several degrees (Braasch, D. A. and D. R. Corey, *Chem. Biol.* (2001), 8:1-7).

Conjugating a ligand to a dsRNA can enhance its cellular absorption as well as targeting to a particular tissue or uptake by specific types of cells. In certain instances, a hydrophobic ligand is conjugated to the dsRNA to facilitate direct permeation of the cellular membrane. Alternatively, the ligand conjugated to the dsRNA is a substrate for receptor-mediated endocytosis. These approaches have been used to facilitate cell permeation of antisense oligonucleotides as well as dsRNA agents. For example, cholesterol has been conjugated to various antisense oligonucleotides resulting in compounds that are substantially more active compared to their non-conjugated analogs. See M. Manoharan *Antisense & Nucleic Acid Drug Development* 2002, 12, 103. Other lipophilic compounds that have been conjugated to oligonucleotides include 1-pyrene butyric acid, 1,3-bis-O-(hexadecyl)glycerol, and menthol. One example of a ligand for receptor-mediated endocytosis is folic acid. Folic acid enters the cell by folate-receptor-mediated endocytosis. dsRNA compounds bearing folic acid would be efficiently transported into the cell via the folate-receptor-mediated endocytosis. Li and coworkers report that attachment of folic acid to the 3'-terminus of an oligonucleotide resulted in an 8-fold increase in cellular uptake of the oligonucleotide. Li, S.; Deshmukh, H. M.; Huang, L. *Pharm. Res.* 1998, 15, 1540. Other ligands that have been conjugated to oligonucleotides include polyethylene glycols, carbohydrate clusters, cross-linking agents, porphyrin conjugates, and delivery peptides.

In certain instances, conjugation of a cationic ligand to oligonucleotides results in improved resistance to nucleases. Representative examples of cationic ligands are propylammonium and dimethylpropylammonium. Interestingly, antisense oligonucleotides were reported to retain their high binding affinity to mRNA when the cationic ligand was dispersed throughout the oligonucleotide. See M. Manoharan *Antisense & Nucleic Acid Drug Development* 2002, 12, 103 and references therein.

The ligand-conjugated dsRNA of the invention may be synthesized by the use of a dsRNA that bears a pendant reactive functionality, such as that derived from the attachment of a linking molecule onto the dsRNA. This reactive oligonucleotide may be reacted directly with commercially-available ligands, ligands that are synthesized bearing any of a variety of protecting groups, or ligands that have a linking moiety attached thereto. The methods of the invention facilitate the synthesis of ligand-conjugated dsRNA by the use of, in some preferred embodiments, nucleoside monomers that have been appropriately conjugated with ligands and that may further be attached to a solid-support material. Such ligand-nucleoside conjugates, optionally attached to a solid-support material, are prepared according to some preferred embodiments of the methods of the invention via reaction of a selected serum-binding ligand with a linking moiety located on the 5' position of a nucleoside or oligonucleotide. In certain instances, an dsRNA bearing an aralkyl ligand attached to the 3'-terminus of the dsRNA is prepared by first covalently attaching a monomer building block to a controlled-pore-glass support via a long-chain aminoalkyl group. Then, nucleotides are bonded via standard solid-phase synthesis techniques to the monomer building-block bound to the solid support. The monomer building block may be a nucleoside or other organic compound that is compatible with solid-phase synthesis.

The dsRNA used in the conjugates of the invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

Teachings regarding the synthesis of particular modified oligonucleotides may be found in the following U.S. patents: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, and U.S. Pat. No. 5,608,046, both drawn to conjugated 4'-desmethyl nucleoside analogs; U.S. Pat. Nos. 5,602,240, and 5,610,289, drawn to backbone-modified oligonucleotide analogs; U.S. Pat. Nos. 6,262,241, and 5,459,255, drawn to, inter alia, methods of synthesizing 2'-fluoro-oligonucleotides. Other favourable modifications are set out in U.S. Pat. No. 6,670,486, PCT Publication Nos. WO2003082255 and WO2005021749.

In the ligand-conjugated dsRNA and ligand-molecule bearing sequence-specific linked nucleosides of the invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. Oligonucleotide conjugates bearing a variety of molecules such as steroids, vitamins, lipids and reporter molecules, has previously been described (see Manoharan et al., PCT Application WO 93/07883). In a preferred embodiment, the oligonucleotides or linked nucleosides of the invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

The incorporation of a 2'-O-methyl, 2'-O-ethyl, 2'-O-propyl, 2'-0-allyl, 2'-0-aminoalkyl, 2'-O-methoxyethoxy or 2'-deoxy-2'-fluoro group in nucleosides of an oligonucleotide may provide enhanced therapeutic properties to the oligonucleotide, such as enhanced hybridization kinetics. Further, oligonucleotides containing phosphorothioate backbones have enhanced nuclease stability. Thus, functionalized, linked nucleosides of the invention can be augmented to include either or both a phosphorothioate backbone or a 2'-O-methyl, 2'-O-ethyl, 2'-0-propyl, 2'-O-aminoalkyl, 2'-O-allyl, 2'-O-methoxyethoxy or 2'-deoxy-2'-fluoro group. A summary listing of some of the oligonucleotide modifications known in the art is found at, for example, PCT Publication WO 200370918.

In some embodiments, functionalized nucleoside sequences of the invention possessing an amino group at the 5'-terminus are prepared using a DNA synthesizer, and then reacted with an active ester derivative of a selected ligand. Active ester derivatives are well known to those skilled in the art. Representative active esters include N-hydrosuccinimide esters, tetrafluorophenolic esters, pentafluorophenolic esters and pentachlorophenolic esters. The reaction of the amino group and the active ester produces an oligonucleotide in which the selected ligand is attached to the 5'-position through a linking group. The amino group at the 5'-terminus can be prepared utilizing a 5'-Amino-Modifier C6 reagent. In one embodiment, ligand molecules may be conjugated to oligonucleotides at the 5'-position by the use of a ligand-nucleoside phosphoramidite wherein the ligand is linked to the 5'-hydroxy group directly or indirectly via a linker. Such ligand-nucleoside phosphoramidites are typically used at the end of an automated synthesis procedure to provide a ligand-conjugated oligonucleotide bearing the ligand at the 5'-terminus.

Examples of modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included.

Representative United States Patents relating to the preparation of the above phosphorus-atom-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, each of which is herein incorporated by reference.

Examples of modified internucleoside linkages or backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. As noted in Table 1 and Table 2, a dT-dT pair may be added at the 3' end of either (or both) strand(s) of the dsRNA. The added dT-dT pair in these situations are usually not complementary to the target sequence. These dT-dT pairs, which may contain phosphorothioate (sulfur) internucleoside linkages, are added to enhance stability.

Representative United States patents relating to the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In certain instances, the oligonucleotide may be modified by a non-ligand group. A number of non-ligand molecules have been conjugated to oligonucleotides in order to enhance the activity, cellular distribution or cellular uptake of the oligonucleotide, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-S-tritylthiol (Manoharan et al., Ann. N.Y. Acad. Sci., 1992, 660: 306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such oligonucleotide conjugates have been listed above. Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate. The use of a cholesterol conjugate is particularly preferred since such a moiety can increase targeting liver cells which are a primary site of positive stranded RNA virus (such as HCV) infection.

The instant disclosure describes a wide variety of embodiments of dsRNA that are useful to silence PIK4CB expression and thus to prevent positive stranded RNA virus propagation and to treat associated disorders. While the design of the specific therapeutic agent can take a variety of forms, certain functional characteristics will distinguish preferred combinations of dsRNA from other combinations of dsRNA. In particular, features such as good serum stability, high potency, lack of induced immune response, and good drug like behaviour, all measurable by those skilled in the art, will be tested to identify preferred dsRNA of the invention. In some situations, not all of these functional aspects will be present in the preferred dsRNA combination. But those skilled in the art are able to optimize these variables and others to select preferred compounds of the invention.

The inventors are aware of patterns of chemical modifications which tend to provide significantly improved pharmacological, immunological and ulitimately therapeutic benefit. These patterns are observed to improve the siRNA regardless of the target sequence selected. Table 3 sets out patterns of chemical modifications preferred for use with the duplex dsRNA set out in Table 1 or Table 2. These patterns are not mutually exclusive.

TABLE 3

Preferred Chemical Modifications of siRNA

| Chemical Modification | Changes made to sense strand (5'-3') | Changes made to antisense stand (5'-3') |
| --- | --- | --- |
| Series | | |
| 1 | -dTsdT 3' | -dTsdT 3' |
| 2 | dTsdT 3',2'OMe@all Py | dTsdT 3',2'OMe@uA, cA |
| 3 | dTsdT 3',2'OMe@all Py | dTsdT 3',2'OMe@ uA, cA, uG, uU |
| 4 | Chol ("exo") | dTsdT 3' |
| 5 | Chol ("endo") | dTsdT 3',2'OMe@uA, cA |
| 6 | Chol ("endo") | dTsdT 3',2'OMe@ uA, cA, uG, uU | s = phosphorothioate linkage
dT = deoxyribothymidine
2'OMe = 2'-O—Methyl modification of RNA
Py = pyrimidine nucleotide
Chol = cholesterol. "exo" refers to 3' end linkage; "endo" means linkage is to an internal nucleoside.
uA or cA = indicates at a UA or CA RNA sequence, the U or C receives the indicated modification. Same applies to uG and uU.

Vector Encoded RNAi Agents

The dsRNA of the invention can also be expressed from recombinant viral vectors intracellularly in vivo. The recombinant viral vectors of the invention comprise sequences encoding the dsRNA of the invention and any suitable promoter for expressing the dsRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the dsRNA in a particular tissue or in a particular intracellular environment. The use of recombinant viral vectors to deliver dsRNA of the invention to cells in vivo is discussed in more detail below.

dsRNA of the invention can be expressed from a recombinant viral vector either as two separate, complementary RNA molecules, or as a single RNA molecule with two complementary regions.

Any viral vector capable of accepting the coding sequences for the dsRNA molecule(s) to be expressed can be used, for example vectors derived from adenovirus (AV); adeno-associated virus (AAV); retroviruses (e.g, lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J E et al. (2002), J Virol 76:791-801, the entire disclosure of which is herein incorporated by reference.

Selection of recombinant viral vectors suitable for use in the invention, methods for inserting nucleic acid sequences for expressing the dsRNA into the vector, and methods of delivering the viral vector to the cells of interest are within the skill in the art. See, for example, Dornburg R (1995), Gene Therap. 2: 301-310; Eglitis M A (1988), Biotechniques 6: 608-614; Miller A D (1990), Hum Gene Therap. 1: 5-14; Anderson W F (1998), Nature 392: 25-30; and Rubinson D A et al., Nat. Genet. 33: 401-406, the entire disclosures of which are herein incorporated by reference.

Preferred viral vectors are those derived from AV and AAV. In a particularly preferred embodiment, the dsRNA of the invention is expressed as two separate, complementary single-stranded RNA molecules from a recombinant AAV vector comprising, for example, either the U6 or H1 RNA promoters, or the cytomegalovirus (CMV) promoter.

A suitable AV vector for expressing the dsRNA of the invention, a method for constructing the recombinant AV vector, and a method for delivering the vector into target cells, are described in Xia H et al. (2002), Nat. Biotech. 20: 1006-1010.

Suitable AAV vectors for expressing the dsRNA of the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

Pharmaceutical Compositions Comprising dsRNA

In one embodiment, the invention provides pharmaceutical compositions comprising the dsRNA described herein and a pharmaceutically acceptable carrier. In another embodiment, the invention comprises a combination of the dsRNA and another active principle ingredient. The pharmaceutical composition comprising the combination of dsRNA and active principle ingredient is useful for treating a disease or disorder associated with the pathological processes mediated by positive stranded RNA virus infection.

The pharmaceutical compositions of the invention are administered in dosages sufficient to inhibit expression or activity of the PIK4CB or PIK4CA gene. The present inventors have determined that compositions comprising the dsRNA of the invention can be administered at surprisingly low dosages. A dosage of 5 mg dsRNA per kilogram body weight of recipient per day is sufficient to inhibit or suppress of the PIK4CB or PIK4CA gene.

In general, a suitable dose of each dsRNA in the combination will be in the range of 0.01 to 5.0 milligrams per kilogram body weight of the recipient per day, generally in the range of 1 microgram to 1 mg per kilogram body weight per day. The pharmaceutical composition may be administered once daily, or the dsRNA may be administered as two, three, or more sub-doses at appropriate intervals throughout the day or even using continuous infusion or delivery through a controlled release formulation. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

The inventors recognize that for a variety of reasons, it may be desireable to treat positive stranded RNA virus infection with a combination of two or more dsRNA. One dsRNA is selected from among the dsRNA of the invention, and another dsRNA is selected from among those dsRNA known to target the positive stranded RNA virus itself dsRNA targeting HCV or HPV or other positive stranded RNA viruses may be identified from publications in the prior art. A pharmaceutical composition of the invention comprising more than one type of dsRNA would be expected to contain dosages of individual dsRNA as described herein.

Combinations of dsRNA may be provided together in a single dosage form pharmaceutical composition. Alternatively, combination dsRNA may be provided in separate dosage forms, in which case they may be administered at the same time or at different times, and possibly by different means. The invention therefore contemplates pharmaceutical compositions comprising the desired combinations of dsRNA of the invention; and it also contemplates pharmaceutical compositions of single dsRNA which are intended to be provided as part of a combination regimen. In this latter case, the combination therapy invention is thereby a method of administering rather than a composition of matter.

Advances in mouse genetics have generated a number of mouse models for the study of various human diseases, such as pathological processes mediated by HCV infection. Such models are used for in vivo testing of dsRNA, as well as for determining a therapeutically effective dose, and preferred combinations of dsRNA.

Any method can be used to administer a dsRNA of the present invention to a mammal containing cells infected with HCV. For example, administration can be topical (e.g., vaginal, transdermal, etc); oral; or parenteral (e.g., by subcutaneous, intraventricular, intramuscular, or intraperitoneal injection, or by intravenous drip). Administration can be rapid (e.g., by injection), or can occur over a period of time (e.g., by slow infusion or administration of slow release formulations).

For topical administration, dsRNA can be formulated into compositions such as sterile and non-sterile aqueous solutions, non-aqueous solutions in common solvents such as alcohols, or solutions in liquid or solid oil bases. Such solutions also can contain buffers, diluents, and other suitable additives. Compositions for topical administration can be formulated in the form of transdermal patches, ointments, lotions, creams, gels, drops, suppositories, sprays, liquids, and powders. Gels and creams may be formulated using polymers and permeabilizers known in the art.

For parenteral, intrathecal, or intraventricular administration, a dsRNA molecule can be formulated into compositions such as sterile aqueous solutions, which also can contain buffers, diluents, and other suitable additives (e.g., penetration enhancers, carrier compounds, and other pharmaceutically acceptable carriers).

In addition, dsRNA molecules of the invention can be administered to a mammal containing positive stranded RNA virus infected cells using non-viral methods, such as biologic or abiologic means as described in, for example, U.S. Pat. No. 6,271,359. Abiologic delivery can be accomplished by a variety of methods including, without limitation, (1) loading liposomes with a dsRNA acid molecule provided herein; (2) complexing a dsRNA molecule with lipids or liposomes to form nucleic acid-lipid or nucleic acid-liposome complexes; or (3) providing a polymer, nanoparticle or nanoemulsion based therapeutic delivery system. These techniques are generally well known in the art in other contexts. A brief description follows.

The liposome or lipid complex can be composed of cationic and neutral lipids commonly used to transfect cells in vitro. Cationic lipids can complex (e.g., charge-associate) with negatively charged nucleic acids to form liposomes. Examples of cationic liposomes include, without limitation, lipofectin, lipofectamine, lipofectace, and DOTAP. Procedures for forming liposomes are well known in the art. Liposome compositions can be formed, for example, from phosphatidylcholine, dimyristoyl phosphatidylcholine, dipalmitoyl phosphatidylcholine, dimyristoyl phosphatidylglycerol, or dioleoyl phosphatidylethanolamine. Numerous lipophilic agents are commercially available, including Lipofectin® (Invitrogen/Life Technologies, Carlsbad, Calif.) and Effectene™ (Qiagen, Valencia, Calif.). In addition, systemic delivery methods can be optimized using commercially available cationic lipids such as DDAB or DOTAP, each of which can be mixed with a neutral lipid such as DOPE or cholesterol. In some cases, liposomes such as those described by Templeton et al. (Nature Biotechnology, 15: 647-652 (1997)) can be used. In some embodiments, the dosage will be fully encapsulated in the liposome, such as in the SNALP described in Morrissey et al. Nat Biotechnol. 2005 August; 23(8):1002-7. Epub 2005 Jul. 24. See also Wheeler, J. J. et al. 1999. Gene Ther. 6, 271-281. In other embodiments, polycations such as polyethyleneimine can be used to achieve delivery in vivo and ex vivo (Boletta et al., J. Am Soc. Nephrol. 7: 1728 (1996)). Additional information regarding the use of liposomes to deliver nucleic acids can be found in U.S. Pat. No. 6,271,359, PCT Publication WO 96/40964 and Morrissey, D. et al. 2005. Nat Biotechnol. 23(8):1002-7.

Biologic delivery can be accomplished by a variety of methods including, without limitation, the use of viral vectors. For example, viral vectors (e.g., adenovirus and herpesvirus vectors) can be used to deliver dsRNA molecules to skin cells and cervical cells. Standard molecular biology techniques can be used to introduce one or more of the dsRNAs provided herein into one of the many different viral vectors previously developed to deliver nucleic acid to cells. These resulting viral vectors can be used to deliver the one or more dsRNAs to cells by, for example, infection.

dsRNAs of the present invention can be formulated in a pharmaceutically acceptable carrier or diluent. A "pharmaceutically acceptable carrier" (also referred to herein as an "excipient") is a pharmaceutically acceptable solvent, suspending agent, or any other pharmacologically inert vehicle. Pharmaceutically acceptable carriers can be liquid or solid, and can be selected with the planned manner of administration in mind so as to provide for the desired bulk, consistency, and other pertinent transport and chemical properties. Typical pharmaceutically acceptable carriers include, by way of example and not limitation: water; saline solution; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

In addition, dsRNA that target the PIK4CB gene expression can be formulated into compositions containing the dsRNA admixed, encapsulated, conjugated, or otherwise associated with molecules (including small molecule therapeutic agents), molecular structures, or mixtures of nucleic acids. For example, a composition containing one or more dsRNA agents of the invention can contain other therapeutic agents such as anti-inflammatory drugs (e.g., nonsteroidal anti-inflammatory drugs and corticosteroids) and antiviral drugs (e.g., ribivirin, vidarabine, acyclovir, and ganciclovir).

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the invention lies generally within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the dsRNAs of the invention can be administered in combination with other known agents effective in treatment of pathological processes mediated by HCV infection. In any event, the administering physician can adjust the amount and timing of dsRNA administration on the basis of results observed using standard measures of efficacy known in the art or described herein.

Combinations of dsRNA can be tested in vitro and in vivo using the same methods employed for identification of preferred single dsRNA. Such combinations may be selected based on a purely bioinformatics basis. Alternatively, such combinations may be selected based on in vitro or in vivo evaluations along the lines of those described herein for single dsRNA agents. A preferred assay for testing combinations of dsRNA is the assay set out in the Examples below.

Methods for Treating Diseases Caused by Positive Stranded RNA Virus Infection

The methods and compositions described herein can be used to treat diseases and conditions caused by positive stranded RNA virus infection (such as HCV), which can be the result of clinical or sub-clinical infections.

In overview, the method of treating infection by a positive stranded RNA viruses comprises administering to a patient in need thereof, a compound which selectively inhibits the activity of the phosphatidylinositol 4-kinase (PI4K). Such compounds can be selected from among small molecules, dsRNA, a DNA antisense DNA, a ribozyme, or a DNA vector encoding the foregoing. Small molecule agents which are selective for PIK4CB and/or PIK4CA in the liver would be of considerable interest for therapeutic purposes in the treatment of infection by positive stranded RNA viruses.

Such diseases and conditions, herein sometimes called "pathological processes mediated by positive stranded RNA virus infection". The major hepatological consequence of HCV infection is cirrhosis and complications thereof including haemorrhage, hepatic insufficiency, and hepatocellular carcinoma. Fibrosis is the result of chronic inflammation causing the deposition of extracellular matrix component distorting the hepatic architecture and blocking microcirculation and liver function. As cirrhosis progresses and the fibrotic tissue builds up, severe necroinflamatory activity ensues and steatosis begins. Steatosis leads to extrahepatic pathologies including diabetes, protein malnutrition, hypertension, cell toxins, obesity, and anoxia. As fibrosis and steatosis becomes severe the liver will eventually fail and require liver transplantation.

In this specification, a "method of treating" or "method of treatment" is intended to refer to methods which treat, prevent, are prophylactic against, or reduce the significance of (at an objective or subjective level) one or more symptom of, the disease, disorder or condition which is indicated by the phrase.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1: dsRNA Synthesis

Source of Reagents

Where the source of a reagent is not specifically given herein, such reagent may be obtained from any supplier of reagents for molecular biology at a quality/purity standard for application in molecular biology.

siRNA Synthesis

Single-stranded RNAs were produced by solid phase synthesis on a scale of 1 μmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution was stored at −20° C. until use.

For the synthesis of 3'-cholesterol-conjugated siRNAs (herein referred to as -Chol-3'), an appropriately modified solid support was used for RNA synthesis. The modified solid support was prepared as follows:

Diethyl-2-azabutane-1,4-dicarboxylate AA

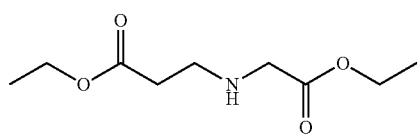

A 4.7 M aqueous solution of sodium hydroxide (50 mL) was added into a stirred, ice-cooled solution of ethyl glycinate hydrochloride (32.19 g, 0.23 mole) in water (50 mL). Then, ethyl acrylate (23.1 g, 0.23 mole) was added and the mixture was stirred at room temperature until completion of the reaction was ascertained by TLC. After 19 h the solution was partitioned with dichloromethane (3×100 mL). The organic layer was dried with anhydrous sodium sulfate, filtered and evaporated. The residue was distilled to afford AA (28.8 g, 61%).

3-{Ethoxycarbonylmethyl-[6-(9H-fluoren-9-yl-methoxycarbonyl-amino)-hexanoyl]-amino}-propionic acid ethyl ester AB

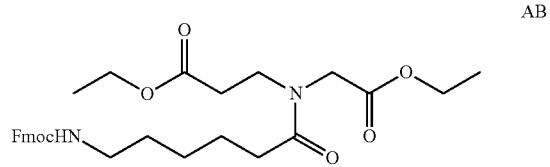

Fmoc-6-amino-hexanoic acid (9.12 g, 25.83 mmol) was dissolved in dichloromethane (50 mL) and cooled with ice. Diisopropylcarbodiimde (3.25 g, 3.99 mL, 25.83 mmol) was added to the solution at 0° C. It was then followed by the addition of Diethyl-azabutane-1,4-dicarboxylate (5 g, 24.6 mmol) and dimethylamino pyridine (0.305 g, 2.5 mmol). The solution was brought to room temperature and stirred further for 6 h. Completion of the reaction was ascertained by TLC. The reaction mixture was concentrated under vacuum and ethyl acetate was added to precipitate diisopropyl urea. The suspension was filtered. The filtrate was washed with 5% aqueous hydrochloric acid, 5% sodium bicarbonate and water. The combined organic layer was dried over sodium sulfate and concentrated to give the crude product which was purified by column chromatography (50% EtOAC/Hexanes) to yield 11.87 g (88%) of AB.

3-[(6-Amino-hexanoyl)-ethoxycarbonylmethyl-amino]-propionic acid ethyl ester AC

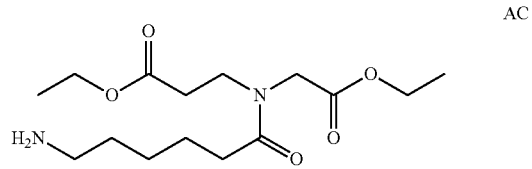 [SMILES: CCOC(=O)CCN(CC(=O)OCC)C(=O)CCCCCN]

3-{Ethoxycarbonylmethyl-[6-(9H-fluoren-9-ylmethoxy-carbonylamino)-hexanoyl]-amino}-propionic acid ethyl ester AB (11.5 g, 21.3 mmol) was dissolved in 20% piperidine in dimethylformamide at 0° C. The solution was continued stirring for 1 h. The reaction mixture was concentrated under vacuum, water was added to the residue, and the product was extracted with ethyl acetate. The crude product was purified by conversion into its hydrochloride salt.

3-({6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}ethoxy-carbonylmethyl-amino)-propionic acid ethyl ester AD

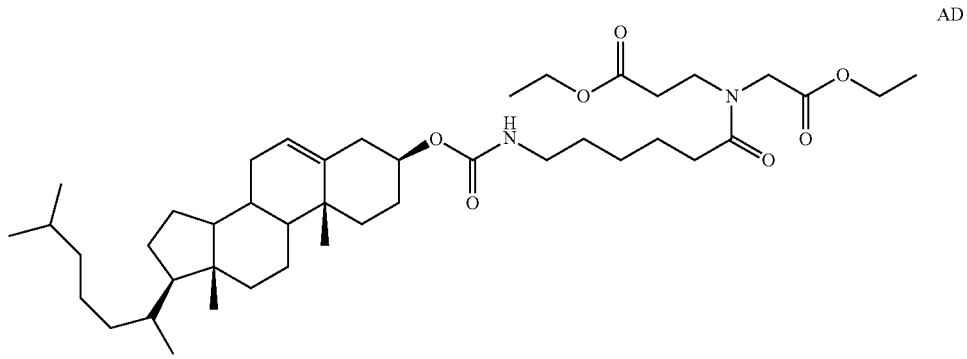 [SMILES: CCOC(=O)CCN(CC(=O)OCC)C(=O)CCCCCNC(=O)O[C@H]1CC[C@@]2(C)C(=CCC3C2CC[C@@]2(C)C3CC[C@@H]2C(C)CCCC(C)C)C1]

The hydrochloride salt of 3-[(6-Amino-hexanoyl)-ethoxycarbonylmethyl-amino]-propionic acid ethyl ester AC (4.7 g, 14.8 mmol) was taken up in dichloromethane. The suspension was cooled to 0° C. on ice. To the suspension diisopropylethylamine (3.87 g, 5.2 mL, 30 mmol) was added. To the resulting solution cholesteryl chloroformate (6.675 g, 14.8 mmol) was added. The reaction mixture was stirred overnight. The reaction mixture was diluted with dichloromethane and washed with 10% hydrochloric acid. The product was purified by flash chromatography (10.3 g, 92%).

1-{6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}-4-oxo-pyrrolidine-3-carboxylic acid ethyl ester AE

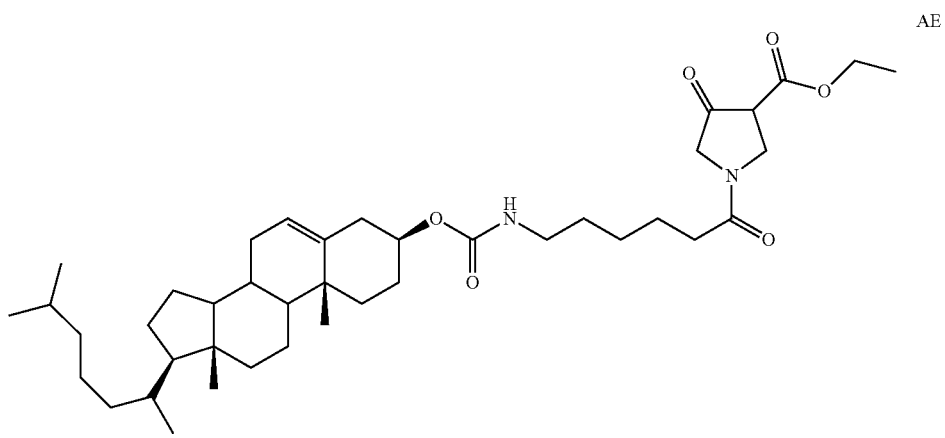 [SMILES: CCOC(=O)C1CN(C(=O)CCCCCNC(=O)O[C@H]2CC[C@@]3(C)C(=CCC4C3CC[C@@]3(C)C4CC[C@@H]3C(C)CCCC(C)C)C2)CC1=O]

Potassium t-butoxide (1.1 g, 9.8 mmol) was slurried in 30 mL of dry toluene. The mixture was cooled to 0° C. on ice and 5 g (6.6 mmol) of diester AD was added slowly with stirring within 20 mins. The temperature was kept below 5° C. during the addition. The stirring was continued for 30 mins at 0° C. and 1 mL of glacial acetic acid was added, immediately followed by 4 g of $NaH_2PO_4 \cdot H_2O$ in 40 mL of water The resultant mixture was extracted twice with 100 mL of dichloromethane each and the combined organic extracts were washed twice with 10 mL of phosphate buffer each, dried, and evaporated to dryness. The residue was dissolved in 60 mL of toluene, cooled to 0° C. and extracted with three 50 mL portions of cold pH 9.5 carbonate buffer. The aqueous extracts were adjusted to pH 3 with phosphoric acid, and extracted with five 40 mL portions of chloroform which were combined, dried and evaporated to dryness. The residue was purified by column chromatography using 25% ethylacetate/hexane to afford 1.9 g of b-ketoester (39%).

[6-(3-Hydroxy-4-hydroxymethyl-pyrrolidin-1-yl)-6-oxo-hexyl]-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AF

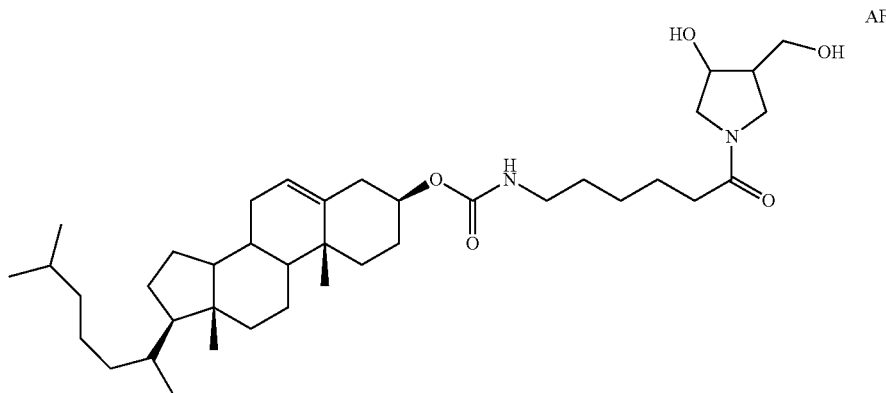 [SMILES: CC(C)CCCC(C)[C@H]1CCC2C3CC=C4C[C@@H](OC(=O)NCCCCCC(=O)N5CC(O)C(CO)C5)CC[C@]4(C)C3CC[C@@]21C]

Methanol (2 mL) was added dropwise over a period of 1 h to a refluxing mixture of b-ketoester AE (1.5 g, 2.2 mmol) and sodium borohydride (0.226 g, 6 mmol) in tetrahydrofuran (10 mL). Stirring was continued at reflux temperature for 1 h. After cooling to room temperature, 1 N HCl (12.5 mL) was added, the mixture was extracted with ethylacetate (3×40 mL). The combined ethylacetate layer was dried over anhydrous sodium sulfate and concentrated under vacuum to yield the product which was purified by column chromatography (10% MeOH/CHCl₃) (89%).

(6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14, 15,16,17-tetradecahydro-1H-cyclopenta[a]phenanthren-3-yl ester AG Diol AF (1.25 gm 1.994 mmol) was dried by evaporating with pyridine (2×5 mL) in vacuo. Anhydrous pyridine (10 mL) and 4,4'-dimethoxytritylchloride (0.724 g, 2.13 mmol) were added with stirring. The reaction was carried out at room temperature overnight. The reaction was quenched by the addition of methanol. The reaction mixture was concentrated under vacuum and to the residue dichloromethane (50 mL) was added. The organic layer was washed with 1M aqueous sodium bicarbonate. The organic layer was dried over anhydrous sodium sulfate, filtered and concentrated. The residual pyridine was removed by evaporating with toluene. The crude product was purified by column chromatography (2% MeOH/Chloroform, Rf=0.5 in 5% MeOH/CHC13) (1.75 g, 95%).

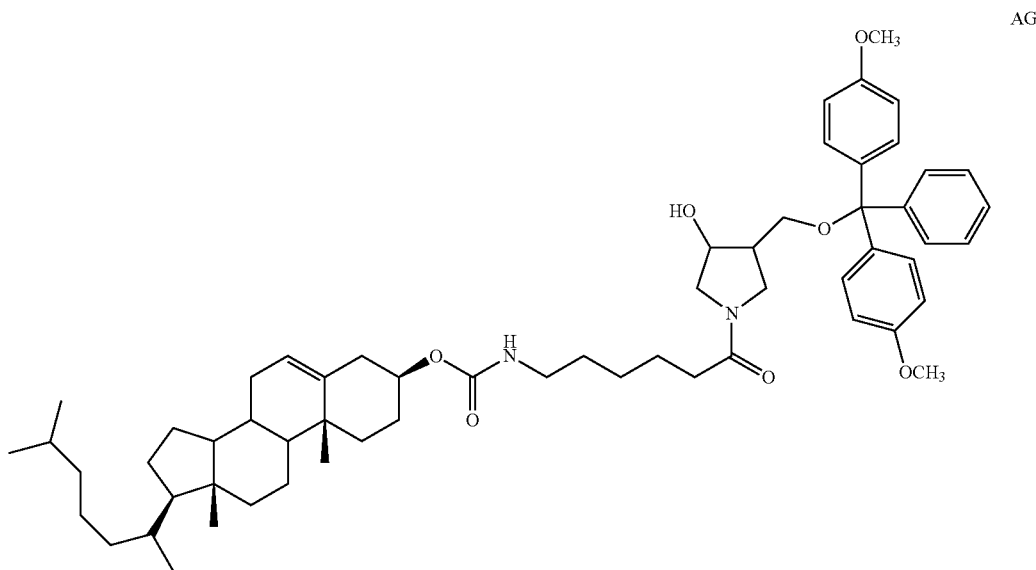 [SMILES: COc1ccc(C(OCC2CN(C(=O)CCCCCNC(=O)O[C@H]3CC[C@@]4(C)C(=CCC5C4CC[C@@]4(C)C5CC[C@@H]4C(C)CCCC(C)C)C3)CC2O)(c2ccccc2)c2ccc(OC)cc2)cc1]

Succinic acid mono-(4-[bis-(4-methoxy-phenyl)-phenyl-methoxymethyl]-1-{6-[17-(1,5-dimethyl-hexyl)-10,13-dimethyl 2,3,4,7,8,9,10,11,12,13,14,15,16,17-tetradecahydro-1H cyclopenta[a]phenanthren-3-yloxycarbonylamino]-hexanoyl}-pyrrolidin-3-yl) ester AH

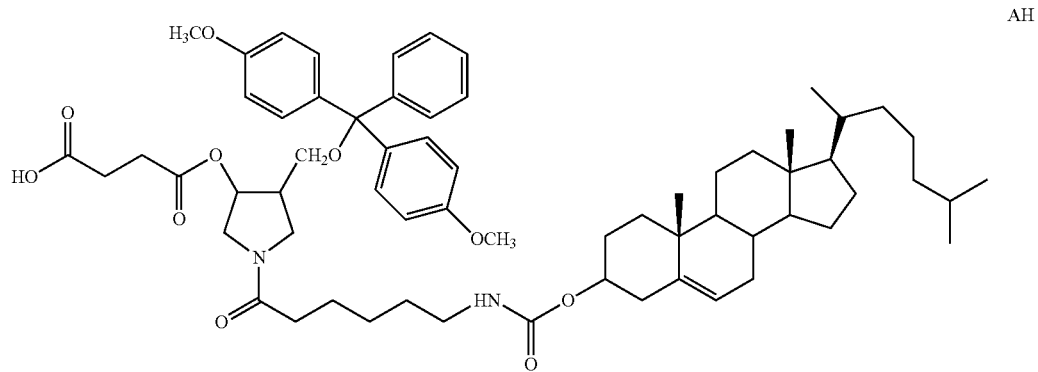

AH

Compound AG (1.0 g, 1.05 mmol) was mixed with succinic anhydride (0.150 g, 1.5 mmol) and DMAP (0.073 g, 0.6 mmol) and dried in a vacuum at 40° C. overnight. The mixture was dissolved in anhydrous dichloroethane (3 mL), triethylamine (0.318 g, 0.440 mL, 3.15 mmol) was added and the solution was stirred at room temperature under argon atmosphere for 16 h. It was then diluted with dichloromethane (40 mL) and washed with ice cold aqueous citric acid (5 wt %, 30 mL) and water (2×20 mL). The organic phase was dried over anhydrous sodium sulfate and concentrated to dryness. The residue was used as such for the next step.

Cholesterol Derivatised CPG AI

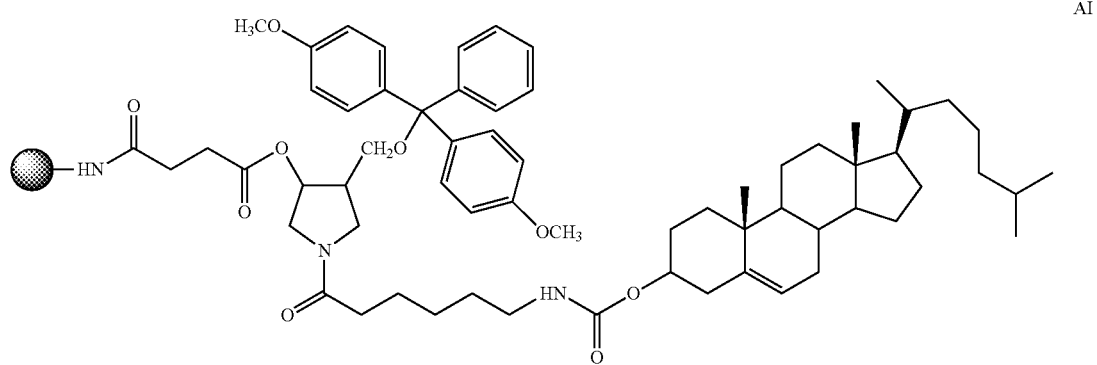

AI

Succinate AH (0.254 g, 0.242 mmol) was dissolved in a mixture of dichloromethane/acetonitrile (3:2, 3 mL). To that solution DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) were added successively. To the resulting solution triphenylphosphine (0.064 g, 0.242 mmol) in acetonitrile (0.6 ml) was added. The reaction mixture turned bright orange in color. The solution was agitated briefly using a wrist-action shaker (5 mins). Long chain alkyl amine-CPG (LCAA-CPG) (1.5 g, 61 mM) was added. The suspension was agitated for 2 h. The CPG was filtered through a sintered funnel and washed with acetonitrile, dichloromethane and ether successively. Unreacted amino groups were masked using acetic anhydride/pyridine. The achieved loading of the CPG was measured by taking UV measurement (37 mM/g).

The synthesis of siRNAs bearing a 5'-12-dodecanoic acid bisdecylamide group (herein referred to as "5'-C32-") or a 5'-cholesteryl derivative group (herein referred to as "5'-Chol-") was performed as described in WO 2004/065601, except that, for the cholesteryl derivative, the oxidation step was performed using the Beaucage reagent in order to introduce a phosphorothioate linkage at the 5'-end of the nucleic acid oligomer.

Example 2: dsRNA Expression Vectors

In another aspect of the invention, dsRNA molecules that modulate PIK4CB expression activity or PIK4CA expression activity are expressed from transcription units inserted into DNA or RNA vectors (see, e.g., Couture, A, et al., TIG. (1996), 12:5-10; Skillern, A., et al., International PCT Publication No. WO 00/22113, Conrad, International PCT Publication No. WO 00/22114, and Conrad, U.S. Pat. No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann, et al., *Proc. Natl. Acad. Sci. USA* (1995) 92:1292).

The individual strands of a dsRNA can be transcribed by promoters on two separate expression vectors and co-transfected into a target cell. Alternatively each individual strand of the dsRNA can be transcribed by promoters both of which are located on the same expression plasmid. In a preferred embodiment, a dsRNA is expressed as an inverted repeat joined by a linker polynucleotide sequence such that the dsRNA has a stem and loop structure.

The recombinant dsRNA expression vectors are generally DNA plasmids or viral vectors. dsRNA expressing viral vectors can be constructed based on, but not limited to, adeno-associated virus (for a review, see Muzyczka, et al., *Curr. Topics Micro. Immunol.* (1992) 158:97-129)); adenovirus (see, for example, Berkner, et al., *BioTechniques* (1998) 6:616), Rosenfeld et al. (1991, Science 252:431-434), and Rosenfeld et al. (1992), *Cell* 68:143-155)); or alphavirus as well as others known in the art. Retroviruses have been used to introduce a variety of genes into many different cell types, including epithelial cells, in vitro and/or in vivo (see, e.g., Eglitis, et al., *Science* (1985) 230:1395-1398; Danos and Mulligan, *Proc. Natl. Acad. Sci. USA* (1998) 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Nad. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

The promoter driving dsRNA expression in either a DNA plasmid or viral vector of the invention may be a eukaryotic RNA polymerase I (e.g. ribosomal RNA promoter), RNA polymerase II (e.g. CMV early promoter or actin promoter or U1 snRNA promoter) or generally RNA polymerase III promoter (e.g. U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g. the insulin regulatory sequence for pancreas (Bucchini et al., 1986, Proc. Natl. Acad. Sci. USA 83:2511-2515)).

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D1-thiogalactopyranoside (EPTG). A person skilled in the art would be able to choose the appropriate regulatory/promoter sequence based on the intended use of the dsRNA transgene.

Generally, recombinant vectors capable of expressing dsRNA molecules are delivered as described herein, and persist in target cells. Alternatively, viral vectors can be used that provide for transient expression of dsRNA molecules. Such vectors can be repeatedly administered as necessary. Once expressed, the dsRNAs bind to target RNA and modulate its function or expression. Delivery of dsRNA expressing vectors can be systemic, such as by intravenous or intramuscular administration, by administration to target cells ex-planted from the patient followed by reintroduction into the patient, or by any other means that allows for introduction into a desired target cell.

dsRNA expression DNA plasmids are typically transfected into target cells as a complex with cationic lipid carriers (e.g. Oligofectamine) or non-cationic lipid-based carriers (e.g. Transit-TKO™). Multiple lipid transfections for dsRNA-mediated knockdowns targeting different regions of the PIK4CB gene over a period of a week or more are also contemplated by the invention. Successful introduction of the vectors of the invention into host cells can be monitored using various known methods. For example, transient transfection. can be signaled with a reporter, such as a fluorescent marker, such as Green Fluorescent Protein (GFP). Stable transfection. of ex vivo cells can be ensured using markers that provide the transfected cell with resistance to specific environmental factors (e.g., antibiotics and drugs), such as hygromycin B resistance.

The PIK4CB and PIK4CA specific dsRNA molecules can also be inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Example 3: Identification of PIK4CB and PIK4CA as Essential Host Targets for HCV Infection A large scale transfection based siRNA delivery system was used to identify the PI4KCB and PI4KCA targets. This system was described previously (Borawski J, Lindeman A, Buxton F, Labow M, Gaither L A. Optimization procedure for small interfering RNA transfection in a 384-well format. J Biomol Screen. 2007 June; 12(4):546-59. Epub 2007 Apr. 13), incorporated herein by reference.

In the instant case, the system employed an HCV subgenomic replicon system designed to identify host proteins essential for HCV replication. A Huh7 subgenomic replicon cell line (as described by Lohmann, V., et. al. (1999) Science. 285:110) was screened using a kinome (i.e. the known kinases of the human genome (Dharmacon (Boulder Col.)) siRNA library. The HCV subgenomic replicon system allows for HCV replication to be studied in vitro and in vivo using human hepatoma cells (Huh7) stably transformed with the modified HCV genome lacking the structural proteins. The HCV subgenomic replicon contains the non-structural proteins in cis with a luciferase reporter under a neomycin selection marker. This construct was designed for stable in vitro measurement of the HCV replicon RNA levels and replicon activity. The goal of this study was to use siRNA screening technology as a tool to identify novel host proteins that inhibit the subgenomic HCV replicon in Huh7 cells.

To this end, a set of 779 siRNA smart pools targeting the kinome was screened and novel regulators of the HCV replicon were discovered and verfied. (Smart pool referres to mixing 4 individual siRNAs in equalmolar concentrations before adding the mixture to cells.) siRNAs to PIK4CB (phosphatidylinositol 4-kinase, catalytic, beta polypeptide) or PIK4CA ((phosphatidylinositol 4-kinase, catalytic, alpha polypeptide), were identified that inhibited accumulation of luciferase from the viral replicon with high potency. These data establish that this cellular protein can be used as a drug target for the inhibition of HCV replication.

Construction of the Huh7 subgenomic replicon cell line (also called herein Clone A cells) is based on the HCV genome. The full length HCV genome is illustrated in FIG. 1A. The 9.6 kb genome is a positive single stranded RNA virus with four structural and six non-structural proteins. A salient feature of the replicon is the 5' and 3' UTRs which are required for efficient replicon activity. This virus can replicate in vitro but creates infectious virus, requiring special training and facilities (Thomson B J, Finch R G Hepatitis C virus infection. Clin Microbiol Infect. 2005 February; 11(2): 86-94.). Therefore the infectious virus was altered to create a minimal viral genome capable of replication in vitro without the liability of creating infectious particles. The construct is shown in FIG. 1B, the HCV subgenomic replicon which used to create the Clone A cells (Lohmann V, Korner F, Koch J, Herian U, Theilmann L, Bartenschlager R. Replication of subgenomic hepatitis C virus RNAs in a hepatoma cell line. Science. 1999 Jul. 2; 285(5424):110-3). This virus was highly optimized to capture HCV replicon activity in vitro, in human liver cells. It cannot create infectious viral particles but can self-replicate in the cytoplasm, making it amenable for cell culture studies as well as high throughput screening. The structural proteins have been replaced with a neomycin resistance gene and a firefly luciferase reporter to measure replicon activity. The Clone Ar construct is made up of the same back-bone as the subgenomic virus but the structural proteins have been removed (FIG. 1C). This cell line was used to test if siRNAs could non-specifically inhibit luciferase activity or expression.

siRNA smart pools directed to 779 phylogenetically related kinases were transfected into the Clone A (HCV subgenomic replicon) cells. A siRNA duplex directed against pGL2 luciferase was used as a positive control to inhibit luciferase activity. Cells were transfected for 72 hours and luciferase activity was measured using the Bright-Glo luciferase assay (Borawski J, Lindeman A, Buxton F, Labow M, Gaither L A. Optimization procedure for small interfering RNA transfection in a 384-well format. J Biomol Screen. 2007 June; 12(4):546-59. Epub 2007 Apr. 13).

Several siRNAs were found to be potent inhibitors of luciferase activity, including those pools targeting PIK4CB (NM_002651) and PIK4CA (NM_002650).

Example 4: Confirmation and Measurement of PIK4CB and PIK4CA siRNA Activity

Confirmation of siRNA hits from a screen was achieved with a series of steps including analysis of multiple independent gene specific siRNAs as well as correlating phenotypically active siRNAs with efficiency of mRNA knock down. To first confirm the specificity of the siRNA hits, multiple sequence independent siRNAs were tested both for the ability to inhibit luciferase activity and inability to affect cell viability. The siRNA hits were also tested in the Clone Ar (similar to Clone A but lacking structural proteins as in FIG. 1c) cells to confirm that the siRNAs were specifically targeting the replicon proteins and not inhibiting luciferase activity (or expression) in a replicon independent manner.

The next step was phenotype and RTPCR validation. Four independent siRNAs for PIK4CB and four independent siRNAs for PIK4CA were analyzed for their ability to knock down replicon activity, effects on cell viability, and ability to knock down target gene mRNA levels.

The siRNA employed in this example were as set out in Table 1 and Table 2. FIG. 2 demonstrates results of dsRNA targeting PIK4CB and PIK4CA in the Clone A assay. Results of testing dsRNA as individual duplexes PIK4CA1-PIK4CA4 (column 1-4) as a PIK4CA Smart Pool (col. 5), as individual duplexes PIK4CB1-PIK4CB4 (col. 6-9) or as a PIK4CB Smart Pool (Col. 10). Cells were transfected for 72 hours and luciferase activity was measured using the Bright-Glo luciferase assay (Borawski J, Lindeman A, Buxton F, Labow M, Gaither L A. Optimization procedure for small interfering RNA transfection in a 384-well format. J Biomol Screen. 2007 June; 12(4):546-59. Epub 2007 Apr. 13). Results are measured relative to GAPDH (control; column 11), Assay performed using 25 nM of dsRNA per well using Clone A cells; Bright-Glo activity measured at 72 hours post transfection. dsRNA targeting GAPDH (column 11) was used as the negative control and dsRNA targeting pGL2 (column 12) was the positive control.

Results in FIG. 2 show that relative to GAPDH, dsRNA directed to PIK4CB or PIK4CA can reduce the expression of the HCV replicon (measured by luciferase expression) in the Clone A cells by at least 20% and up to about 90%. A variety of intermediate acitivites are identified. Additional data confirms that the dsRNA of this assay do not hinder cell viability nor do they demonstrate significant non-specific effects on the cells in the Clone Ar assay (data not shown).

FIGS. 3A and 3B confirm that the PIK4CA targeted dsRNA are specific for PIK4CA and not PIK4CB; FIGS. 3C and 3D confirm that PIK4CB targeted dsRNA are specific for PIK4CB and not PIK4CA.

Figure 3:
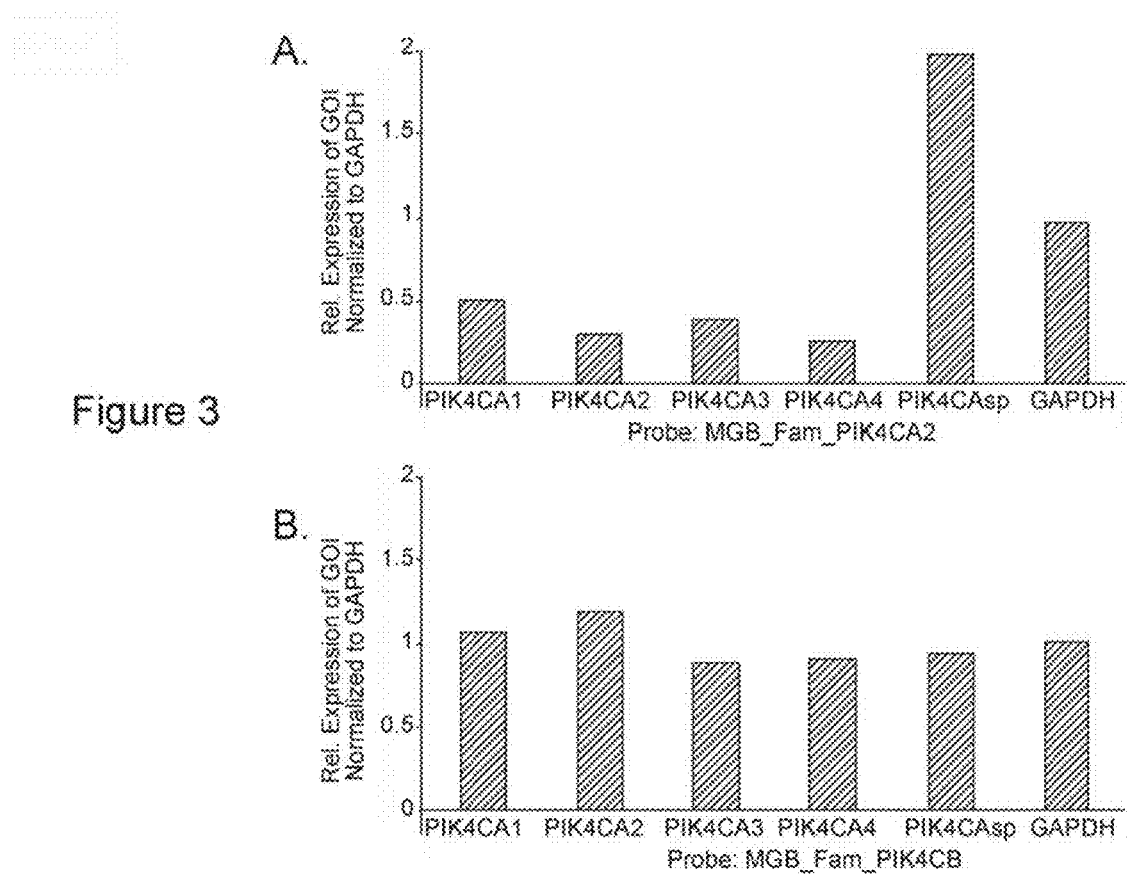
FIG. 3. RTPCR of PIK4CA and PIK4CB. Huh7 replicon cells were transfected with siRNA for 72 hours, mRNA was isolated and RTPCR was analyzed by Taqman. Results were normalized to GAPDH transfected cells. A. Transfection of PIK4CA siRNAs, Taq man RTPCR using PIK4CA primers. B. Transfection of PIK4CA siRNAs, Taq man RTPCR using PIK4CB primers. C. Transfection of PIK4CB siRNAs, Taq man RTPCR using PIK4CB primers. D. Transfection of PIK4CB siRNAs, Taq man RTPCR using PIK4CA primers. GOI=Gene-of-Interest. PIK4CAsp=PIK4CA Smart Pool; PIK4CBsp=PIK4CB Smart Pool.
Figure 3:
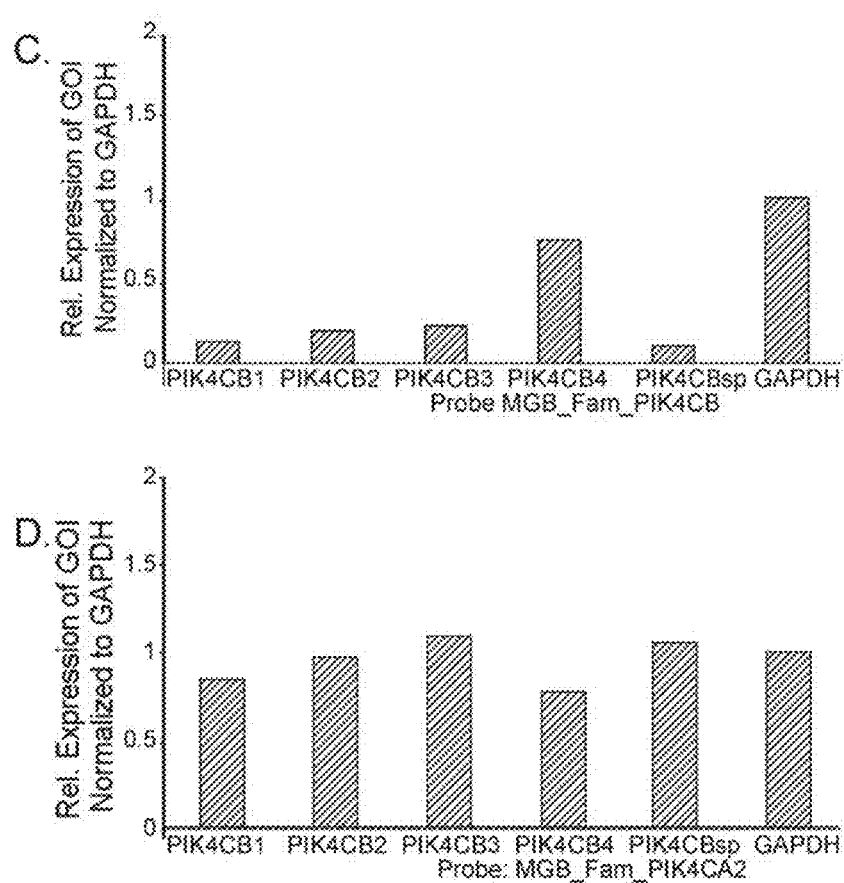

Results for FIG. 3 were generated using Real-Time PCR In this method, two wells transfected with siRNAs were pooled together and mRNA was isolated using the RNeasy96 kit (Qiagen #74182). Preparations were DNAse 1 treated twice for 15 minutes each. cDNA was generated using the High Capacity cDNA Archive kit (Applied Biosystems #4322171), and the RNA was primed using Oligo dT25 (Sigma Genosys). PCR buffer (Roche #1699105) was supplemented with MgCl2 (Ambion #9530 g) as follows; 10× buffer at 10 µl, 1M MgCl2 at 0.55 µl, 50 uM oligo dT25, 100 mM dNTPs at 4 µl, RNasIn, 20 U/µl at 1 µl, Multiscribe 50 U/µl at 5 µl, water at 12.45 µl, and RNA at 66 µl for a total volume of 100 µl. The cDNA was quantified using primers designed in house, PIK4CA (NM_002650)

Fwd:
GCCCTGTCTGAAGTGAAGGT
SEQ ID No.: 417

Reverse:
CTTTTGCAGCACTCTGCATC
SEQ ID No.: 418

At 1662: crossing intron 3006 bp at 1690 At 1774 reversed: crossing intron 3006 bp at 1690;

PIK4CB was measured using primers designed in house against PIK4CB (NM_002651)

Fwd:
ATGGACAAGGTGGTGCAGAT
SEQ ID No.: 419

Reverse:
CCTCAGTCATGCTCATGTGG
SEQ ID No. :420

At 2334 to 2452: crossing intron 981 bp at 2374; (Sigma Genosys) using Syber green on an Applied Biosystems 7900HT (Applied Biosystems #4329001). In FIG. 3, the label "sp" refers to the term SMARTpool. It referres to mixing 4 individual siRNAs in equalmolar concentrations before adding the mixture to cells. In a Smart Pool, 4 individual siRNAs are added at lower relative concentrations (i.e.—a 50 nM equalmolar concentration would be 12.5 nM concentration for each individual siRNA in the SMART pool).

Further confirmation of the targets was achieved using another set of three individual duplexes against PIK4CA (NM_002650, Dharmacon #D-006776) and PIK4CB (NM_002651, Dharmacon #D-006777). siRNA employed as indicated in Table 1 and Table 2.

Each siRNA was resuspended in siRNA buffer (Dharmacon, #B-002000-UB-015) to a stock concentration of 20 µM. 2.5 µL of each stock solution was diluted in 197.5 µL Opti-Mem in a 96 well PCR plate (ABgene, #AB-1000) to make a 250 nM working stamp. 0.20 µL of Dharmafect1 transfection reagent (Dharmacon, #T2001-03) diluted in 10 µL Opti-Mem was added to each well of a 96 well tissue culture plate (Costar, #3917). 10 µL of each siRNA stamp was added to the 96 well plate containing the Dharmafect1 and incubated for 20 minutes to allow complexes to form. After the incubation, 6000 Huh7 HCV subgenomic replicon cells in 80 assay media were added per well. Cells were incubated for 72 hours and assayed for luciferase activity and cell viability (as described previously for FIG. 2).

Figure 4:
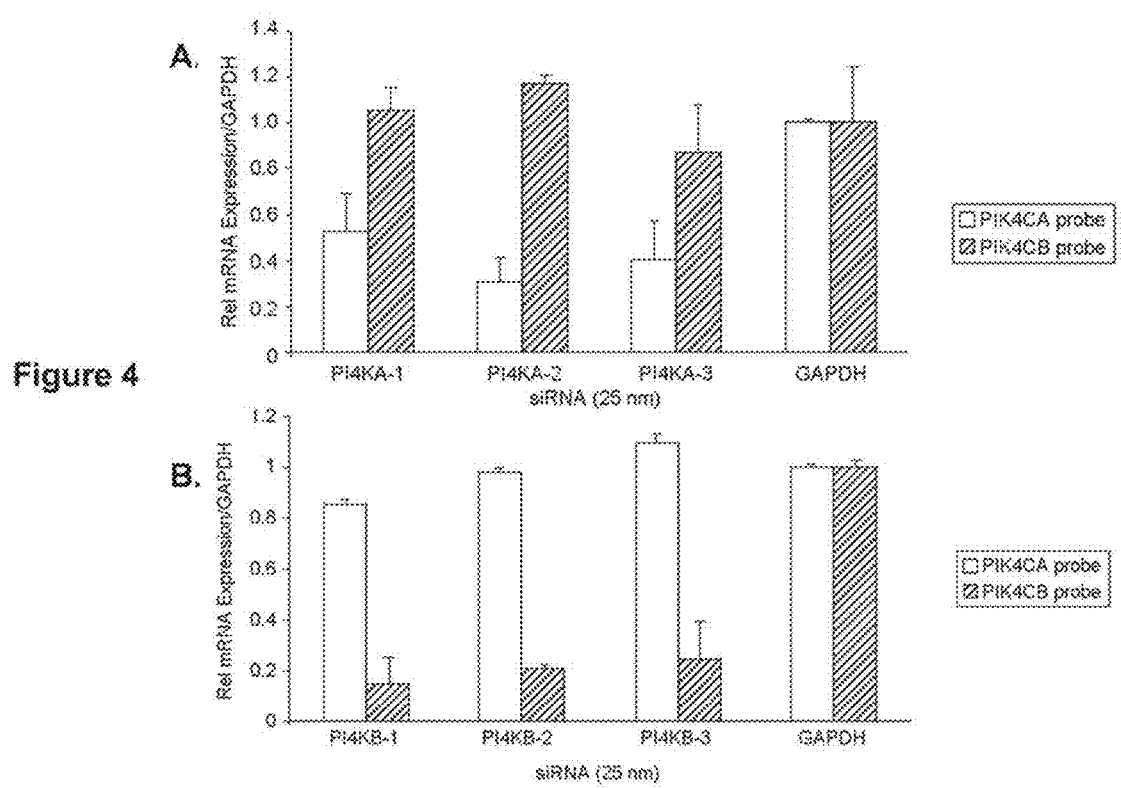
FIG. 4. A) mRNA expression of PIK4CA (light bars) or PIK4CB (dark bars) after treatment by the indicated siRNA targeting PIK4CA (25 nM). B) mRNA expression of PIK4CA (light bars) or PIK4CB (dark bars) after treatment by the indicated siRNA targeting PIK4CB (25 nM).

In FIG. 4 each of the siRNAs was validated using the Taqman Gene Expression Assay (Applied Biosystems) per manufacturer's instructions. siRNAs were transfected in Huh7 HCV subgenomic replicon cells in 96 well format as described above. mRNA was isolated using the RNeasy96 Kit (Qiagen, #74182). mRNA from duplicate wells were pooled together and cDNA was generated using the Sprint Powerscript Preprimed 96 Plate Oligo (dt) (Clontech Laboratories, #639557). The cDNA was quantified using premixed Taqman probes and primers from Applied Biosystems, PIK4CA (NM_002650, Applied Biosystems #Hs01021073_m1) PIK4CB (NM_002651, Applied Biosystems #Hs00356327_m1) in 384 well format. 4.8 cDNA per well was added to a 384 well PCR plate (Applied Biosystems, #4309849). 0.6 µL of the Taqman probe for the gene of interest (GOI), 0.6 µL β-Actin control probe (Applied Biosystems, #4310881E) and 6 µL 2×PCR Master Mix (Applied Biosystems, #4304437) was added to the cDNA per well. The reaction was run on an Applied Biosystems 7900HT Real Time PCR system (Applied Biosystems, #4329001).

In FIG. 4A cells were transfected with PI4KA siRNAs and mRNA was measured using both PI4KA and PI4KB RTPCR Taq man probes. In FIG. 4B cells were transfected with PI4KB siRNAs and mRNA was measured using both PI4KA and PI4KB RTPCR Taq man probes. As demonstrated by the figure the siRNAs specifically knock-down their designated targets and do not cross react and inhibit the other PI4K mRNA transcript or the control (GAPDH).

Example 5: Inhibition of Host and Viral Protein Expression

Figure 5:
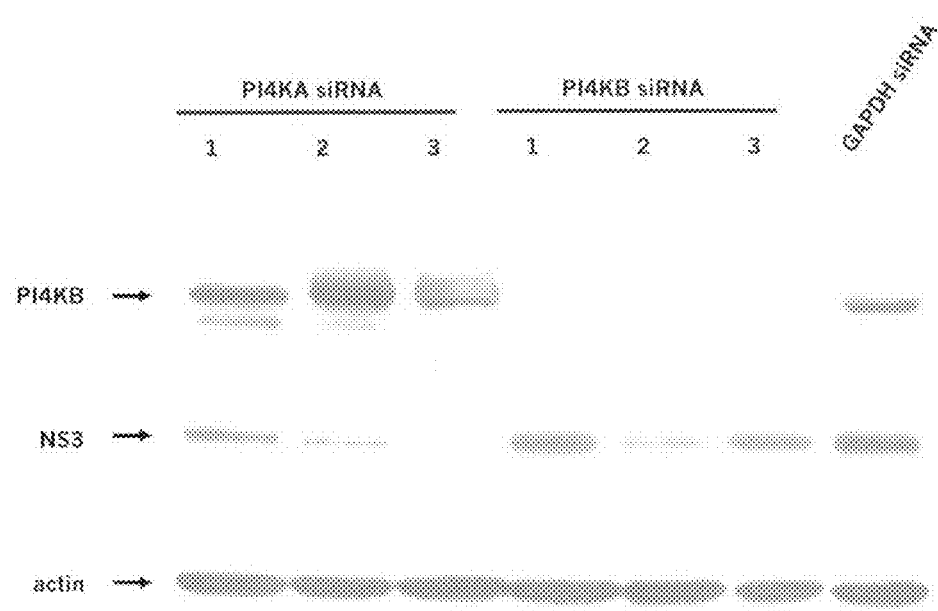
FIG. 5. Western blot results demonstrating level of protein expression of PI4KB, NS3 or actin (as indicated) after treatment of PI4KA siRNA (col 1-col 3 correspond to Table 2; PI4KA1; PI4A2 and PI4A3, respectively); or PI4KB siRNA (col 4-col 6 correspond to Table 1; PI4KB1; PI4KB2 and PI4KB3, respectively). GAPDH siRNA treatment is shown as a control.

In FIG. 5 whole cell lysates were made from Huh7 HCV subgenomic replicon cells transfected with siRNA or naïve cells alone. siRNA employed for the results in FIG. 5 are as named in Table 1 and Table 2.

Cells were lysed in radioimmunoprecipitation buffer (RIPA) (Boston Bioproducts, #BP-115) containing one protease cocktail inhibitor tablet (Roche, #04693116001) per 10 ml lysis buffer. Lysates were quantified using the BCA Protein Assay (Pierce Biotechnology, #23227) per the manufacturer's instructions. Equal amounts of lysate were loaded on a 15% Tris-HCL gel (Bio-Rad Laboratories, Hercules, Calif., #345-0019) and run at 200V for 1 hour. The gel was transferred to a nitrocellulose membrane (Bio-Rad Laboratories, #162-0232) for 1 hour at 100V. The membrane was blocked in 5% milk (Bio-Rad Laboratories, Hercules, Calif., #162-0232), TBS-0.1% Tween (Bio-Rad Laboratories, #170-6435, #161-0787), for 1 hour. Blots were probed with a mouse monoclonal antibody against PIK4CB (BD Biosciences, #611817) or a mouse monoclonal against the HCV protein NS3 (Virostat, #1828) and a mouse monoclonal antibody for β-Actin (Sigma, St. Louis, Mo., #A-5441), as a loading control, diluted in blocking buffer 1:1000 for 1 hour (antibodies against PIK4CA were not available). Following three successive washes with TB S-0.1% Tween (TBST), HRP-conjugated secondary antibody for mouse IgG (Sigma, #A4416), diluted in blocking buffer 1:5000, was added for 1 hour. The membrane was washed three times in TBST and immunoreactive bands were visualized using the SuperSignal West Femto chemiluminescent substrate (Pierce, #34096). There was no PI4KA antibody available so only the PI4KB protein was detected in FIG. 5.

Results in FIG. 5 show that the PI4KA siRNAs had no effect on PI4KB protein levels while the PI4KB siRNAs ablate the PI4KB protein in the Huh7 cells. Each siRNA tested also showed a measurable reduction in NS3 (viral) protein production relative to control, thus confirming direct activity on viral replication ability. The reduction of mRNA levels using these siRNAs correlated with protein knock down suggesting these human proteins are required for HCV replication.

Example 6: Confirmation Using Short Hairpin RNA (shRNA)

Figure 6:
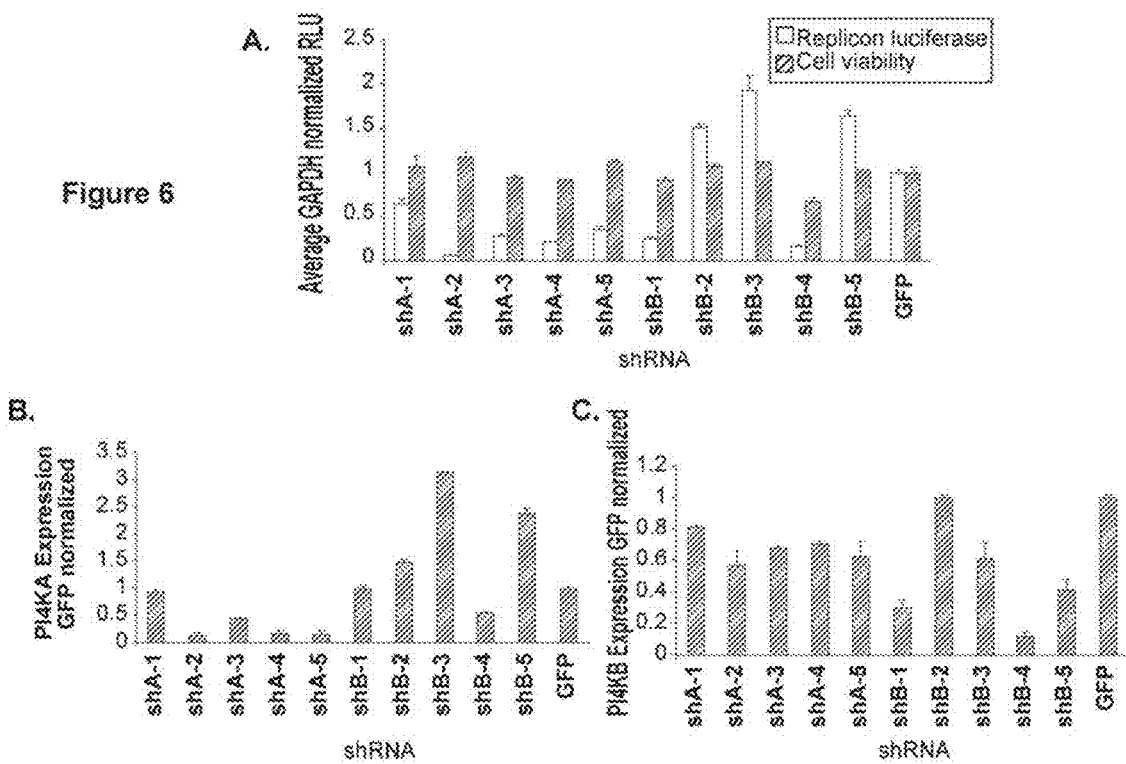
FIG. 6. shRNA sequences targeting PIK4CA and PIK4CB. A) Results of treatment of Clone A cells with indicated shRNA construct. Light bars indicate luciferase activity; dark bars indicate cell viability. All results are compared to control GAPDH treated cells: B) Effect of treatment with indicated shRNA on PI4KA expression (GFP normalized); C) Effect of treatment with indicated shRNA on PI4KB expression (GFP normalized); D) Western blot results demonstrating level of protein expression of PI4KB, NS3 or actin (as indicated) after treatment with shRNA targeting PI4KA (col 1-col 5 correspond to shA1-shA5, respectively); or shRNA targeting PI4KB (col 6-col 10 correspond to shB1-shB5, respectively). GFP shRNA treatment is shown as a control, all results taken at 96 hours after treatment with indicated shRNA; E) Western blot measuring effect of shA2 and shB1 on protein expression, 3 weeks after shRNA transduction (GFP control).

In FIG. 6 Short hairpin RNAs (shRNAs) targeting PIK4CA (NM_002650) and PIK4CB (NM_002651), were ordered as 5 individual Sigma MISSION™ shRNA. shRNAs targeting CD3δ (NM_000732), CD28 (NM_006139), CD29 (NM_033666) and GFP (U76561) were used as negative controls for inhibiting HCV replication (only GFP data shown). All shRNA sequences were constructed as in the human library MISSION™ TRC-Hs 1.0.(Human) (Moffat J. et al., A Lentiviral RNAi Library for Human and Mouse Genes Applied to an Arrayed Viral High-Content Screen. Cell, 124, 1283-1298. 2006; Stewart, S. A., et al., Lentivirus-delivered stable gene silencing by RNAi in primary cells., RNA, 9, 493-501 (2003); Zufferey R, et al., Multiply attenuated lentiviral vector achieves efficient gene delivery in vivo, Nat. Biotechnol. 5, 871-85 (1997); Zufferey R, et al., Self-inactivating lentivirus vector for safe and efficient in vivo gene delivery, J Virol., 72, 9873-80 (1998).

The shRNA sequences were distinct independent sequences from the siRNAs reported in the aforementioned experiments. Table 4 sets out the DNA sequences corresponding to the expressed RNA strand.

TABLE 4

| shRNA | Sequence (5' to 3') | SEQ ID No. |
|---|---|---|
| ShA-1 | CCGGGCTGCACAAATACTACATGAACTCGAGTTCATGTAGTATTTGTGCAGCTTTTT | 421 |
| ShA-2 | CCGGGCGTCTCATCACATGGTACAACTCGAGTTGTACCATGTGATGAGACGCTTTTT | 422 |
| ShA-3 | CCGGGCCAGGTTTAAGAACACAGAACTCGAGTTCTGTGTTCTTAAACCTGGCTTTTT | 423 |
| ShA-4 | CCGGCCAGTTCATCTGGAACATGAACTCGAGTTCATGTTCCAGATGAACTGGTTTTT | 424 |
| ShA-5 | CCGGCAAGCTCTTGAAGCACAGGTTCTCGAGAACCTGTGCTTCAAGAGCTTGTTTTT | 425 |
| ShB-1 | CCGGCCAGTTGCTTAACATGTACATCTCGAGATGTACATGTTAAGCAACTGGTTTTT | 426 |
| ShB-2 | CCGGCCGAGAGTATTGATAATTCATCTCGAGATGAATTATCAATACTCTCGGTTTTT | 427 |
| ShB-3 | CCGGCCATACAAGATTCTTGTGATTCTCGAGAATCACAAGAATCTTGTATGGTTTTT | 428 |
| ShB-4 | CCGGCGACATGTTCAACTACTATAACTCGAGTTATAGTAGTTGAACATGTCGTTTTT | 429 |
| ShB-5 | CCGGTCTCGGTACTTAGGACTTGATCTCGAGATCAAGTCCTAAGTACCGAGATTTT | 430 |

To test the shRNA, 6000 Huh7 HCV subgenomic replicon cells were plated in 96 well tissue culture plates. The following day, media was replaced with transduction media containing assay media with polybrene (sigma H9268) 8ug/ml final concentration and hepes (Invitrogen, #15630080) 10 mM final concentration. 1 µL shRNA virus was added per well and cells were centrifuged at 2100 rpms for 90 minutes at room temperature. Cells were incubated for 24 hours and were selected by adding puromycin (Sigma, #P9620) at 2 µg/ml final concentration. Cells were then incubated for a minimum of 72 hours and assayed for phenotype, analyzed by western and RT-PCR or propagated for long term knockdown studies. In FIG. 6A HCV replicon expression is measured by luciferase activity and normalized to GAPDH shRNA transduced cells. PI4KA and PI4KB mRNA levels were measured in the Huh7 cells after shRNA transduction using a PI4KA Taqman probe (FIG. 6B) or PI4KB Taqman probe (FIG. 6C) for RTPCR. PI4KB protein and NS3 protein levels were determined using Western blot methods similar to those in Example 5. Protein levels were measured after shRNA transduction for 96 hours (FIG. 6D) and for 3 weeks (FIG. 6E).

Results in FIG. 6A show that shRNA directed to PI4KA or PI4KB shRNAs can reduce HCV replicon activity as measured by luciferase activity and normalized to GAPDH shRNA transduced cells. FIG. 6B shows relative levels of PI4KA mRNA after treatment. The shRNA directed to PI4KA demonstrate substantial knock-down, whereas only one of those targeting PI4KB had an effect on PI4KA levels (perhaps due to high copy number and a low cross-reactivity with PI4KA). FIG. 6C shows that the shRNA directed to PI4KA had no effect on PI4KB mRNA levels, whereas most of the shRNA targeting PI4KB had significant knock-down of PI4KB. FIG. 6D shows at 96 hours after treatment, shRNA directed to either PI4KA or PI4KB successfully lowers NS3 viral protein production (and that PI4KA shRNA does not down regulate PI4KB protein levels). The results in FIG. 6E demonstrate that the knock-down of viral protein production can persist for at least 3 weeks In conclusion, there was a clear correlation between PI4KA mRNA reduction and NS3 protein levels indicating viral load in the cell was inhibited. There was a clear correlation between PI4KB mRNA and protein reduction and NS3 protein levels indicating viral load in the cell was inhibited.

Example 7: Treatment Before Infection or After Infection with Live Virus

Figure 7:
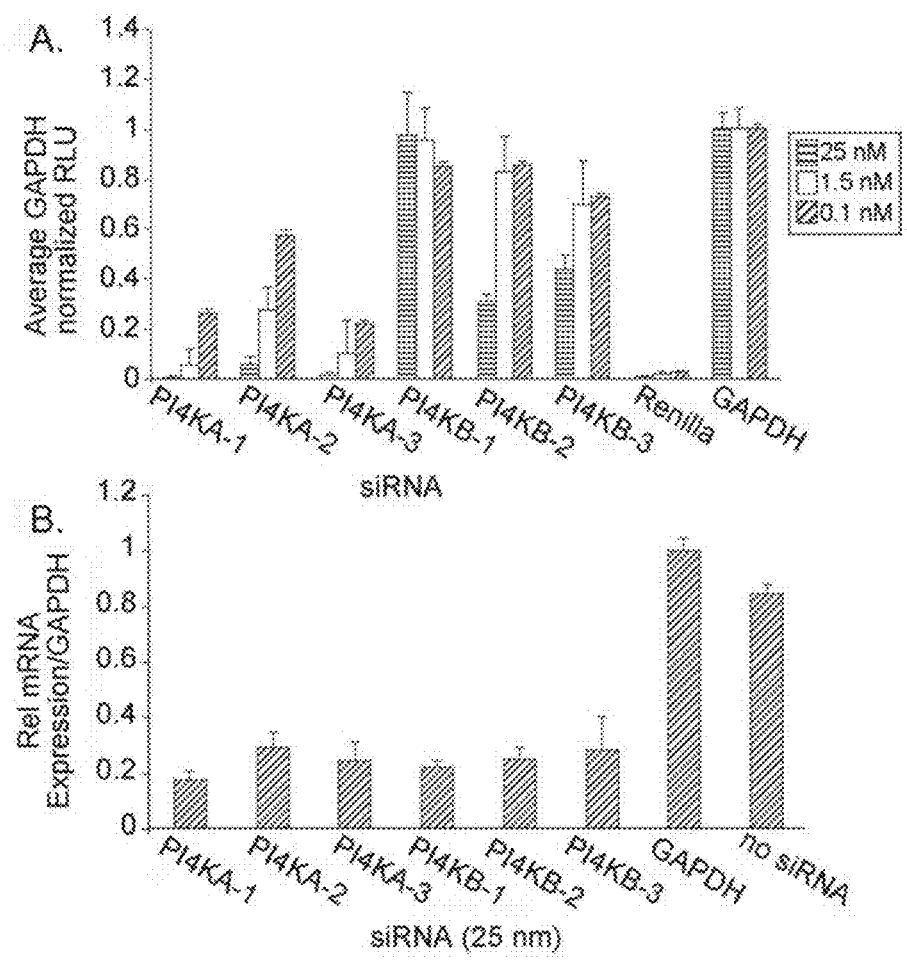
FIG. 7. Inhibition of HCV replication (live virus). Dose dependence of HCV replication upon treatment by the indicated siRNA. Cells are treated before HCV infection with indicated siRNA against either PIK4CA or PIK4CB. A) 25 nM (grey bar); 1.5 nM (white bar); 0.1 nM (dark bar). Results are normalized to HCV replication upon GAPDH siRNA treatment. *Renilla* siRNA is positive control. B) Expression of target mRNA in infected cells.

In this example, effective inhibition of HCV replication is achieved by treating cells before HCV infection with siRNA against either PIK4CA or PIK4CB (FIG. 7) or treating cells after HCV infection (FIG. 8). This example also demonstrates dose dependence of mRNA knock-down.

For this experiment, siRNAs against PIK4CA and PIK4CB (as designated in Table 1 and Table 2) were resuspended in siRNA buffer (Dharmacon, #B-002000-UB-015) to a stock concentration of 20 µM. 3 µL of each stock solution was diluted in 197 µL Opti-Mem in a 96 well PCR plate (ABgene, #AB-1000) to make a 300 nM working stamp. siRNAs were diluted in Optimem (Invitrogen Cat #51985-034) as 10× stocks and added to complete cell culture media to a final concentration of 25 nM, 1.5 nM, and 0.1 nM. 0.20 µL of Dharmafect1 transfection reagent (Dharmacon, #T2001-03) diluted in 10 µL Opti-Mem was added to each well of a 96 well tissue culture plate (Costar, #3917). 10 µL of each siRNA stamp was added to the 96 well plate containing the Dharmafect1 and incubated for 20 minutes to allow complexes to form. After the incubation, 10000 Huh7.5 cells in 100 µL assay media were added per well. Cells were incubated for 24 hours and then infected with the JFH-1 infectious HCV genotype 2 virus which contains a Renilla reporter. A siRNA against Renilla was used as positive control for inhibiting the Renilla, luciferase. The siRNAs were transfected before live virus infection (FIG. 7A) or after viral infection (FIG. 8A) demonstrating the siRNAs could block both uptake and replication of the HCV virus. Viral supernatants were collected over a time course to measure live virus secreted from the cells as measured by percent reinfection of naïve cells (FIG. 8B). The percent knock down of the mRNA in the Huh7 cells was determined by RTPCR (FIG. 7B).

We have used an Huh7 HCV replicon siRNA screen that identified several novel host factors required for optimal replicon driven luciferase activity. This screen was used to confirm the findings. This screen does not directly measure viral replication, it is assumed that luciferase expression levels are directly determined by the copy number of the virus replicon. The experiments illustrated in FIG. 7 and FIG. 8 indicate that active siRNAs described here indeed result in reduction of viral RNA production.

From a smart pool kinome screen, PIK4CB and PIK4CA have been identified as an essential host factors for HCV and other positive stranded RNA virus replication. Multiple independent siRNAs targeting the gene could significantally reduce luciferase levels while having no effect on cellular viability in the replicon cells. The siRNAs that reduced luciferase levels also inhibited mRNA levels of the respective target genes. Thus, we can conclude the siRNAs used in this study are on-target and significantly modulate HCV replication via reduction of their target cellular genes.

Without wishing to be bound to any particular mechanism of action to explain our findings, it is clear that the significance of these findings are several fold. PIK4 enzymes are required for the production of PtdIns4P in the ER and Golgi compartments. The production of PtdIns4P is needed to maintain Golgi integrity, bud vesicles from the Golgi and ER membranes, and modulate the production of Ins(1,4,5)P3, an essential signalling molecule through the intermediate Ins (4,5)P2 (Godi A, Pertile P, Meyers R, Marra P, Di Tullio Iurisci C, Luini A, Corda D, De Matteis M A. ARF mediates recruitment of PtdIns-4-OH kinase-beta and stimulates synthesis of PtdIns(4,5)P2 on the Golgi complex. Nat Cell Biol. 1999 September; 1(5):280-7.) While not desiring to be bound to any specific mechanism of action for the discovery herein, it is possible the activity of PIK4 enzymes could be linked to HCV replication based on the location of the HCV replication complex. If the replication complex requires intact Golgi and ER membranes then the disruption of PIK4 enzymes, and PtdIns4P production, would likely block the formation of a competent replication environment. As well, PIK4 enzymes are known to regulate trafficking of cerimide and cholesterol through the Golgi and ER membranes and aid in the formation of lipid rafts (Toth B, Balla A, Ma H, Knight Z A, Shokat K M, Balla T. Phosphatidylinositol 4-kinase IIIbeta regulates the transport of ceramide between the endoplasmic reticulum and Golgi. J Biol Chem. 2006 Nov. 24; 281(47):36369-77.) It is a strong possibility that the HCV replication complex requires lipid rafts for effective activity. If PIK4 knock down also perturbs cholesterol and cerimide transport, it could also contribute to inhibition of HCV replication (Ridsdale A, Denis M, Gougeon P Y, Ngsee J K, Presley J F, Zha X. Cholesterol is required for efficient endoplasmic reticulum-to-Golgi transport of secretory membrane proteins. Mol Biol Cell. 2006 April; 17(4):1593-605.) Finally, a number of proteins have been identified that contain PIP(4,5) specific PH domains and localization of such proteins appear to be regulated by PIK4 enzymes. Thus the role of PIK4 may also include redirecting cellular or viral proteins to sites of replication.

In conclusion, we have identified that PIK4CB and PIK4CA are human host factor enzymes that are required for HCV replication, and that dsRNA targeting these genes are suitable therapeutic targets for treating HCV and other positive stranded virus infections.

Those skilled in the art are familiar with methods and compositions in addition to those specifically set out in the instant disclosure which will allow them to practice this invention to the full scope of the claims hereinafter appended.

We claim:

1. A double-stranded ribonucleic acid (dsRNA) for inhibiting the expression of phosphatidylinositol4-kinase (PI4K) in a cell, wherein:
   the dsRNA comprises a first strand comprising about 19 to about 30 nucleotides, and a second strand comprising about 19 to about 30 nucleotides;
   the first strand and the second strand have substantially complementary throughout a region of complementarity of about 19 to about 24 nucleotides; the sequence of the first strand comprises at least 19 contiguous nucleotides from one of SEQ ID NOs: 225, 278, or 308; and
   the dsRNA comprises at least one modified nucleotide that is a 2'-O-methyl modified nucleotide, a nucleotide comprising a 5'-phosphorothioate group, a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, a morpholino nucleotide, a phosphoramidate, or a non-natural base comprising nucleotide.

2. A pharmaceutical composition comprising the dsRNA of claim 1 and a pharmaceutically acceptable carrier.

3. A composition comprising the dsRNA of claim 1, further comprising one or more additional dsRNAs for inhibiting the expression of phosphatidylinositol 4-kinase (PI4K) in a cell.

4. The dsRNA of claim 1, wherein the dsRNA is conjugated to one or more ligands.

5. The dsRNA of claim 4, wherein the ligand comprises one or more carbohydrates.

6. The dsRNA of claim 4, wherein the ligand comprises cholesterol or a cholesteryl derivative.

7. A method for inhibiting the expression of a phosphatidylinositol 4-kinase (PI4K) gene in a cell, the method comprising: (a) introducing into the cell a double-stranded ribonucleic acid (dsRNA) of claim 1 into a cell, and (b) maintaining the cell for a time sufficient to obtain degradation of the mRNA transcript of the PIK4 gene, thereby inhibiting expression of the PIK4 gene in the cell.

8. A vector for inhibiting the expression of the phosphatidylinositol 4-kinase (PIK4) gene in a cell, the vector comprising a regulatory sequence operably linked to a nucleotide sequence that encodes at least one strand of the dsRNA of claim 1.

9. A cell comprising the vector of claim 8.

10. A method of treating a pathological process mediated by positive stranded RNA virus infection, comprising administering to a subject in need of such treatment, prevention, or management a therapeutically or prophylactically effective amount of a dsRNA of claim 1.

11. The method of claim 10, wherein the positive stranded RNA virus is Hepatitis C Virus (HCV), human papilloma virus (HPV), or Dengue virus.

* * * * *